US009365825B2

(12) United States Patent
Turner et al.

(10) Patent No.: US 9,365,825 B2
(45) Date of Patent: Jun. 14, 2016

(54) EXPANSION OF ADULT STEM CELLS IN VITRO

(71) Applicant: Taiga Biotechnologies, Inc., Aurora, CO (US)

(72) Inventors: Brian Curtis Turner, Denver, CO (US); Yosef Refaeli, Denver, CO (US); Gregory Bird, Littleton, CO (US)

(73) Assignee: TAIGA BIOTECHNOLOGIES, INC., Aurora, CO (US)

( * ) Notice: Subject to any disclaimer, the term of this patent is extended or adjusted under 35 U.S.C. 154(b) by 0 days.

(21) Appl. No.: 13/795,659

(22) Filed: Mar. 12, 2013

(65) Prior Publication Data
US 2014/0273212 A1 Sep. 18, 2014

Related U.S. Application Data

(60) Provisional application No. 61/776,422, filed on Mar. 11, 2013.

(51) Int. Cl.
*C12N 5/071* (2010.01)
*C12N 5/0789* (2010.01)
*C07K 14/82* (2006.01)

(52) U.S. Cl.
CPC .............. *C12N 5/0647* (2013.01); *C07K 14/82* (2013.01); *C12N 2501/125* (2013.01); *C12N 2501/145* (2013.01); *C12N 2501/22* (2013.01); *C12N 2501/2303* (2013.01); *C12N 2501/2306* (2013.01); *C12N 2501/26* (2013.01); *C12N 2501/606* (2013.01); *C12N 2501/998* (2013.01)

(58) Field of Classification Search
CPC ........................ C12N 5/0647; C12N 2501/125
See application file for complete search history.

(56) References Cited

U.S. PATENT DOCUMENTS

| | | | |
|---|---|---|---|
| 4,963,489 A | 10/1990 | Naughton et al. | |
| 5,476,996 A | 12/1995 | Wilson et al. | |
| 5,698,767 A | 12/1997 | Wilson et al. | |
| 5,811,301 A | 9/1998 | Cameron | |
| 5,824,837 A | 10/1998 | Chen et al. | |
| 5,847,082 A | 12/1998 | Rother et al. | |
| 5,849,288 A | 12/1998 | Reisner | |
| 6,358,739 B1 | 3/2002 | Baetge et al. | |
| 6,451,558 B1 | 9/2002 | Cooke et al. | |
| 6,451,601 B1 | 9/2002 | Baetge et al. | |
| 6,645,501 B2 | 11/2003 | Dowdy | |
| 7,135,287 B1 | 11/2006 | Lonberg et al. | |
| 7,311,920 B1 | 12/2007 | Devico et al. | |
| 7,582,745 B2 | 9/2009 | Sah et al. | |
| 7,767,453 B2 | 8/2010 | Zhang et al. | |
| 2001/0049393 A1 | 12/2001 | Coller et al. | |
| 2002/0098166 A1 | 7/2002 | Havemann et al. | |
| 2003/0072794 A1 | 4/2003 | Boulikas | |
| 2005/0220705 A1 | 10/2005 | Brooks et al. | |
| 2005/0281816 A1 | 12/2005 | Lamping et al. | |
| 2006/0115898 A1 | 6/2006 | Zhang et al. | |
| 2006/0154331 A1 | 7/2006 | Avidan et al. | |
| 2006/0156422 A1 | 7/2006 | Dalrymple et al. | |
| 2007/0011753 A1 | 1/2007 | Ito et al. | |
| 2007/0067854 A1 | 3/2007 | Habu et al. | |
| 2007/0093420 A1 | 4/2007 | Yeomans et al. | |
| 2007/0116691 A1* | 5/2007 | Cambier et al. ........... 424/93.21 |
| 2007/0130628 A1 | 6/2007 | Brown | |
| 2007/0248618 A1 | 10/2007 | Cohen | |
| 2009/0291094 A1 | 11/2009 | Refaeli et al. | |
| 2010/0047217 A1* | 2/2010 | Refaeli et al. ............... 424/93.21 |
| 2010/0055129 A1 | 3/2010 | Refaeli et al. | |
| 2010/0233804 A1* | 9/2010 | Zhou et al. ..................... 435/354 |
| 2010/0279351 A1 | 11/2010 | Refaeli | |
| 2011/0218210 A1 | 9/2011 | Refaeli et al. | |

FOREIGN PATENT DOCUMENTS

| | | |
|---|---|---|
| EP | 1 103 615 | 5/2001 |
| EP | 1 103 615 A1 | 5/2001 |
| EP | 1 357 184 | 10/2003 |
| EP | 1 792 627 | 6/2007 |
| GB | 2 387 599 | 10/2003 |
| JP | 2000-189157 | 7/2000 |
| JP | 2001-518300 | 10/2001 |
| JP | 2002-541786 | 12/2002 |
| JP | 2003-514565 | 4/2003 |
| JP | 2005-523012 | 8/2005 |
| JP | 2005-525085 | 8/2005 |
| JP | 2005-527211 | 9/2005 |
| JP | 2009-511081 | 3/2009 |
| WO | WO-94/04686 | 3/1994 |
| WO | WO-94/19465 | 9/1994 |
| WO | WO-98/10058 | 3/1998 |
| WO | WO-99/16884 | 4/1999 |
| WO | WO-99/45962 | 9/1999 |
| WO | WO-99/53023 | 10/1999 |
| WO | WO-99/53028 | 10/1999 |
| WO | WO-00/09669 | 2/2000 |

(Continued)

OTHER PUBLICATIONS

Rabbitts et al. (EMBO Journal. 1985; 4(8): 2009-2015).*
Kitada et al. (Antisense Research and Development. 1994; 4: 71-79).*
Ho et al. (Cancer Research. 2001; 61: 474-477).*
Choi, et al., "Status Epilepticus-Induced Somatostatinergic Hilar Interneuron Degeneration Is Regulated by Striatal Enriched Protein Tyrosine Phosphatase", Journal of Neuroscience, (2007), vol. 27, No. 11, pp. 2999-3009.
English Translation of Office Action received for Chinese Patent Application No. 200980126312.4 dated Jan. 22, 2014, 3 pages.
English Translation of Office Action received for Japanese Patent Application No. 2011-525258 dated Feb. 17, 2014, 4 pages.
Iritani, et al., "c-Myc enhances protein synthesis and cell size during B lymphocyte development", PNAS, (1999), vol. 96, No. 23, pp. 13180-13185.

(Continued)

*Primary Examiner* — Scott Long
(74) *Attorney, Agent, or Firm* — Foley & Lardner LLP

(57) ABSTRACT

Disclosed are methods for manipulating and expanding stem cell populations, including adult stem cells, the cells produced by such methods, and various protein constructs related thereto.

29 Claims, 47 Drawing Sheets

(56) References Cited

FOREIGN PATENT DOCUMENTS

| WO | WO-00/61617 | 10/2000 |
|---|---|---|
| WO | WO-00/62067 | 10/2000 |
| WO | WO-01/34824 | 5/2001 |
| WO | WO-01/38548 | 5/2001 |
| WO | WO-02/074968 | 9/2002 |
| WO | WO-03/038057 | 5/2003 |
| WO | WO-03/089580 | 10/2003 |
| WO | WO-03/089630 | 10/2003 |
| WO | WO-03/097675 | 11/2003 |
| WO | WO-2004/035535 | 4/2004 |
| WO | WO-2005/014785 | 2/2005 |
| WO | WO-2005/084158 | 9/2005 |
| WO | WO-2006/032876 | 3/2006 |
| WO | WO-2006/116512 | 11/2006 |
| WO | WO-2007/047583 | 4/2007 |
| WO | WO-2007/067183 | 6/2007 |
| WO | WO-2008/112922 | 9/2008 |
| WO | WO-2009/059304 | 5/2009 |
| WO | WO-2009/139930 | 11/2009 |
| WO | WO-2010/011644 | 1/2010 |
| WO | WO-2010/025421 | 3/2010 |

OTHER PUBLICATIONS

Jadlowsky, et al., "Dominant negative mutant Cyclin T1 proteins inhibit Hiv transcription by specifically degrading Tat", Retrovirology, (2008), vol. 5, Article 63, 12 pages.
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Non-final Office Action on U.S. Appl. No. 12/467,957 dated Apr. 4, 2014, 14 pages.
Non-final Office Action on U.S. Appl. No. 13/797,648 dated Apr. 3, 2014, 13 pages.
Office Action received for Australian Patent Application No. 2009246876 dated Jan. 17, 2014, 6 pages.
Office Action received for European Application No. 09810692.5 dated Feb. 25, 2014, 3 pages.
Office Action received for Indian Application No. 3332/DELNP/2008 dated Aug. 23, 2013, 3 pages.
Snyder, et al., "Regulation of NMDA receptor trafficking by amyloid-3B2", Nature Neuroscience, (2005), vol. 8, No. 8, pp. 1051-1058.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.
Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
English Translation of Notification of Reasons of Refusal for Japanese Patent Application No. 2012-221023 dated Jun. 24, 2014, 2 pages.
English Translation of Office Action on Chinese Application No. 200980127166.7 dated Apr. 11, 2014, 3 pages.
English Translation of Office Action on Japanese Patent Application. No. 2012-221023 dated Apr. 22, 2014, 3 pages.
English Translation of Third Office Action on Japanese Patent Application No. 2009-553785 dated Apr. 22, 2014, 3 pages.
Examination Report for Indian Patent Application No. 3332/DELNP/2008 dated Aug. 23, 2013, 6 pages.
Examination Report on Australian Patent Application No. 2012216462 dated Mar. 6, 2014, 3 pages.
Final Office Action on U.S. Appl. No. 11/583,970 dated Apr. 9, 2014, 20 pages.
Gauss et al., "DEAE-Dextran Enhances Electroportation of Mammalian Cells", Nucleic Acids Research, vol. 20, No. 4, pp. 6739-6740 (1992).
Jayapal et al., "Down-regulation of Myc is Essential for Terminal Erythroid Maturation" The Journal of Biological Chemistry, vol. 285, No. 51, pp. 40252-40265, Dec. 17, 2010.
Non-Final Office Action on U.S. Appl. No. 12/701383 dated Jun. 13, 2014, 26 pages.
Notice of Allowance on U.S. Appl. No. 12/550,166 dated Apr. 28, 2014, 4 pages.
Notification prior to Allowance of Israeli Patent Application No. 209343 dated Apr. 7, 2014, 2 pages.
Office Action on Canadian Application No. 2,626,525 dated Apr. 8, 2014, 4 pages.
Office Action on Canadian Patent Application No. 2,680,613 dated Nov. 21, 2013, 3 pages.
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).
Wilson, et al. "c-MYC Controls the Balance Between Hematopoietic Stem Cell Self-Renewal and Differentiation" Genes and Development, vol. 18, pp. 2747-2763 (2007).
Aubry et al., "N-Myc Shares Cellular Functions with c-Myc", DNA and Cell Biology, vol. 19, No. 6, Jun. 2000, pp. 353-364.
Austrian Search Report and Written Opinion received for Singapore Patent Application No. 201101367-9, mailed on Mar. 23, 2012, 17 pages.
Baum, Christopher, "Insertional Mutagenesis in Gene Therapy and Stem Cell Biology", Current Opinion in Hematology, vol. 14, Jul. 2007, pp. 337-342.
Beerens et al., "Protein Transduction Domains and their Utility in Gene Therapy", Current Gene Therapy, vol. 3, No. 5, 2003, pp. 486-494.
Berkson et al., "Pilot Screening Programme for Small Molecule Activators of p53", International Journal of Cancer, vol. 115, 2005, pp. 701-710.
Bunting et al., "Restoration of lymphocyte function in Janus kinase 3-deficient mice by retro-viralmediated gene transfer," Nature Medicine 4:58-64 (1998).
Buske et al., "Deregulated Expression of HOXB4 Enhances the Primitive Growth Activity of Human Hematopoietic Cells", Blood, vol. 100, No. 3, Aug. 1, 2002, pp. 862-868.
Capecchi, Mario R., "Altering the Genome by Homologous Recombination", Science, vol. 244, No. 4910, Jun. 16, 1989, pp. 1288-1292.
Caron, et al., "Endosome disruption enhances the functional nuclear delivery of Tat-fusion proteins", Biochem Biophys Res Commun, (2004), vol. 319, pp. 12-20.
Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.
Chadwick, et al., "Notch Signaling Induces Apoptosis in Primary Human CD34 Hematopoietic Progenitor Cells", Stem Cells, (2007), vol. 24, pp. 203-210.
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Cheng et al., "BCL-2, BCL-XL, Sequester BH3 Domain-Only Molecules Preventing BAX- and BAK-Mediated Mitochondrial Apoptosis", Molecular Cell (2001) vol. 8, pp. 705-711.
Chin et al., "Essential Role for Oncogenic Ras in Tumour Maintenance", Nature, vol. 400, 1999, pp. 468-472.
Choi et al., "Myc Protein is Stabilized by Suppression of a Novel E3 Ligase Complex in Cancer Cells", Genes & Development, vol. 24, 2010, pp. 1236-1241.
Coller, et al., "Expression Analysis with Oligonucleotide Microarrays Reveals that MYC Regulates Genes Involved in Growth, Cell Cycle, Signaling, and Adhesion", PNAS, (2000), 97(7):3260-3265.
Conti, et al., "Gene therapy using neural stem cells," Methods Mol. Biol. 198:233-244 (2002).

(56) References Cited

OTHER PUBLICATIONS

Dang et al., "Identification of the Human c-myc Protein Nuclear Translocation Signal", Molecular and Cellular Biology, vol. 8, No. 10, Oct. 1988, pp. 4048-4054.
Dang, Chi V., "c-Myc Target Genes Involved in Cell Growth, Apoptosis, and Metabolism", Molecular and Cellular Biology, vol. 19, No. 1, Jan. 1999, pp. 1-11.
Deocampo, et al., Cooperation of bcl-2 and myc in the neoplastic transformation of normal rat liver epithelial cells is related to the down-regulation of gap junction-mediated intercellular communication, Carcinogenesis, 2000, vol. 21, No. 8 pp. 1501-1506.
Eilers, et al., "Chimeras of MYC Oncoprotein and Steroid Receptors Cause Hormone-Dependent Transformation of Cells," Nature 340(6228):66-68 (1989).
Eischen, et al., "Apoptosis Triggered by Myc-Induced Suppression of Bcl-XL or Bcl-2 Is Bypassed during Lymphomagenesis", Molecular Cell Biology, 2001, 21: 5063-5070.
English Translation of Fourth Office Action received for Chinese Patent Application No. 200880015602.7 dated Nov. 11, 2013, 6 pages.
English Translation of Office Action received for Eurasian Patent Application No. 201001762/28, posted Oct. 16, 2013, 1 page.
English translation of Office Action received for Israeli Patent Application No. 190946, dated Apr. 22, 2013, 1 page.
English translation of Office Action received for Japanese Application No. 2008-536713 dated Aug. 5, 2013, 2 pages.
English Translation of Office Action received for Israeli Patent Application No. 209968 dated Jan. 2, 2014, 2 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
Esdar, C., et al., "Differentiation-associated apoptosis of neural stem cells is effected by Bcl-2 overexpression: impact on cell lineage determination," Eur. J. Cell Biol.,(2001), vol. 80, No. 8, pp. 539-553.
Extended European Search Report and Search Opinion received for Patent Application No. 12187097.6, mailed on Mar. 27, 2013, 8 pages.
Extended European Search Report received for European Patent Application No. 09810692.5, mailed on Jul. 11, 2011, 5 pages.
Extended European Search Report received for European Patent Application No. 06826025.6, mailed on Aug. 13, 2009, 8 pages.
Extended European Search Report received for European Patent Application No. 09747016.5, mailed on May 30, 2012, 8 pages.
Extended European Search Report received for European Patent Application No. 09800871. 7, mailed on Jun. 24, 2011, 5 pages.
Extended European Search Report received for European Patent Application No. 12187077.8, mailed on Mar. 25, 2013, 7 pages.
Felsher( et al., "Reversible Tumorigenesis by MYC in Hematopoietic Lineages", (1999), Molecular Cell, 4: 199-207.
Final Office Action received for Korean Patent Application No. 10-2009-7021320, mailed on May 29, 2013, 6 pages (3 pages of English Translation and 3 pages of Office Action).
Final Office Action received for U.S. Appl. No. 11/583,970, mailed on Nov. 17, 2011, 15 pages.
Final Office Action received for U.S. Appl. No. 12/701,383, mailed on Nov. 16, 2011, 13 pages.
Final Office Action received for U.S. Appl. No. 11/583,970, mailed on Nov. 26, 2008, 13 pages.
Final Office Action received for U.S. Appl. No. 12/048,148, mailed on Feb. 15, 2013, 17 pages.
Final Office Action received for U.S. Appl. No. 12/467,957 mailed on Feb. 28, 2011, 8 pages.
Final Office Action received for U.S. Appl. No. 12/550,166, mailed on May 11, 2012, 12 pages.
Final Office Action received on U.S. Appl. No. 11/583,970, mailed on Nov. 4, 2009, 10 pages.

Gauss, DEAE-dextran enhances electoportation [sic] of mammalian cells, Nucleic Acids Research, 1992, vol. 20, No. 24, pp. 6739-6740.
Guzman et al., "Preferential induction of apoptosis for primary human leukemic stem cells," PNAS 99(25):16220-16225 (2002).
Habib et al., "Myc Stimulates B Lymphocyte Differentiation and Amplifies Calcium Signaling", J.Cell Biol., vol. 179, No. 4, 2007, pp. 717-731.
Hann et al., "Proteins Encoded by the Human C-Myc Oncogene: Differential Expression in Neoplastic Cells", Mol: Cell. Biol., vol. 4, No. 11, Nov. 1984, pp. 2486-2497.
Hiramatsu et al., "Complete Reconstitution of Human Lymphocytes from Cord Blood CD34 Cells Using the NOD/SCID/ycnull Mice Model", Blood, vol. 102, No. 3, 2003, pp. 873-880.
Hoffman, "Progress in the develoment of systems for in vitro expansion of human hematopoietic stem cells," Curr. Op. Hematology 6(3): 14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurons by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Huang et al., "Dynamic Regulation of C-Myc Proto-Oncogene Expression during Lymphocyte Development Revealed by a GFP-c-Myc Knock-In Mouse", Eur. J. Immunol., vol. 38, No. 2, 2008, pp. 342-349.
Huettner et al., "Reversibility of Acute B-Cell Leukaemia Induced by BCR-ABL 1," Nature Genetics, vol. 24, 2000, pp. 57-60.
International Preliminary Report on Patentability received for PCT Patent Application No. PCT/US2006/040379, issued on Apr. 23, 2008, 5 pages.
International Preliminary Report on Patentability received for PCT Patent Application No. PCT/US2008/056896, issued on Sep. 15, 2009, 4 pages.
International Preliminary Report on Patentability received for PCT Patent Application No. PCT/US2008/082263, issued on May 4, 2010, 6 pages.
International Preliminary Report on Patentability Received for PCT Patent Application No. PCT/US2009/003105, issued on Nov. 17, 2010, 6 pages.
International Preliminary Report on Patentability received for PCT Patent Application No. PCT/US2009/051242, issued on Jan. 25, 2011, 6 pages.
International Preliminary Report on Patentability received for PCT Patent Application No. PCT/US2009/055443, issued on Mar. 1, 2011, 6 pages.
International Search Report and Written Opinion for International (PCT) Patent Application No. PCT/US06/040379, mailed Sep. 24, 2007, 6 pages.
International Search Report and Written Opinion received for PCT Patent Application No. PCT/US2008/056896 mailed on Aug. 14, 2008, 5 pages.
International Search Report and Written Opinion received for PCT Patent Application No. PCT/US2008/082263, mailed on Jun. 25, 2009, 8 pages.
International Search Report and Written Opinion received for PCT Patent Application No. PCT/US2009/003105, mailed on Jan. 15, 2010, 9 pages.
International Search Report and Written Opinion received for PCT Patent Application No. PCT/US2009/051242, mailed on Feb. 19, 2010, 9 pages.
International Search Report and Written Opinion received for PCT Patent Application No. PCT/US2009/055443, mailed on Jun. 30, 2010, 11 pages.
Ju, et al., "Anti-Apoptotic Therapy with a Tat Fusion Protein Protects Against Excitotoxic Insults in Vitro and in Vivo", Experimental Neurology, vol. 210, 2008, pp. 602-607.

(56) References Cited

OTHER PUBLICATIONS

Kelso et al., "Survival of the Myeloid Progenitor Cell Line FDC-P1 is Prolonged by Interferon-y or Interleukin-4", Growth Factors, vol. 6, No. 3, 1992, pp. 233-242.
Korbling et al., "Allogenic Blood Stem Cell Transplantation: Peripheralization and Yield of Donor-Derived Primitive Hematopoietic Progenitor Cells (CD34+Thy-Idim) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT-HOXB4 protein," Nature Mediciine 9(11):1428-1432 (2003).
Li et al., "Reconstitution of Functional Human B Lymphocytes in NOD/SCID Mice Engrafted with ex vivo Expanded CD34 Cord Blood Cells", Experimental Hematology, vol. 30, 2002, pp. 1036-1043.
Littlewood, et. al., "A modified oestrogen receptor ligand-binding domain as an improved switch for the regulation of heterologous proteins", Nucleic Acids Research, (1995), vol. 23, No. 10, pp. 1686-1690.
Macpherson, P. et al., "Activity-dependent gene regulation in conditionally-immortalized muscle precursor cell lines," J. Cell. Biol. 91(4):821-839 (2004).
McCarthy, "Underground movement", Nature Reviews Cancer, (2007), vol. 7, 1 page, published online Oct. 11, 2007.
Melkonyan et al., "Electroporation efficiency in mammalian cells is increased by dimethyl sulfoxide (DMSO)," Nucleic Acids Research 24:4356-4357 (1996).
Merino et al., "Developmental Regulation of the Bcl-2 Protein and Susceptibility to Cell Death in B Lymphocytes", The EMBO Journal, vol. 13, No. 3, 1994, pp. 683-691.
Miller et al., "Expansion in vitro of adult murine hematopoietic stem cells with transplantable lympho-myeloid reconsituting ability," PNAS USA 94: 13648-13653 (1997).
Moore et al., "In Vitro Maintenance of Highly Purified, Transplantable hematopoietic Stem Cells," Blood 89(12):4337-4347 (1997).
Mooslehner et al., Retroviral Integration Sites in Transgenic Mov Mice Frequently Map in the Vicinity of Transcribed DNA Regions,: J. Virology 64:3056-3058 (1990).
Muchmore et al., "X Ray and NMR Structure of Human BcI-xL, an Inhibitor of Programmed Cell Death", Nature, vol. 381, May 23, 1996, pp. 335-341.
Non Final Office Action received for U. S. Patent Application No. 11/583,970 (106417-0140), mailed on May 9, 2011, 10 pages.
Non Final Office Action received for U.S. Appl. No. 12/048,148, mailed on Oct. 13, 2011, 9 pages.
Non Final Office Action received for U.S. Appl. No. 12/962,197, mailed on Aug. 26, 2011, 11 pages.
Non-Final Office Action on U.S. Appl. No. 11/583,970 dated Sep. 20, 2013, 19 pages.
Non-Final Office Action received for U.S. Appl. No. 11/583,970, mailed on Mar. 12, 2008, 13 pages.
Non-Final Office Action received for U.S. Appl. No. 12/467,957 mailed on Oct. 13, 2010, 15 pages.
Non-Final Office Action received for U.S. Appl. No. 12/701,383, mailed on Apr. 28, 2011, 9 pages.
Non-Final Office Action received for U.S. Appl. No. 11/583,970, mailed on Mar. 23, 2009, 11 pages.
Non-Final Office Action received for U.S. Appl. No. 12/048,148 mailed on Jan. 19, 2011, 6 pages.
Non-Final Office Action received for U.S. Appl. No. 12/048,148, mailed on May 11, 2012, 9 pages.
Non-Final Office Action received for U.S. Appl. No. 12/506,894, mailed on Apr. 27, 2012, 13 pages.
Non-Final Office Action received for U.S. Appl. No. 12/550,166 mailed on Jan. 11, 2012, 7 pages.
Notice of Allowance received for U.S. Appl. No. 12/550,166, mailed on Nov. 26, 2012, 9 pages.
Office Action received for Australian Patent Application No. 2006304392, mailed on Jul. 16, 2012, 3 pages.
Office Action received for Australian Patent Application No. 2009285547, mailed on Jul. 25, 2011, 2 pages.
Office Action received for Canadian Patent Application No. 2626525, dated Apr. 17, 2013, 4 pages.
Office Action received for Canadian Patent Application No. 2731767, mailed on Jul. 25, 2012, 3 pages.
Office Action received for Canadian Patent Application No. 2735522, mailed on Sep. 10, 2012, 3 pages.
Office Action received for Chinese Patent Application No. 200580031540.5 (106417-0144), mailed on Jul. 3, 2012, English translation, 11 pages.
Office Action received for Chinese Patent Application No. 200680045545.8, mailed on Dec. 31, 2010, English translation, 8 pages.
Office Action received for Chinese Patent Application No. 200680045545.8, mailed Sep. 15, 2011, English translation, 9 pages.
Office Action received for Chinese Patent Application No. 200880015602.7, mailed on Jan. 31, 2012, 16 pages (10 pages of English translation and 6 pages of Office Action).
Office Action received for Chinese Patent Application No. 200880015602.7, mailed on May 9, 2013, 13 pages (8 pages of English Translation and 5 pages of Official copy).
Office Action received for Chinese Patent Application No. 200880015602.7, mailed on Oct. 31, 2012, 10 pages (6 pages of English Translation and 4 pages of Chinese Office Action).
Office Action received for Chinese Patent Application No. 200980126312.4, issued on Aug. 28, 2012, 12 pages (6 pages of English Translation and 6 pages of Office Action).
Office Action received for Chinese Patent Application No. 200980127166.7, mailed on Dec. 5, 2012, 4 pages (1 page of English Translation and 3 pages of Office Action).
Office Action received for Chinese Patent Application No. 200980126312.4, mailed on Jan. 30, 2012, 14 pages (7 pages of English translation and 7 pages of Office Action).
Office Action received for European Patent Application No. 06826025.6, mailed on Sep. 1, 2009, 3 pages.
Office Action received for European Patent Application No. 06826025.6, mailed on Sep. 22, 2009, 1 page.
Office Action received for European Patent Application No. 08743862.8, mailed on May 14, 2010, 6 pages.
Office Action received for European Patent Application No. 08743862.8, mailed on Sep. 23, 2010, 6 pages.
Office Action received for European Patent Application No. 09747016.5, mailed on Apr. 9, 2013, 6 pages.
Office Action received for European Patent Application No. 09810692.5, mailed on Mar. 28, 2012, 3 pages.
Office Action received for Israel Patent Application No. 200919, mailed on Jan. 17, 2013, 4 pages (2 pages of English Translation and 2 pages of Official Copy).
Office Action received for Israel Patent Application No. 209343, mailed on Aug. 14, 2012, 3 pages (2 pages of English Translation and 1 page of Office Action).
Office Action received for Israel Patent Application No. 209968, mailed on Aug. 21, 2012, 4 pages (2 pages of English Translation and 2 pages of Office Action).
Office Action received for Israel Patent Application No. 200919, mailed on Dec. 5, 2011, 2 pages of English Translation only.
Office Action received for Israeli Patent Application No. 190946, mailed on Jul. 3, 2012, 1 page, (English Translation only).
Office Action received for Israeli Patent Application No. 208810, mailed on Jan. 2, 2013, 4 pages. (English Translation only).
Office Action received for Japanese Application No. 2011-520133, dated Feb. 5, 2014, 4 pages. (in Japanese).
Office Action received for Japanese Patent Application No. 2008-536713, mailed on Jul. 3, 2012, 2 pages (no English Translation Provided).
Office Action received for Japanese Patent Application No. 2009-553785, mailed on Jun. 19, 2012, 6 pages (2 pages of English Translation and 4 pages of Office Action).
Office Action received for Korean Patent Application No. 10-2008-7011791, dated May 28, 2013, English translation, 3 pages.

(56) References Cited

OTHER PUBLICATIONS

Office Action received for Korean Patent Application No. 10-2009-7021320, mailed on Jul. 29, 2011, 7 pages (3 pages of English Translation and 4 pages of Office Action).
Office Action received for Korean Patent Application No. 10-2009-7021320, mailed on Sep. 18, 2012, 11 pages (7 pages of English Translation and 4 pages of Office Action).
Oral Proceedings Summons received for European Patent Application No. 08743862.8, mailed on May 14, 2012, 6 pages.
Pierelli et al., "Modulation of bcl-2 and p27 in human primitive proliferating hematopoietic progenitors by autocrine TGF-B 1 is a cell cycle-independent effect and influences their hematopoietic potential,"Blood 95:3001-3010 (2000).
Pinto et al., "Hematopoietic progenitor/stem cells immortalized by Lhx2 generate functional hematopoietic cells in vivo," Blood 99(11):3939-3946 (2002).
Podsypanina, K. et al., "Oncogene cooperation in tumor maintenance and tumor recurrence in mouse mammary tumors induced by MYC and mutant Kras," PNAS 105(13):5242-5247 (2008).
Pollock, K. et al., "A conditionally immortal clonal stem cell line from human cortical neuroepithelium for the treatment of ischemic stroke," Exp. Neurol., (2006), vol. 199, No. 1, pp. 143-155.
Qin et al., "Nuclear Factor KB Nuclear Translocation Upregulates c-Myc and p53 Expression during NMDA Receptor—Mediated Apoptosis in Rat Striatum", The Journal of Neuroscience, vol. 19, No. 10, May 15, 1999, pp. 4023-4033.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Raymon, H.K. et al., "Immortalized human dorsal root ganglion cells differentiate into neurons with nociceptive properties," J. Neuroscience 19(13):5420-5428 (1999).
Refaeli, et al., "The protooncogene MYC can break B cell tolerance," PNAS, (2005), 102(11):4097-4102.
Refaeli, Y, "The B-Cell Antigen Receptor and Overexpression of MYC Can Cooperate in the Genesis of B-Cell Lymphomas", PLOS Biology, Vol .6, No. 6, e152, 2008, pp. 1208-1225.
Restriction Requirement received for U.S. Appl. No. 11/583,970, mailed on Nov. 13, 2007, 14 pages.
Restriction Requirement received for U.S. Appl. No. 12/701,383, mailed on Jan. 25, 2011, 10 pages.
Richter, et al., "Lhx.2 expression in hematopoietic progenitor/stem cells in vivo causes a chronic myeloproliferative disorder and altered globin expression," J. Hematol., (2003), 88(12):1336-1347.
Roh, M. et al., "Transgenic Mice for Cre-Inducible Overexpression of the Oncogenes c-MYC and Pim-1 in Multiple Tissues," Genesis 44:447-453 (2006).
Rosenwald et al., "Increased expression of eukaryotic translation initiation factors eIF-4E and eIF-2alpha in response to growth induction by c-myc," PNAS USA 90:6175-6178 (1993).
Sauer, "Inducible Gene Targeting in Mice Using the Cre/lox System," Methods, (1998), vol. 14, No. 4, pp. 381-392.
Schiedlmeier et al., "High-level Ectopic HOXB4 Expression Confers a Profound in Vivo Competitive Growth Advantage on Human Cord Blood CD34 Cells, but Impairs Lymphomyeloid Differentiation", Blood, vol. 101, No. 5, Mar. 1, 2003, pp. 1759-1768.
Schmidt, et al., "Transgenic mice bearing the human c-myc gene activated by an immunoglobulin enhancer: A pre-B-cell lymphoma model," PNAS USA, (1988), 85:6047-6051.
Schroy, et al., "A Simple Method for Freezing and Thawing Cultured Cells," Methods in Cell Science (formerly known as TCA Manual), (1976), vol. 2, No. 1, pp. 309-310.
Schwarze et al., "Protein transduction: unrestricted delivery into all cells?" Trends Cell Biol. 10:290-295 (2000).
Sipione, S. et al., "Modeling brain pathologies using neural stem cells," Methods Mol. Biol., (2002), vol. 198, pp. 245-262.
Soane,L., et al., "TAT-mediated endocytotic delivery of the loop deletion Bcl-2 protein protects neurons against cell death", Journal of Neurochemistry, (2005), vol. 95, pp. 230-243.

Supplementary Search Report received for European Patent Application No. 08743862.8 mailed on Feb. 9, 2010, 1 page.
Takahashi, et al., Induction of pluripotent stem cells from mouse embryonic and adult fibroblast cultures by defined factors, Cell, 126:663-676, 2006.
Thomas, et. al., "Progress and Problems with the Use of Viral Vectors for Gene Therapy", Nature, (May 2003), vol. 4, pp. 346-358.
Tsai et al., "Lymphohematopoietic progenitors immortalized by a retroviral vector harboring a dominant-negative retinoic acid receptor can recapitulate lymphoid, myeloid, and erythroid development," Genes & Dev. 8:2831-2841 (1994).
Varnum-Finney et al., "Pluripotent, cytokine-dependent, hematopoietic stem cells are immortalized by constitutive Notch1 signaling," Nature Medicine 6(11):1278-1281 (2000).
Vaux et al., "Bcl-2 gene promotes haemopoietic cell survival and cooperates with c-myc to immortalize pre-B cells," Nature 335:440-442 (1988).
Wang et al., "Primitive Human Hematopoietic Cells Are Enriched in Cord Blood Compared with Adult Bone Marrow or Mobilized Peripheral Blood as Measured by the Quantitative in Vivo SCID-Repopulating Cell Assay," Blood 89:3919-3924 (1997).
Wikipedia [online], "Stem Cell", 2008, [retrieved on Nov. 13, 2008]. Retrieved from the Internet: <URL: http//en.wikipedia.org/wiki/Stem_cell>, 11 pages.
Wilson, et al., "c-Myc controls the balance between hematopoietic stem cell self-renewal and differentiation", Genes and Development, 2004, vol. 18, pp. 2747-2763.
Wurm, et al., "Large-scale transient expression of mammalian cells for recombinant protein production," Curr. Op. Biotech., (1999), vol. 10, pp. 156-159.
Yagihashi, et al., "Detection of Anti-Survivin Antibody in Gastrointestinal Cancer Patients", Clinical Chemistry,. (2001), vol. 47, No. 9, pp. 1729-1731.
Yanai et al., "A novel stromal cell-dependent hematopoietic cell line established from temperature-sensitive SV40 T-antigen transgenic mice," Exp. Hematol., 27:1087-1096 (1999).
Young et al., "B-Cell Receptor Signaling in the Genesis and Maintenance of B-Cell Lymphoma", Future Oncology, vol. 4, No. 5, 2008, pp. 591-594.
Zhang et al., "Cytokines Regulating Hematopoietic Stem Cell Function", Current Opinion Hematology, vol. 15, No. 4, Jul. 2008, pp. 307-311.
English Translation of Office Action on Korean Patent Application No. 10-2013-7020078 dated Sep. 17, 2014, 5 pages.
Examination Report on Canadian Application No. 2,735,522 dated Oct. 2, 2014, 2 pages.
Final Office Action on U.S. Appl. No. 12/506,894 dated Oct. 9, 2014, 15 pages.
Miharada et al., "Efficient enucleation of erythroblasts differentiated in vitro from hematopoietic stem and progenitor cells", Nature Biotechnology, 24(10): 1255-1256, 2006.
Official Communication issued on European Patent Application 09810692.5, mailed Oct. 22, 2014.
English Translation of Decision of Rejection on Japanese Application No. 2011-520133, mail date Nov. 26, 2014, 6 pages.
English Translation of Decision of Rejection on Japanese Application No. 2011-525258, mail date Dec. 3, 2014, 11 pages.
Examiners Report on Canadian Application No. 2680613 dated Nov. 28, 2014, 4 pages.
Final Office Action on U.S. Appl. No. 12/701383 dated Nov. 13, 2014, 18 pages.
Notice of Allowance on U.S. Appl. No. 12/467,957, mailed Nov. 26, 2014, 7 pages.
Official Action on European Application No. 09810692.5 dated Oct. 22, 2014, 3 pages.
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
English Translation of Office Action on Israeli Patent Application No. 200919 dated May 19, 2014, 3 pages.

(56) References Cited

OTHER PUBLICATIONS

Extended European Search Report for EP Patent Application No. 13188850.0, dated May 27, 2014, 8 pages.
Notice of Allowance on U.S. Appl. No. 13/777,967 dated Jul. 14, 2014, 56 pages.
International Search Report and Written Opinion for International Application No. PCT/US2013/051384, mail date Nov. 13, 2013, 15 pages.
Johnson, N.A. et al., "Lymphomas with concurrent BCL2 and MYC translocations: the critical factors associated with survival", Blood, 2009, vol. 114, No. 11, pp. 2273-2279.
Levesque, J-p. et al., "The endosteal 'osteoblastic' niche and its role in hematopoietic stem cell homing and mobilization", Leukemia, 2010, vol. 24, pp. 1979-1992.
Wilson A., et al., c-Myc controls the balance between hematopoietic stem cell self-renewal and differentiation. Genes Dev. 18:2747-63 (2004).
Examiners Report on European Application No. 12187097.6 dated Jan. 22, 2015, 6 pages.
International Preliminary Report on Patentability for International Application No. PCT/US2013/051384, mail date Jan. 29, 2015, 12 pages.
International Preliminary Report and Written Opinion for International Application No. PCT/US2014/022971, mail date Sep. 24, 2015.
International Preliminary Report on Patentability issued on PCT/US2014/022977, issued Sep. 15, 2015.
Non-Final Office Action on U.S. Appl. No. 14/661786, mailed Aug. 27, 2015.
Notice of Reasons for Rejection (English translation) issued on Japanese application 2014-108137, mailed Aug. 18, 2015.
Office Action issued on Australian Application 2014249202, mailed Nov. 18, 2015.
Office Action issued on Canadian Application 2731767, mailed Oct. 5, 2015.
Office Action issued on Canadian Application 2735522, mailed Nov. 16, 201.
Xu Zhixiang, et al, "The Development of the Study On the Anti-Tumor Effect of Flt3 Ligand," Chinese Journal of Tumor Biological Therapy, vol. 7, No. 3, Sep. 30, 2000.
Extended Search Report issued on European Patent Application 15175802.6, mailed Dec. 14, 2015.
First Office Action issued on Chinese Application 201410479685.2, mailed Nov. 17, 2015.

* cited by examiner

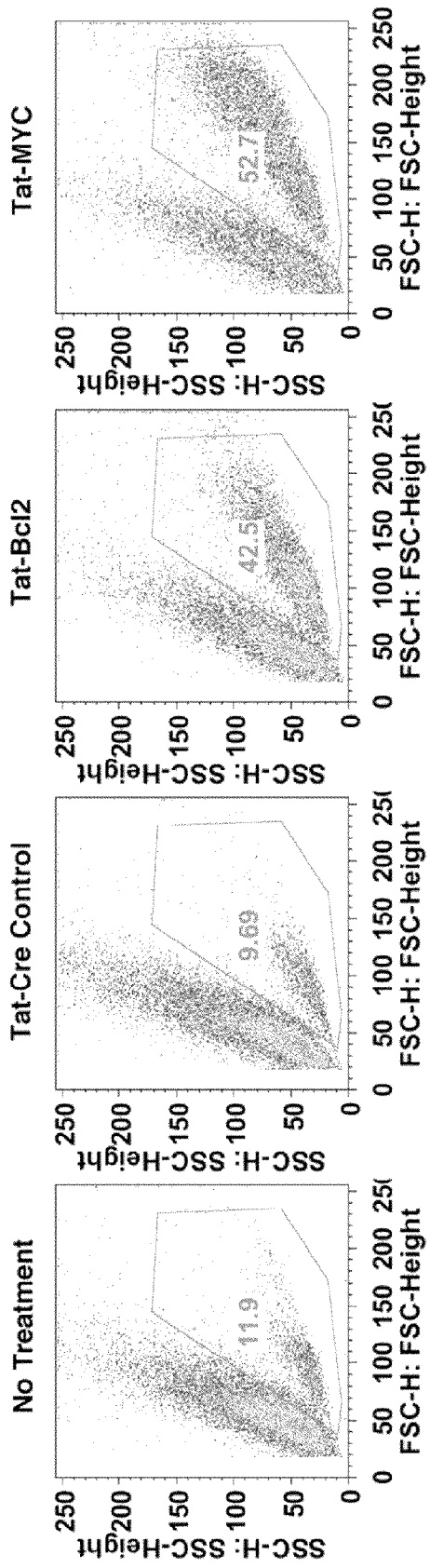

Bone Marrow from NOG transplanted with 5x10^6 FCB84 cultured for 13 days with and without TMTB in the media

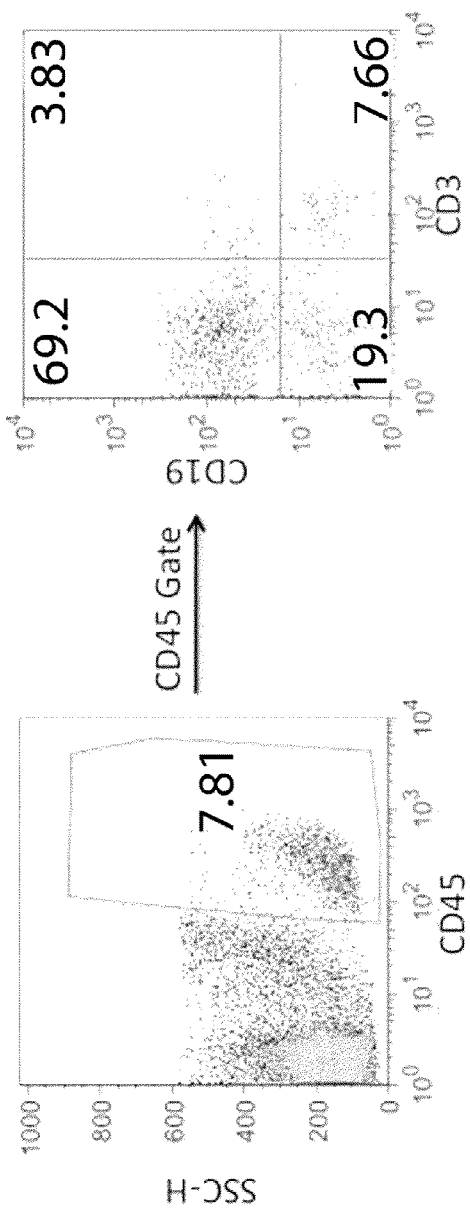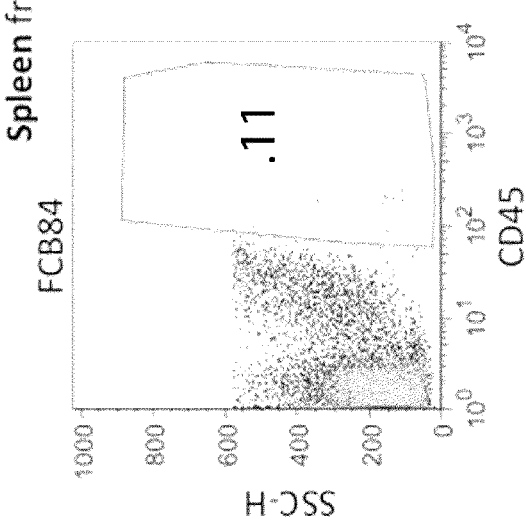
FIG. 13

Tat-MYC Amino Acid sequence

MRKKRRQRRRMPLNVSFTNRNYDLDYDSVQPYFYCDEEENFYQQQQQSELQPPAPSEDIWKKFELLPTPPLSPSRRSGLCSPS
YVAVTPFSLRGDNDGGGSFSTADQLEMVTELLGGDMVNQSFICDPDDETFIKNIIIQDCMWSGFSAAAKLVSEKLASYQAAR
KDSGSPNPARGHSVCSTSSLYLQDLSAAASECIDPSVVFPYPLNDSSSPKSCASQDSSAFSPSSDSLLSSTESSPQGSPEPLV
LHEETPPTTSSDSEEQEDEEEIDVVSVEKRQAPGKRSESGSPSAGGHSKPPHSPLVLKRCHVSTHQHNYAAPPSTRKDYPAA
KRVKLDSVRVLRQISNNRKCTSPRSSDTEENVKRRTHNVLERQRRNELKRSFFALRDQIPELENNEKAPKVVILKKATAYILS
VQAEEQKLISEEDLLRKRREQLKHKLEQLRKGELNSKLEGKPIPNPLLGLDSTRTGHHHHHH      (SEQ ID NO: 1)

Amino acids 2-10 are the HIV Tat protein transduction domain
Amino acids 11-454 are c-MyC
Amino acids 455-468 are the 14 amino acid V5 epitope
Amino acids 472-477 are the 6 Histidine tag

FIG. 15A

Tat-MYC Nucleotide sequence

ATGAGGAAGAAGCGGAGACAGCGACGAAGAATGCCCCTCAACGTTAGCTTCACCAACAGAGAACTATGACCTGACTACGACTCGGTGCA
GCCGTATTTCTACTGCGACGAGGAGGAGAACTTCTACCAGCAGCGAGCTGCAGCCCCGGCCCCTACGTTGCGTGAGGATATCT
GAAGAAATTCGAGCTGCTGCCACCCCGGCCCACGCCGCTCCGGCTCTGCTGCTCCGGCTCCGGCCCCTACGTTGCGTCACACCC
TTCTCCCTTCGGGAGACAAGACGCGGTGCCACCAGCTTCTCCACGCCGGGAGCTTCTCCACAGCTGGAGATGTGACCGAGCTGCTGGGAGGAGA
CATGGTGAACCAGAGTTTCATCTGCGAACCCGGAGAACCTTCATCGAGACCTTCATCAGGACCTGTATGTGGAGCGGCTTCT
CGGCCGCCGCCAAGCTCGTCTCAGAGAAGCTGGCCTTCACCAGCTGCGCGCAAAGACAGCGGCAAAGACAGCGGCAACCCCGGCCCAC
AGCGTCTGCTCCACCTCCAGCTTGTACCTGAGGATCTCTGAGCGCCTGAGACTCCTCGGAGTGCATCGACCCTCGGATTCTCTCCTCGACGG
TCTCAACGACAGCAGCTCGCCCAAGCTCCCCGAGCCCTGGCTGCTCCATGAGGAGGCAGGCTCCTGGCAAAAGGTTCAGAGTCTGAGGAACAAGAA
AGTTCCTCCCCAGGGCAGCCCCGAGCCCTGGCTGTTTCTGTGGAAAAGAGGCAGGCTCCTGGCAAAAGGTTCAGAGTCTGATCACCTTCTGCTGGAGGCCA
GATGAGGAAGAAATCGATGTTGTTTCTGTGGAAAAGAGGCAGGCTCCTGGCAAAAGGTTCAGAGTCTGATCACCTTCTGCTGGAGGCCA
CAGCAAACCTCCTCACAGCCCACTGGTCCTCAAGAGGTGCCACGTCAGAGTCAGAGCATCAGCAGCGCCTCCTCCCTCCACTCGGA
AGGACTATCCTGCTGCCAAGAGGTCAAGTTGGACAGTGACAGTGTCAGAGTCTTGGAGCGCCAGAGGAGAACGAGCTAAAACGAGCTTTTTGC
TCCTCGGACACCGAGGAGAATGTCAAGAGGCGAACAATGAAAAGGCCCCCAAGTTAATCTTAAAAAGCCACAGCAGCATCCTGTCCG
CCTGCGTGACCAGATCCCGGAGTTGGAAAACAATGAAAAGGCCCCCAAGTTAATCTTAAAAAGCCACAGCAGCATCCTGTCCG
TCCAAGCAGAGGAGCAAAAGCTCATTTCTGAAGAGGACTTGTTGCGGAAACAGTTGAAACACAAACTTGAACAGCTACGG
AAGGGCGAGCTCAATTCGAAGCTTGAAGGTAAGCCTATCCCCTAACCCTCCTCCGATTCTCTACGCGTACCGTCATCATCACCA
TCACCATTGA (SEQ ID NO: 2)

FIG. 15A (CONT.)

Tat-Bcl2Δ Amino Acid sequence

MRKKRRQRRRMAHAGRSGYDNREIVMKYIHYKLSQRATSGISIEAAGPALSPVPPVVHLTLRQAGDDFSRRYRRDFAEMSSQL
HLTPFTARGCFATVVEELFRDGVNWGRIVAFFEFGGVMCVESVNREMSPLVDNIALWMTEYLNRHLHTWIQDNGGWDAFVELY
GPSMRPLFDFSWLSLKTLLSLALVGACITLGAYLSHKGELNSKLEGKPIPNPLLGLDSTRTGHHHHHH (SEQ ID NO: 3)

Amino acids 2-10 are the HIV Tat protein transduction domain
Amino acids 11-212 are Bcl2Δ
Amino acids 213-226 are the 14 amino acid V5 epitope
Amino acids 230-235 are the 6 Histidine tag Tat-Bcl2Δ Nucleotide sequence atgaggaagaagcggagacagcgacgagaagaatggcgcacgctgggagagaatggttacgataaccgggagatagtgatgaagta
catccattataagctgtccagagggctacgagtgtcgcgcgcgccagccaggccggggcgcgggggcctgcgattctctcccgcgaccgcggg
tggtccacctgacccctgaccctcgcccttgcccaccgcgcggatgcttgccacggtgtgcacacctgcttcaggaagctcttcagggacg
cacctgacgccctcttgagttgagtgactgaggtcatgtgtgtgcacaccctgctgttctcctggctgctcagttgcctctgtgtgggagcttgcat
ggcccccagcatgcgcctatctgagcgccaacaagggcgagctcagttgaagcttgaagctaagcctatccctaaccctctctctcg
gtctcgattctacgcgtaccggtcatcatcaccattga (SEQ ID NO: 4)

FIG. 15B

```
                        SEQUENCE LISTING

<160> NUMBER OF SEQ ID NOS: 6

<210> SEQ ID NO 1
<211> LENGTH: 477
<212> TYPE: PRT
<213> ORGANISM: Artificial Sequence
<220> FEATURE:
<223> OTHER INFORMATION: Fusion protein

<400> SEQUENCE: 1

Met Arg Lys Lys Arg Arg Gln Arg Arg Met Pro Leu Asn Val Ser
1               5                   10                  15

Phe Thr Asn Arg Asn Tyr Asp Leu Asp Tyr Asp Ser Val Gln Pro Tyr
                20                  25                  30

Phe Tyr Cys Asp Glu Glu Glu Asn Phe Tyr Gln Gln Gln Gln Gln Ser
            35                  40                  45

Glu Leu Gln Pro Pro Ala Pro Ser Glu Asp Ile Trp Lys Lys Phe Glu
    50                  55                  60

Leu Leu Pro Thr Pro Pro Leu Ser Pro Ser Arg Arg Ser Gly Leu Cys
65                  70                  75                  80

Ser Pro Ser Tyr Val Ala Val Thr Pro Phe Ser Leu Arg Gly Asp Asn
                85                  90                  95

Asp Gly Gly Gly Gly Ser Phe Ser Thr Ala Asp Gln Leu Glu Met Val
            100                 105                 110

Thr Glu Leu Leu Gly Gly Asp Met Val Asn Gln Ser Phe Ile Cys Asp
        115                 120                 125

Pro Asp Asp Glu Thr Phe Ile Lys Asn Ile Ile Ile Gln Asp Cys Met
    130                 135                 140

Trp Ser Gly Phe Ser Ala Ala Ala Lys Leu Val Ser Glu Lys Leu Ala
145                 150                 155                 160

Ser Tyr Gln Ala Ala Arg Lys Asp Ser Gly Ser Pro Asn Pro Ala Arg
                165                 170                 175

Gly His Ser Val Cys Ser Thr Ser Ser Leu Tyr Leu Gln Asp Leu Ser
            180                 185                 190

Ala Ala Ala Ser Glu Cys Ile Asp Pro Ser Val Val Phe Pro Tyr Pro
        195                 200                 205

Leu Asn Asp Ser Ser Ser Pro Lys Ser Cys Ala Ser Gln Asp Ser Ser
    210                 215                 220

Ala Phe Ser Pro Ser Ser Asp Ser Leu Leu Ser Ser Thr Glu Ser Ser
225                 230                 235                 240

Pro Gln Gly Ser Pro Glu Pro Leu Val Leu His Glu Glu Thr Pro Pro
                245                 250                 255

Thr Thr Ser Ser Asp Ser Glu Glu Glu Gln Glu Asp Glu Glu Glu Ile
            260                 265                 270
```

```
Asp Val Val Ser Val Glu Lys Arg Gln Ala Pro Gly Lys Arg Ser Glu
            275                 280                 285

Ser Gly Ser Pro Ser Ala Gly Gly His Ser Lys Pro Pro His Ser Pro
        290                 295                 300

Leu Val Leu Lys Arg Cys His Val Ser Thr His Gln His Asn Tyr Ala
305                 310                 315                 320

Ala Pro Pro Ser Thr Arg Lys Asp Tyr Pro Ala Ala Lys Arg Val Lys
                325                 330                 335

Leu Asp Ser Val Arg Val Leu Arg Gln Ile Ser Asn Asn Arg Lys Cys
            340                 345                 350

Thr Ser Pro Arg Ser Ser Asp Thr Glu Glu Asn Val Lys Arg Arg Thr
        355                 360                 365

His Asn Val Leu Glu Arg Gln Arg Arg Asn Glu Leu Lys Arg Ser Phe
    370                 375                 380

Phe Ala Leu Arg Asp Gln Ile Pro Glu Leu Glu Asn Asn Glu Lys Ala
385                 390                 395                 400

Pro Lys Val Val Ile Leu Lys Lys Ala Thr Ala Tyr Ile Leu Ser Val
                405                 410                 415

Gln Ala Glu Glu Gln Lys Leu Ile Ser Glu Glu Asp Leu Leu Arg Lys
            420                 425                 430

Arg Arg Glu Gln Leu Lys His Lys Leu Glu Gln Leu Arg Lys Gly Glu
        435                 440                 445

Leu Asn Ser Lys Leu Glu Gly Lys Pro Ile Pro Asn Pro Leu Leu Gly
    450                 455                 460

Leu Asp Ser Thr Arg Thr Gly His His His His His His
465                 470                 475

<210> SEQ ID NO 2
<211> LENGTH: 1434
<212> TYPE: DNA
<213> ORGANISM: Artificial Sequence
<220> FEATURE:
<223> OTHER INFORMATION: Fusion protein

<400> SEQUENCE: 2
atgaggaaga agcggagaca gcgacgaaga atgccctca acgttagctt caccaacagg      60
aactatgacc tcgactacga ctcggtgcag ccgtatttct actgcgacga ggaggagaac    120
ttctaccagc agcagcagca gagcgagctg cagcccccgg cgcccagcga ggatatctgg    180
aagaaattcg agctgctgcc caccccgccc ctgtccccta gccgccgctc cgggtctgc    240 tcgccctcct acgttgcggt cacacccttc tccttcgggg agacaacga cggcggtggc    300 gggagcttct ccacggccga ccagctggag atggtgaccg agctgctggg aggagacatg    360
gtgaaccaga gtttcatctg cgacccggac gacgagacct tcatcaaaaa catcatcatc    420
caggactgta tgtggagcgg cttctcggcc gccgccaagc tcgtctcaga gaagctggcc    480
tcctaccagg ctgcgcgcaa agacagcggc agcccgaacc cgcccgcgg ccacagcgtc    540 tgctccacct ccagcttgta cctgcaggat ctgagcgccg ccgcctcaga gtgcatcgac    600
ccctcggtgg tcttcccta ccctctcaac gacagcagct cgcccaagtc ctgcgcctcg    660
caagactcca gcgccttctc tccgtcctcg gattctctgc tcctcgac ggagtcctcc    720 ccgcagggca gccccgagcc cctggtgctc atgaggaga caccgccac accagcagc    780 gactctgagg aggaacaaga agatgaggaa gaaatcgatg ttgtttctgt ggaaaagagg    840
caggctcctg gcaaaaggtc agagtctgga tcaccttctg ctggaggcca cagcaaacct    900
```

```
cctcacagcc cactggtcct caagaggtgc cacgtctcca cacatcagca caactacgca   960
gcgcctccct ccactcggaa ggactatcct gctgccaaga gggtcaagtt ggacagtgtc  1020
agagtcctga gacagatcag caacaaccga aaatgcacca gccccaggtc ctcggacacc  1080
gaggagaatg tcaagaggcg aacacacaac gtcttggagc gccagaggag gaacgagcta  1140
aaacggagct tttttgccct gcgtgaccag atcccggagt tggaaaacaa tgaaaaggcc  1200
cccaaggtag ttatccttaa aaaagccaca gcatacatcc tgtccgtcca agcagaggag  1260
caaaagctca tttctgaaga ggacttgttg cggaaacgac gagaacagtt gaaacacaaa  1320
cttgaacagc tacggaaggg cgagctcaat tcgaagcttg aaggtaagcc tatccctaac  1380
cctctcctcg gtctcgattc tacgcgtacc ggtcatcatc accatcacca ttga        1434
```

<210> SEQ ID NO 3
<211> LENGTH: 235
<212> TYPE: PRT
<213> ORGANISM: Artificial Sequence
<220> FEATURE:
<223> OTHER INFORMATION: Fusion protein

<400> SEQUENCE: 3

```
Met Arg Lys Lys Arg Arg Gln Arg Arg Met Ala His Ala Gly Arg
 1               5                  10                  15

Ser Gly Tyr Asp Asn Arg Glu Ile Val Met Lys Tyr Ile His Tyr Lys
                20                  25                  30

Leu Ser Gln Arg Ala Thr Ser Gly Ile Ser Ile Glu Ala Ala Gly Pro
            35                  40                  45

Ala Leu Ser Pro Val Pro Pro Val Val His Leu Thr Leu Arg Gln Ala
        50                  55                  60

Gly Asp Asp Phe Ser Arg Arg Tyr Arg Arg Asp Phe Ala Glu Met Ser
65                  70                  75                  80

Ser Gln Leu His Leu Thr Pro Phe Thr Ala Arg Gly Cys Phe Ala Thr
                85                  90                  95

Val Val Glu Glu Leu Phe Arg Asp Gly Val Asn Trp Gly Arg Ile Val
            100                 105                 110

Ala Phe Phe Glu Phe Gly Gly Val Met Cys Val Glu Ser Val Asn Arg
        115                 120                 125

Glu Met Ser Pro Leu Val Asp Asn Ile Ala Leu Trp Met Thr Glu Tyr
    130                 135                 140

Leu Asn Arg His Leu His Thr Trp Ile Gln Asp Asn Gly Gly Trp Asp
145                 150                 155                 160

Ala Phe Val Glu Leu Tyr Gly Pro Ser Met Arg Pro Leu Phe Asp Phe
                165                 170                 175

Ser Trp Leu Ser Leu Lys Thr Leu Leu Ser Leu Ala Leu Val Gly Ala
            180                 185                 190

Cys Ile Thr Leu Gly Ala Tyr Leu Ser His Lys Lys Gly Glu Leu Asn
        195                 200                 205

Ser Lys Leu Glu Gly Lys Pro Ile Pro Asn Pro Leu Leu Gly Leu Asp
    210                 215                 220

Ser Thr Arg Thr Gly His His His His His
225                 230                 235
```

<210> SEQ ID NO 4
<211> LENGTH: 708
<212> TYPE: DNA
<213> ORGANISM: Artificial Sequence

```
<220> FEATURE:
<223> OTHER INFORMATION: Fusion protein

<400> SEQUENCE: 4
atgaggaaga agcggagaca gcgacgaaga atggcgcacg ctgggagaag tggttacgat      60
aaccgggaga tagtgatgaa gtacatccat tataagctgt cgcagagggc tacgagtggg     120
atctcgatcg aggccgcggg gcctgcgctc agcccggtgc cacctgtggt ccacctgacc     180
ctccgccagg ccggcgacga cttctcccgc cgctaccgcc gcgacttcgc cgagatgtcc     240
agccagctgc acctgacgcc cttcaccgcg cggggatgct ttgccacggt ggtggaggag     300
ctcttcaggg acggggtgaa ctgggggagg attgtggcct tctttgagtt cggtgggtgtc    360 atgtgtgtgg agagcgtcaa ccgggagatg tcgcccctgg tggacaacat cgccctgtgg    420
atgactgagt acctgaaccg gcacctgcac acctggatcc aggataacgg aggctgggat    480
gcctttgtgg aactgtacgg ccccagcatg cggcctctgt ttgatttctc ctggctgtct    540
ctgaagactc tgctcagttt ggccctggtg ggagcttgca tcaccctggg tgcctatctg    600
agccacaaga agggcgagct caattcgaag cttgaaggta agcctatccc taaccctctc    660
ctcggtctcg attctacgcg taccggtcat catcaccatc accattga                 708

<210> SEQ ID NO 5
<211> LENGTH: 9
<212> TYPE: PRT
<213> ORGANISM: Artificial Sequence
<220> FEATURE:
<223> OTHER INFORMATION: TAT transduction domain from HIV

<400> SEQUENCE: 5

Arg Lys Lys Arg Arg Gln Arg Arg Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Artificial transduction domain

<400> SEQUENCE: 6

Tyr Ala Arg Ala Ala Ala Arg Gln Ala Arg Ala
1               5                   10
```

EXPANSION OF ADULT STEM CELLS IN VITRO

CROSS-REFERENCE TO RELATED APPLICATION

This application claims the benefit under 35 U.S.C. §119 to U.S. Provisional Patent Application 61/776,422, filed Mar. 11, 2013, the disclosure of which is incorporated herein by reference in its entirety.

GOVERNMENT INTEREST

This invention was made with government support under SBIR Ph II grant. 5R44HL091740-03, Proposal Title: Generation of HIV resistant cells from protein transduced hematopoetic stem cells, awarded by the National Institute of Health. The government has certain rights in the invention

REFERENCE TO SEQUENCE LISTING, TABLE, OR COMPUTER PROGRAM LISTING

The present application is being filed along with a Sequence Listing in electronic format. The Sequence Listing is provided as a file entitled Taiga002ASeqList.txt created on Mar. 11, 2013, which is 9,463 bytes in size. The information in the electronic format of the Sequence Listing is incorporated herein by reference in its entirety.

FIELD

Provided herein are embodiments that relate to long term stem cells, methods of producing such cells, and various protein constructs.

BACKGROUND

Long term hematopoietic stem cells (LT-HSCs) are rare progenitors that reside in adult bone marrow and give rise to the entire repertoire of mature blood cells. These cells are essential for the maintenance of all blood cell compartments. Stem cell transplantation can be a useful adjunct in therapy for hematologic malignancy, autoimmunity and immunodeficiency, among others.

SUMMARY

In some embodiments, a method for producing a population of conditionally immortalized adult stem cells is provided. The method can comprise providing one or more adult stem cells with an exogenously synthesized Myc polypeptide that promotes one or more of cell survival or proliferation and an exogenously synthesized Bcl-2 domain polypeptide that inhibits apoptosis. In some embodiments the Myc polypeptide is provided to the one or more adult stem cells at intervals of at least about 72 hours and the Bcl-2 domain polypeptide is provided to the one or more adult stem cells at intervals of at least about 96 hours, so as to produce a population of conditionally immortalized adult stem cells. In some embodiments, the Bcl-2 domain polypeptide and/or the Myc polypeptide are supplied no more frequently than once an hour. In some embodiments, the Bcl-2 domain polypeptide and/or the Myc polypeptide are supplied no more frequently than once every two hours. In some embodiments, the Bcl-2 domain polypeptide and/or the Myc polypeptide are supplied no more frequently than once every three hours. In some embodiments, the Bcl-2 domain polypeptide and/or the Myc polypeptide are supplied no more frequently than once every four hours. In some embodiments, the Bcl-2 domain polypeptide and/or the Myc polypeptide are supplied no more frequently than once every five hours. In some embodiments, the Bcl-2 domain polypeptide and/or the Myc polypeptide are supplied no more frequently than once every six hours. In some embodiments, the Bcl-2 domain polypeptide and/or the Myc polypeptide are supplied no more frequently than once every seven hours. In some embodiments, the Bcl-2 domain polypeptide and/or the Myc polypeptide are supplied no more frequently than once every eight hours. In some embodiments, the Bcl-2 domain polypeptide and/or the Myc polypeptide are supplied no more frequently than once every nine hours. In some embodiments, the Bcl-2 domain polypeptide and/or the Myc polypeptide are supplied no more frequently than once every 10 hours. In some embodiments, the Bcl-2 domain polypeptide and/or the Myc polypeptide are supplied no more frequently than once every 11 hours. In some embodiments, the Bcl-2 domain polypeptide and/or the Myc polypeptide are supplied no more frequently than once every 12 hours. In some embodiments, the Bcl-2 domain polypeptide and/or the Myc polypeptide are supplied no more frequently than once every 13 hours. In some embodiments, the Bcl-2 domain polypeptide and/or the Myc polypeptide are supplied no more frequently than once every 14 hours. In some embodiments, the Bcl-2 domain polypeptide and/or the Myc polypeptide are supplied no more frequently than once every 15 hours. In some embodiments, the Bcl-2 domain polypeptide and/or the Myc polypeptide are supplied no more frequently than once every 16 hours. In some embodiments, the Bcl-2 domain polypeptide and/or the Myc polypeptide are supplied no more frequently than once every 17 hours. In some embodiments, the Bcl-2 domain polypeptide and/or the Myc polypeptide are supplied no more frequently than once every 18 hours. In some embodiments, the Bcl-2 domain polypeptide and/or the Myc polypeptide are supplied no more frequently than once every 19 hours. In some embodiments, the Bcl-2 domain polypeptide and/or the Myc polypeptide are supplied no more frequently than once every 20 hours. In some embodiments, the Bcl-2 domain polypeptide and/or the Myc polypeptide are supplied no more frequently than once every 21 hours. In some embodiments, the Bcl-2 domain polypeptide and/or the Myc polypeptide are supplied no more frequently than once every 22 hours. In some embodiments, the Bcl-2 domain polypeptide and/or the Myc polypeptide are supplied no more frequently than once every 23 hours. In some embodiments, the Bcl-2 domain polypeptide and/or the Myc polypeptide are supplied no more frequently than once every 24 hours. In some embodiments, the Bcl-2 domain polypeptide and/or the Myc polypeptide are supplied no more frequently than once every 36 hours. In some embodiments, the Bcl-2 domain polypeptide and/or the Myc polypeptide are supplied no more frequently than once every 48 hours.

In some embodiments, a Myc fusion protein is provided. The fusion protein comprises a protein transduction domain, a Myc polypeptide that promotes one or more of cell survival or proliferation, a V5 domain, and a six histidine epitope tag.

In some embodiments, a stem cell expansion media is provided. The expansion media comprises IL3, IL6, stem cell factor, thrombopoeitin, Flt3-L, and GM-CSF.

In some embodiments, a Myc fusion protein is provided. The Myc fusion protein comprises a protein transduction domain, a Myc polypeptide that promotes one or more of cell survival or proliferation. The Myc fusion protein half-life is longer than about 60 minutes.

In some embodiments, a nucleic acid encoding any of the proteins disclosed herein is provided.

In some embodiments, a vector comprising any of the nucleic acids provided herein is provided.

In some embodiments, a cell comprising any of the vectors or nucleic acids provided herein is provided.

DETAILED DESCRIPTION OF THE DRAWINGS

The features of various embodiments are set forth with particularity in the appended claims. A better understanding of the features and advantages of some of the present embodiments will be obtained by reference to the following detailed description that sets forth illustrative embodiments, in which the principles of the various embodiments are utilized, and the accompanying drawings of which:

FIGS. 1A, 1B, 1C, 1D, and 1E show an illustrative embodiment of the generation and in vitro characterization of Tat fusion proteins. FIG. 1A shows an illustrative embodiment of a graphic representation of Tat-Myc and Tat-Bcl-2 fusion proteins including the location of the in frame protein transduction domain of HIV-1 Tat and the V5 and 6×His tags.

FIG. 1B shows an illustrative embodiment of the recombinant proteins following purification from $E.\ coli$, separation by SDS-PAGE, and staining with Coomassie. FIG. 1C shows an illustrative embodiment of a lawn of confluent 3T3 cells exposed to purified recombinant Tat-Myc, Tat-Bcl-2, or left untreated (NT) for two hours, and then fixed and stained with a monoclonal antibody to V5 and with a Hoechst 9934 nuclear stain. The Tat-Myc protein largely localized to the nuclear region in this timeframe, whereas the Tat-Bcl-2 remained in the cytoplasmic and perinuclear space. FIG. 1D shows an illustrative embodiment of a SDS-PAGE and western blot analysis (monoclonal antibodies to V5 and β-actin) of human cord blood derived HSCs pulsed with a single exposure of Tat-Myc for 1 hours, washed, and then lysed (at the indicated time points) to separate the plasma membrane and cytoplasmic fraction from the nuclear fraction. FIG. 1E shows an illustrative embodiment of a SDS-PAGE and western blot analysis (monoclonal antibodies to V5 and β-actin) of the nuclear fraction of human cord blood derived HSCs pulsed with a single exposure of Tat-Myc for 2 hours, washed, and then lysed (at the indicated time points) to separate the plasma membrane and cytoplasmic fraction from the nuclear fraction. The bulk of the protein is lost between 24 and 48 hours. There is no detectable protein left at any point after 72 hours.

FIGS. 2A, 2B, 2C, and 2D show an illustrative embodiment of a graphical representation showing that recombinant Tat-Myc and Tat-Bcl-2 are biologically active. FIGS. 2A and 2B show an illustrative embodiment of a graphical representation of in vitro activated T-cells replated for 48 hours in media alone (no treatment, NT), media supplemented with Tat-Cre (Tat-Control, TC), or increasing concentrations of either Tat-Myc (TM) (FIG. 2A), or Tat-Bcl-2 (TB) (FIG. 2B). The frequency of live cells in the starting population of cells is also shown (light gray bars). FIGS. 2C and 2D show an illustrative embodiment of a graphical representation of activated T-cells further incubated with Tat-Myc and labeled with CFSE showing that the activated T-cells retain a blasting phenotype (FIG. 2C), and continue to proliferate after the antigenic stimulation and exogenously added cytokines were removed (FIG. 2D).

FIGS. 3A, 3B, and 3C show an illustrative embodiment of a graphical representation of the expansion of murine HSCs in vitro with Tat-Myc and Tat-Bcl-2. FIG. 3A shows an illustrative embodiment of graphs of FACS analysis of the resulting cell population having a phenotype of c-Kit+, Sca-1+, and negative for lineage markers (Mac-1, Gr-1, B220, CD3, Ter-119, and Flk-2). FIG. 3B shows an illustrative embodiment of a graphical representation of the proliferation of HSCs in vitro when cultured with Tat-Myc and Tat-Bcl-2 (Dark Gray, left most trace), as compared with HSCs in culture without added Tat-fusion proteins (light gray, right-most trace). FIG. 3C shows an illustrative embodiment of a graphical representation of the kinetics of in vitro cell expansion in cultures with Tat-Myc and Tat-Bcl-2.

FIGS. 4A, 4B, 4C, and 4D show an illustrative embodiment of a graphical representation of the functional analysis of Tat-Myc and Tat-Bcl-2-expanded murine ptlt-HSCs in vivo. Cohorts of sublethally irradiated Rag-1$^{-/-}$ mice were given 10$^3$ ptlt-HSCs derived from bone marrow cells obtained from wild type C57BL/6J mice. FIG. 4A shows an illustrative embodiment of a graphical representation of a FACS analysis (CD19/B220 expression) of the presence of mature B-cells (second panel) in the peripheral blood from ptlt-HSC chimaeric mice as compared to the Rag-1$^{-/-}$ control (first panel). FIG. 4B shows an illustrative embodiment of a graphical representation of a FACS analysis (TCRβ/CD4 expression) of the presence of mature T-cells in the peripheral blood of Rag-1$^{-/-}$ ptlt-HSC chimaeric mice (second panel) as compared to the Rag-1$^{-/-}$ control (first panel). FIG. 4C shows an illustrative embodiment of a graphical representation of a FACS analysis (CD19/IgM and CD8/CD4 expression) of developing T and B-cells in lymphoid organs (spleen, thymus, lymph node, and bone marrow) from Rag-1$^{-/-}$ ptlt-HSC chimaeric mice. FIG. 4D displays data demonstrating that mature lymphoid cells were able to blast and undergo cell division following activation through their antigen receptors.

FIGS. 5A, 5B, 5C, 5D, and 5E show an illustrative embodiment of a graphical representation of the expansion of human cord blood cell-derived HSCs with Tat-Myc and Tat-Bcl-2. FIG. 5A shows an illustrative embodiment of a graphical representation of a FACS analysis of the surface phenotype of the human cord blood cells expanded in vitro for 14 days (Top panels cytokine cocktail only; Bottom panels cytokine cocktail supplemented with Tat-Myc and Tat-Bcl-2). FIG. 5B shows an illustrative embodiment of a graphical representation of the kinetics of CD34+ cells expansion in vitro under both sets of conditions. FIG. 5C shows an illustrative embodiment of the images of three different colony types developed in methylcellulose assays under conditions that support myeloerythroid differentiation, derived from human ptlt-HSCs. FIG. 5D shows an illustrative embodiment of a graphical representation of the quantification of each colony type that was observed in methylcellulose cultures seeded with either 10$^3$ cord blood cells cultured with a cytokine cocktail (FCB), 10$^3$ cord blood cells cultured with a cytokine cocktail supplemented with Tat-Myc and Tat-Bcl-2 (FCB+TMTB), or 10$^4$ fresh un-manipulated cord blood cells (10^4 Fresh FCB). FIG. 5E shows an illustrative embodiment of a graphical representation of the quantification of the number of colonies observed in methylcellulose cultures upon replating of the cells shown in FIG. 5D.

FIGS. 6A, 6B, 6C, 6D, 6E, 6F, and 6G show an illustrative embodiment of a graphical representation of the functional analysis of human cord blood derived protein-transduced long term (ptlt)-HSC in vivo. FIG. 6A shows an illustrative embodiment of a graphical representation of a FACS analysis of the bone marrow of cohorts of sublethally irradiated NSG mice given transplants of 10$^6$ cord blood cells expanded in vitro in a cocktail of cytokines (first panel; FCB), or expanded in a cocktail of cytokines supplemented with Tat-Myc and Tat-Bcl-2 (second panel; FCB TMTB), or 5×10$^6$ fresh un-manipulated cord blood cells (third panel; Fresh FCB). FIG. 6B shows an illustrative embodiment of a graphical representation of a FACS analysis of bone marrow, spleen and thymus cells from the xenochimaeric mice. All cells were stained for human CD45. Gating on CD45+ cells showed human CD34+ CD38lo cells in the bone marrow (first panel; BM); human CD19+ and human CD3+ lymphocytes in the spleen (second panel; spleen); and human CD3+ cells in the thymus (third panel; thymus). FIG. 6C shows an illustrative embodiment of a graphical representation of a FACS analysis of human splenic B-cells labeled with CFSE and cultured in the presence of monoclonal antibodies to human CD40 and IgM. Human B-cells that developed in NSG xenochimaeric mice underwent proliferation following stimulation of their antigen receptor. FIG. 6D shows an illustrative embodiment of a graphical representation of the quantification of myeloerythroid colonies from human CD34+ CD38$^{lo}$ cells obtained from the bone marrow of NSG xenochimaeric mice and plated on methycellulose. FIG. 6E shows an illustrative embodiment of a graphical representation of the quantification of the development of myeloerythroid colonies following replating. FIG. 6F shows an illustrative embodiment of a graphical representation of the quantification of myeloid and lymphoid cell differentiation (CD11b, CD33, CD3, and CD19 expression) in the CD45 positive population of bone marrow cells expanded in vitro in a cocktail of cytokines (open circles) or a cocktail of cytokines supplemented with Tat-Myc and Tat-Bcl-2 (black squares). FIG. 6G shows an illustrative embodiment of a graphical representation of the quantification of myeloid and lymphoid cell differentiation (CD11b, CD33, CD3, and CD19 expression) in the CD45 positive population of spleen cells expanded in vitro in a cocktail of cytokines (open circles) or a cocktail of cytokines supplemented with Tat-Myc and Tat-Bcl-2 (black squares).

FIGS. 7A, 7B, 7C, 7D, 7E, 7F and 7G show an illustrative embodiment of a graphical representation of the expansion of adult human G-CSF mobilized HSCs in vitro with Tat-Myc and Tat-Bcl-2. FIG. 7A shows an illustrative embodiment of a graphical representation of the surface phenotype of human CD45+ cells showing an enrichment of the human CD34+ and CD38+ fraction. FIG. 7B shows an illustrative embodiment of a graphical representation of the kinetics of cell expansion in vitro over 18 days in culture in the presence of Tat-Myc and Tat-Bcl-2. FIG. 7C shows an illustrative embodiment of a graphical representation showing that $5 \times 10^3$ human adult G-CSF HSCs, expanded in vitro with Tat-Myc and Tat-Bcl-2, gave rise to 4 morphologically distinct colony types in methylcellulose. FIG. 7D shows an illustrative embodiment of a graphical representation of FACS analysis showing that human adult G-CSF HSCs expanded in vitro with Tat-Myc and Tat-Bcl-2 gave rise to human hematopoietic lineages in xenochimaeric NSG mice. Bone marrow was from NSG mice transplanted ptlt-HSCs expanded with a cytokine cocktail supplemented with Tat-Myc and Tat-Bcl-2 (first panel; G-CSF+TMTB) or with fresh un-manipulated cord blood cells (second panel; Fresh FCB). FIG. 7E shows an illustrative embodiment of a graphical representation of FACS analysis of cells from bone marrow, spleen, and thymus. Bone marrow cells included human CD45 cells that were also human CD34+ and CD38+ (first panel), spleen cells included human CD45 cells that also stained for human CD3 (second panel), and thymus cells included human CD45 cells as well as CD3 (third panel). FIGS. 7F and 7G show an illustrative embodiment of a graphical representation of a cohort of xenochimaeric mice engrafted with $10^6$ G-CSF mobilized cells expanded in vitro in a cocktail of cytokines supplemented with Tat-Myc and Tat-Bcl-2 (black squares) were assessed for myeloid and lymphoid cell differentiation. The CD45 positive population of bone marrow cells (FIG. 7F) and spleen cells (FIG. 7G) were analyzed for CD11b, CD33, CD3, and CD19 expression.

FIG. 8 shows an illustrative embodiment of a graphical representation of a FACS analysis of mouse splenic T-cells and B-cells labeled with CFSE and cultured in the presence of monoclonal antibodies to mouse CD3 or CD40 and IgM, respectively. Mouse T-cells (light-gray left-most line, first panel) and B-cells (light-gray left-most line, second panel) that developed in Rag1−/− mice transplanted with expanded HSC from 5FU treated C57BL.6 underwent proliferation following stimulation of their antigen receptor compared to unstimulated cells (dark gray right-most line).

FIGS. 9A and 9B show an illustrative embodiment of the activity of various Myc fusion protein constructs in an activated T cell viability assay. FIG. 9A shows an illustrative diagrammatic alignment of some representative Myc fusion protein constructs. FIG. 9B shows an illustrative embodiment of a graphical representation of the percent live T cells 48 hours after treatment with representative Myc fusion protein constructs.

FIGS. 10A, 10B, 10C, and 10D show an illustrative embodiment of the activity of various Tat-fusion proteins (each at 50 ug/ml) in an activated T cell viability assay. FIG. 10A shows an illustrative embodiment of a graphical representation of the live gate from FACS analysis (forward X side scatter) for untreated cells (No treatment). FIG. 10B shows an illustrative embodiment of a graphical representation of the live gate from FACS analysis (forward X side scatter) for Tat-Cre treated cells (Tat-Cre Control). FIG. 10C shows an illustrative embodiment of a graphical representation of the live gate from FACS analysis (forward X side scatter) for Tat-Bcl2 treated cells (Tat-Bcl2). FIG. 10A shows an illustrative embodiment of a graphical representation of the live gate from FACS analysis (forward X side scatter) for Tat-Myc treated cells (Tat-Myc).

FIG. 11 shows an illustrative embodiment of a graphical representation of the number of CD34+ cells expanded in the presence of a variety of cytokines and with or without PTD fusion proteins.

FIG. 12 shows an illustrative embodiment of a graphical representation of the FACS analysis of bone marrow cells from an NSG mouse that received $5 \times 10^6$ cells expanded in FCB media alone (top panel) or FCB media supplemented with Tat-Myc and Tat-Bcl2 (lower left panel) stained for human CD45. Note the increase in human CD45+ cells in the mouse that received cells that were treated with Tat-Myc and Tat-Bcl2. The CD45+ cells were further analyzed by flow cytometry for the presence of CD34 positive cells (lower right panel).

FIG. 13 shows an illustrative embodiment of a graphical representation of the FACS analysis of the spleen cells from an NSG mouse that received $5 \times 10^6$ cells expanded in FCB media alone (top panel) or FCB media supplemented with Tat-Myc and Tat-Bcl2 (lower left panel) stained for human CD45. Note the increase in human CD45+ cells in the mouse that received cells that were treated with Tat-Myc and Tat-Bcl2. The CD45+ cells were further analyzed by flow cytometry for the presence of CD19 and CD3 positive cells (lower right panel).

FIG. 14 shows an illustrative embodiment of a graphical representation of the FACS analysis of cells from the Thymus from an NSG mouse that received $5 \times 10^6$ cells expanded in FCB media alone (top panel) or FCB media supplemented with Tat-Myc and Tat-Bcl2 (lower left panel) stained for human CD45. Note the increase in human CD45+ cells in the mouse that received cells that were treated with Tat-Myc and Tat-Bcl2. The CD45+ cells were further analyzed by flow cytometry for the presence of CD19 and CD3 positive cells (lower right panel).

FIG. 15A depicts the amino acid and nucleic acid sequences for some embodiments of the Tat-Myc polypeptide.

FIG. 15B depicts the amino acid and nucleic acid sequences for some embodiments of the Bcl-2 domain polypeptide.

DETAILED DESCRIPTION

Figure 1A:
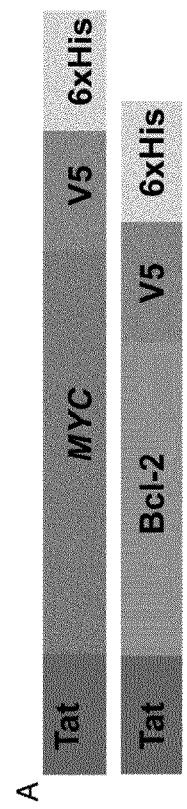

The therapeutic utility of LT-HSCs cells has been limited by their low frequency and inability to propagate them ex vivo, among other reasons. Expansion of these cells is particularly important for clinical applications such as but not limited to gene therapy.

Some embodiments described herein can be used to generate individualized HSCs for personalized medicine and other uses, optionally using autologous cells.

Some of the embodiments provided herein do not require isolation and/or purification of the CD34+ fraction prior to expansion in vitro. Thus, in some embodiments, this step can be removed from the expansion of such cells. This can reduce cost and simplify the application of this stem cell expansion approach to clinical practice. Any of the methods provided herein can, optionally, not include isolation and/or purification of the CD34+ fraction prior to expansion in vitro.

Some embodiments described herein provide an approach to expand a cytokine-dependent LT-HSC population in vitro by culturing primary adult HSCs with specific fusion proteins to produce protein-transduced long term HSCs (ptlt-HSCs). In some embodiments, the fusion proteins have a protein transduction domain linked to a proto-oncogene encoded protein or biologically active fragment or homologue thereof that induces cell survival and/or proliferation (such as a Myc polypeptide). The method can further include a fusion protein that comprises a protein transduction domain linked to an anti-apoptotic protein or biologically active fragment or functional homologue thereof (such as a Bcl-2 domain polypeptide). In some embodiments, this involves a protein transduction domain linked to a Myc polypeptide that induces cell survival and/or proliferation and a protein transduction domain linked to a Bcl-2 domain polypeptide.

GENERAL DEFINITIONS

Any methods and materials similar or equivalent to those described herein that is used in the practice of or testing of the embodiments described herein are considered to be a part of the instant disclosure.

As used herein, "stem cells (for example, hematopoietic stem cells)" refer to the term as it is generally understood in the art. For example, stem cells (for example, hematopoietic stem cells), regardless of their source, are cells that are capable of dividing and renewing themselves for long periods, are unspecialized (undifferentiated), and possess the ability to give rise to (differentiate into) specialized cell types (for example, they are progenitor or precursor cells for a variety of different, specialized cell types). In certain instances herein, "stem cells (for example, hematopoietic stem cells)" described herein refer to long term stem cells (for example, hematopoietic stem cells).

The term "long-term", when used in connection with stem cells (for example, hematopoietic stem cells), refers to the ability of stem cells (for example, hematopoietic stem cells) to renew themselves by dividing into the same non-specialized cell type over long periods (for example, 1 month, 2 months, 3 months, 4 months, 6 months, 8 months, 9 months, 12 months, 2 years, 3 years) depending on the specific type of stem cell. In some embodiments, stem cells (for example, hematopoietic stem cells) are identified by the presence of the following cell surface markers: c-kit+, Sca-1+, CD34low/−, CD38+, and/or Thy1+/low. In some embodiments, human stem cells (for example, hematopoietic stem cells) are identified by the presence of the following markers: CD34+, CD38low/−, c-kit−/low, and/or Thy1+. In some embodiments, both human and murine stem cells (for example, hematopoietic stem cells) lack cell lineage markers, such as CD2, CD3, CD4, CD5, CD8, NK1.1, B220, Ter-119, and/or Gr-1.

In some embodiments, homologues, analogues or fragments of polypeptides described herein include an amino acid sequence that is at least 40% to 100% identical, for example, at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the polypeptide.

To determine the percent homology of two amino acid sequences or of two nucleic acids, the sequences is aligned for optimal comparison purposes (for example, gaps are introduced in the sequence of a first amino acid or nucleic acid sequence for optimal alignment with a second amino acid or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (% identity=# of identical positions/total # of positions (for example, overlapping positions)×100). In some embodiments the two sequences are the same length.

To determine percent homology between two sequences, the algorithm of Karlin and Altschul (1990) Proc. Natl. Acad. Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches is performed with the NBLAST program, score=100, wordlength=12 to obtain nucleotide sequences homologous to a nucleic acid molecules described or disclose herein. BLAST protein searches is performed with the XBLAST program, score=50, wordlength=3. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (for example, XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, for example, 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, for example, 77%, 80%, 82%, 85%, 88%, 90%, 92%, 95%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. In certain instances conservative amino acid substitutions are utilized. Illustrative conservative substitution among amino acids are within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al. (1992), Proc. Natl. Acad. Sci. USA, 89:10915-10919). The BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (for example, 1, 2 or 3), while more preferred conservative amino acid substitutions are characterized by a BLOSUM62 value of at least 2 (for example, 2 or 3).

As used herein, the term "nucleic acid" refers to a nucleic acid that is engineered through the combination or insertion of one or more nucleic acids, thereby combining sequences that would not normally occur together in nature. In some embodiments, nucleic acids comprise inducers or enhancers. In some embodiments, nucleic acids comprise restriction enzyme sites. In some embodiments, nucleic acids encode polypeptides. In some embodiments, nucleic acids comprise mutations.

As used herein, the term "polypeptide" refers to a polypeptide that is produced from a nucleic acid.

As used herein, the term "transgene" refers to the integration of a nucleic acid that encodes a polypeptide into the genomic DNA of an animal, bacteria, virus or cell.

As used herein, "over-expression", refers to a higher level of expression when compared to the endogenous level of expression of an identical polypeptide or protein within the same cell. In certain instances, "over-expression" refers to expression of a polypeptide. In some embodiments a higher level of expression comprises 2% to 200% higher. In some embodiments a higher level of expression comprises 2-fold to 1000-fold higher. In some embodiments a higher level of expression comprises 2-fold to 1000-fold higher. In some embodiments a higher level of expression comprises 2-fold to 10,000-fold higher. In some embodiments a higher level of expression comprises a detectable level of expression when compared to a previous undetectable level of expression. In some embodiments "over-expression" refers to any detectable level of expression of an exogenous polypeptide or protein.

The terms "polypeptide", "peptide", and "protein" are used interchangeably herein to refer to a polymer of amino acid residues. The terms apply to naturally occurring amino acid polymers as well as amino acid polymers in which one or more amino acid residues is a non-naturally occurring amino acid, for example, an amino acid analog. As used herein, the terms encompass amino acid chains of any length, including full length proteins, wherein the amino acid residues are linked by covalent peptide bonds.

As used herein, reference to an isolated protein or polypeptide in the present embodiments include full-length proteins, fusion proteins, chimeric proteins, or any fragment (truncated form, portion) or homologue of such a protein. More specifically, an isolated protein can be a protein (including a polypeptide or peptide) that has been removed from its natural milieu (i.e., that has been subject to human manipulation), and can include, but is not limited to, purified proteins, partially purified proteins, recombinantly produced proteins, membrane bound proteins, proteins complexed with lipids, soluble proteins, synthetically produced proteins, and isolated proteins associated with other proteins. As such, "isolated" does not reflect the extent to which the protein has been purified. Preferably, an isolated protein is produced recombinantly.

Preferably, an isolated nucleic acid molecule is produced using recombinant DNA technology (for example, polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect (for example, provision of an inducible protooncogene, as described herein).

A nucleic acid molecule homologue can be produced using a number of methods known to those skilled in the art (see, for example, Sambrook et al., Molecular Cloning: A Laboratory Manual, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule or polynucleotide is a size sufficient to encode a protein useful for embodiments provided herein, such as a protein encoded by a protooncogene or functional portion thereof (for example, a portion that has the biological activity of the full-length protein and that is sufficient for use in the method), or an antiapoptotic protein or a functional portion thereof (for example, a portion that has the biological activity of the full-length protein and that is sufficient for use in the method). Other nucleic acid molecules that may be useful can include nucleic acid molecules of a minimum size sufficient to form a probe or oligonucleotide primer that is capable of forming a stable hybrid with the complementary sequence of a nucleic acid molecule encoding the natural protein (for example, under moderate, high or very high stringency conditions), which is typically at least 5 nucleotides in length, and preferably ranges from about 5 to about 50 or about 500 nucleotides or greater, including any length in between, in whole number increments (i.e., 5, 6, 7, 8, 9, 10, . . . 33, 34, . . . 256, 257, . . . 500). There is no limit, other than a practical limit, on the maximal size of a nucleic acid molecule, in that the nucleic acid molecule can include a sequence or sequences sufficient to be useful in any of the embodiments described herein.

As used herein, stringent hybridization conditions refer to standard hybridization conditions under which nucleic acid molecules are used to identify similar nucleic acid molecules. Such standard conditions are disclosed, for example, in Sambrook et al., Molecular Cloning: A Laboratory Manual, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, Anal. Biochem. 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (for example, conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (for example, conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (for example, conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C.' below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (for example, at least one wash as about 37° C. in about 0.1×-0.5×SSC, followed by at least one wash at about 68° C. in about 0.1×-0.5×SSC).

In some embodiments, any amino acid sequence described herein, including truncated forms (fragments or portions) and homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. Heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

A recombinant vector (also referred to generally as a recombinant nucleic acid molecule, particularly when it contains a nucleic acid sequence of interest) is an engineered (for example, artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell. Such a vector typically contains heterologous nucleic acid sequences, for example, nucleic acid sequences that are not naturally or usually found adjacent to a nucleic acid sequence to be cloned or delivered, although the vector can also contain regulatory nucleic acid sequences (for example, promoters, untranslated regions) which are naturally found adjacent to nucleic acid molecules, or which are useful for expression of the nucleic acid molecules (discussed in detail below). A vector can be either RNA or DNA, either prokaryotic or eukaryotic, and typically is a plasmid or a viral vector. The vector can be maintained as an extrachromosomal element (for example, a plasmid) or it can be integrated into the chromosome of a host cell. The entire vector can remain in place within a host cell, or under certain conditions, the plasmid DNA can be deleted, leaving behind the nucleic acid molecule. Under other conditions, the vector is designed to be excised (removed) from the genome of the host cell at a selected time (described in more detail below). The integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

In some embodiments, the stem cells can include any adult stem cells obtained from any source. In another embodiment, stem cells can include embryonic stem cells. Stem cells can include, but are not limited to, hematopoietic stem cells, mesenchymal stem cells (including, but not limited to, lung mesenchymal stem cells, bone marrow stromal cells), neural stem cells, epithelial stem cells (including, but not limited to, lung epithelial stem cells, breast epithelial stem cells, vascular epithelial stem cells, and intestinal epithelial stem cells), intestinal stem cells, cardiac myocyte progenitor stem cells, skin stem cells (including, but not limited to, epidermal stem cells and follicular stem cells (hair follicle stem cells)), skeletal muscle stem cells, osteoblastic precursor stem cells, and liver stem cells.

Hematopoietic stem cells give rise to all of the types of blood cells, including but not limited to, red blood cells (erythrocytes), B lymphocytes, T lymphocytes, natural killer cells, neutrophils, basophils, eosinophils, monocytes, macrophages, and platelets.

Mesenchymal stem cells (including bone marrow stromal cells) give rise to a variety of cell types, including, but not limited to bone cells (osteocytes), cartilage cells (chondrocytes), fat cells (adipocytes), lung cells, and other kinds of connective tissue cells such as those in tendons.

Neural stem cells in the brain give rise to its three major cell types: nerve cells (neurons) and two categories of non-neuronal cells, astrocytes and oligodendrocytes.

Epithelial stem cells in the lining of various tissues give rise to several cell types that form the epithelium in tissues.

Skin stem cells occur in the basal layer of the epidermis and at the base of hair follicles. The epidermal stem cells give rise to keratinocytes, which migrate to the surface of the skin and form a protective layer, and the follicular stem cells can give rise to both the hair follicle and to the epidermis. Other sources of adult stem cells will be known to those of skill in the art.

Embryonic stem cells can give rise to all tissues and cells of the body.

Methods

The long term repopulating hematopoietic stem cell (LT-HSC) population self-renews in vivo and supports hematopoiesis for the lifetime of the individual. Long term HSCs are of importance in the context of bone marrow stem cell transplantation, among others.

The function of hematopoietic stem cells (HSCs) in vivo is dependent on complex micro-environmental signals that determine self-renewal, lineage commitment and differentiation. Attempts to expand HSC populations have been hampered by the inability to maintain pluripotency and to prevent differentiation, while allowing self-renewal (Bernstein, I.D. and Delaney, C. (2012). Cell Stem Cell 10, 113-4). Previous efforts to expand HSCs in vitro involved using cytokine cocktails (Chou, S., et al. (2010). Cell Stem Cell 7, 427-8), ligands for Notch-1 (Dahlberg, A., et al (2011). Blood 117, 6083-90), Tat-fusion proteins for HoxB4 (Krosl, J., et al. (2003). Nat Med 9, 1428-32), NF-Ya (Domashenko, A. D., et al, (2010). Blood 116, 2676-83), and other transcription factors (Yang, J. et al. (2011). J Hematol Oncol 4, 38), as well as small molecules (PGE2 and a Aryl Hydrocarbon Receptor Antagonists) (North, T. E., et al. (2007). Nature 447, 1007-11; Boitano, A. E., et al. (2010). Science 329, 1345-8). The nature of the expanded cells varies among these different approaches, yielding mixed results in xenochimaeric transplanted mouse studies, and in the clinic (Walasek, M. A., et al. (2012). Ann NY Acad Sci, 1266, 138-50).

Obstacles in current stem cell therapies include difficulties obtaining sufficient numbers of needed cells, and identification of allogeneically appropriate donors. Some embodiments described herein allow for the ability to generate large numbers of HSCs. The ability to transplant a pure and homogeneous population of stem cells also allows for reconstitution of irradiated hosts across allogeneic barriers.

In some embodiments, a method for producing a population of conditionally immortalized adult stem cells (protein-transduced long term HSCs, "ptlt-HSCs") is provided. The method can comprise providing one or more adult stem cells with a) an exogenously synthesized Myc polypeptide that promotes one or more of cell survival or proliferation and b) an exogenously synthesized Bcl-2 domain polypeptide that inhibits apoptosis. In some embodiments, the Myc polypeptide is provided to the one or more adult stem cells at intervals of at least about 72 hours. In some embodiments, the Bcl-2 domain polypeptide is provided to the one or more adult stem cells at intervals of at least about 96 hours, so as to produce a population of conditionally immortalized adult stem cells. The term "exogenously synthesized" denotes that the proteins are not synthesized within the cells that they are acting upon. In some embodiments, the exogenously synthesized proteins are added to the cells in an isolated form (for example, buffer and just these proteins). In some embodiments, the exogenously synthesized proteins are produced by a first population of cells, separate from the stem cells.

Although not intending to be bound by theory, the function of the proto-oncogene encoded protein (for example, Myc polypeptide) appears to prevent exit of HSCs from the cell cycle, driving their continuous proliferation and inhibiting their differentiation. Signals provided by the cytokine cocktail including IL-3, IL-6, SCF and other cytokines maintain the HSC phenotype of proliferating ptlt-HSC cells. The survival function provided by the anti-apoptotic protein (for example, Bcl-2 domain polypeptide) allows rescue of ptlt-HSC cells from the apoptotic death that would normally follow withdrawal of the proto-oncogene encoded protein function. This appears to allow the HSCs to regain their ability to use physiologically available survival signals in vivo. Thus, in some embodiments, the method can include driving proliferation and inhibiting differentiation and can comprise applying both Bcl-2 domain polypeptides and Myc polypeptides, and subsequently withdrawing the Myc polypeptide (or allowing its levels to decrease), while keeping some amount of Bcl-2 present, so that the cells survive the withdrawal of Myc, allowing them to be subsequently differentiated.

While not intending to be bound by theory, it appears that, upon adoptive transfer of ptlt-HSCs, the anti-apoptotic protein survival function allows cells to habituate to micro-environmental signals provided by the bone marrow stem cell niche. In conditions of need, such as radiation-induced lymphopenia, these signals may drive differentiation of ptlt-HSCs to generate functional lymphoid cells and other differentiated blood cells. It is noted that no leukemias were observed in mice reconstituted with ptlt-HSCs. Thus, in some embodiments, methods for generating such advantageous cells are provided herein.

In some embodiments, the method can include stopping and/or reducing the addition of Myc so that the amount of Myc in the media decreases over time. During this period of time in which the amount of Myc is decreasing, one can continue to add Bcl-2 when appropriate, to maintain an acceptable level of Bcl-2.

In some embodiment, the Myc polypeptide is provided at intervals of at least about 72 hours. In some embodiments, the Myc polypeptide can be provided more frequently, for example, every 24, 32, 40, 48, 56, or 64 hours.

In some embodiments, the Myc polypeptide and/or Bcl-2 domain polypeptide is administered no more frequently than one time each hour, for example once every two hours, once every three hours, once every four hours, once every five hours, once every six hours, once every seven hours, once every eight hours, once every nine hours, once every 10 hours, once every 11 hours, once every 12 hours, once every 13 hours, once every 14 hours, once every 15 hours, once every 16 hours, once every 17 hours, once every 18 hours, once every 19 hours, once every 20 hours, once every 21 hours, once every 22 hours, once every 23 hours, or once every 24 hours. In some embodiments, the Myc polypeptide and/or Bcl-2 domain polypeptide is administered no more frequently than one time each day, for example once every two days, once every three days, or once every four days. In some embodiments, this can be achieved, despite the short half-life of traditional Myc polypeptides (for example 36 minutes) by using the various embodiments of the Myc polypeptide provided herein. In some embodiments, despite the low frequency of administration of the Myc polypeptide, the amount of Myc polypeptide administered at one time will be less than about 100 micrograms/ml, for example 50-100 micrograms/ml or 20 micrograms/ml or less. In such situations, because of the extended half-life, the Myc can still be effective for one or more of the above noted periods of time, without needing additional Myc polypeptide (for example. 1, 2, 3, 4, 5, 6, 7, 8, 12, 16, 24, or 48 hours without additional Myc polypeptide being required, while still providing an effective level of Myc activity to the cells).

In some embodiments, the amount of Myc and/or Bcl-2 domain polypeptide is applied all at once over a short period of time, for example, the amount of Myc and/or Bcl-2 domain polypeptide can be applied in a single dump, all at once, or over 1, 5, 10, or 60 seconds. In some embodiments, the Myc and/or Bcl-2 domain polypeptide can be applied over 1 minute to 60 minutes, for example, about 1, 3, 5 or 10 minutes.

In some embodiments, the Myc polypeptide is provided continuously. In some embodiments, the Myc polypeptide is provided at a concentration of at least about 0.1 microgram/ml, for example, 5, 10, 50, or 100 micrograms/ml. In some embodiments, the Myc polypeptide is provided at a range of about 0.1 to about 50 micrograms/ml. In some embodiments, no more than 1 microgram/ml is provided to the cells in an 8, 12, 16, or 24 hour period.

In some embodiments, the Bcl-2 domain polypeptide is provided at intervals of at least about 72 hours. In some embodiments, the Bcl-2 domain polypeptide can be provided more frequently, for example, once every 24, 32, 40, 48, 56, or 64 hours.

In some embodiments, the Bcl-2 domain polypeptide is provided continuously. In some embodiments, the Bcl-2 domain polypeptide is provided at a concentration of at least about 0.1 microgram/ml, for example, 5, 10, 50, or 100 micrograms/ml. In some embodiments, the Bcl-2 domain polypeptide is provided at a range of about 1 to about 50 micrograms/ml. In some embodiments, the Bcl-2 domain polypeptide is provided at a concentration of about 1 microgram/ml. In some embodiments, the ratio of Bcl-2 domain polypeptide to Myc can depend upon the desired process that one wishes to achieve. In some embodiments, the ratio of Bcl-2 to Myc is at least 1:1, for example at least 2:1 Bcl-2 to Myc.

In some embodiments, the Bcl-2 domain polypeptide and the Myc polypeptide can be administered at the same time. In some embodiments, the Bcl-2 domain polypeptide and the Myc polypeptide can be administered at different times. In some embodiments, the Bcl-2 domain polypeptide and the Myc polypeptide can be administered at overlapping times.

In some embodiments, any of the Myc polypeptides and/or Bcl-2 domain polypeptides provided herein can be used in the methods provided herein.

In some embodiments, the cells can be cultured at a variety of temperatures and under a variety of conditions. In some embodiments, they can be cultured at about 37° C. In some embodiments, the cells can be cultured in a gas permeable container, such as a gas permeable flask (such as those produced by G-Rex) or a gas permeable bag (such as those made by Origene). In some embodiments, this provides for a superior approach over those made in static cultures in plastic TC containers. In some embodiments, the process can occur in a gas permeable vessel within an incubator with about 5% $CO_2$. In some embodiments, the gas permeable vessel can be rapid expansion cultureware. In some embodiments, the vessel includes a silicone membrane, at its sides and/or bottom to allow for exchange of gas.

In some embodiments, the resulting ptlt-HSCs resemble HSCs by one or more of cell surface phenotype, in vitro differentiation capacity, ability to reconstitute the hematopoietic lineages in vivo following irradiation, and/or ability to be transplanted in a serial manner. In some embodiments, the cells can go through at least two serial passages, for example, 3, 4, 5, 6 or more passages.

In some embodiments, the ptlt-HSCs can be rapidly expanded from any source of HSCs including but not limited to cord blood, placenta, mobilized peripheral blood, and bone marrow as well as HSCs from embryonic stem cells or from induced pluripotent stem cells. In some embodiments, the ptlt-HSCs give rise to a self-renewing HSC compartment in vivo following transplantation. In some embodiments, this can be achieved by administering the ptlt-HSCs to a subject.

In some embodiments, the adult stem cell are expanded one or more times over a period of times. In some embodiments, the adult stem cells are expanded about 270 fold over about 28 days (for example, for mouse 5FU enriched BM). In some embodiments, the adult stem cells are expanded about 150 fold over about 14 days (for example, for human FCB derived). In some embodiments, the adult stem cells are expanded 100 fold over about 21 days. In some embodiments, the adult stem cells are expanded about 85 fold over about 9 to 14 days (for human mobilized). As will be appreciated by those of skill in the art, given the present disclosure, being able to administer the Myc polypeptide and/or the Bcl-2 domain polypeptide less frequently, will assist in being able to store such cells.

As will be appreciated by one of skill in the art, given the present disclosure, Myc and variants and/or homologs thereof can be employed in various embodiments herein. In some embodiments, the Myc polypeptide is one or more of n-Myc, c-Myc, l-Myc, v-Myc, or s-Myc. As used herein, the terms "Myc", "cMyc", "Myc protein" and "Myc polypeptide" are used interchangeably and refer in certain instances to the NCBI Accession Number NP002458.2, functional homologs, analogs or fragments thereof. In some embodiments, synonyms of Myc include, but are not limited to c-Myc, v-Myc, Myc proto-oncogene protein & Transcription factor p64. In some embodiments, a Myc polypeptide comprises an amino acid sequence that is at least 40% to 100% identical, for example, at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the sequence of NCBI Accession Numbers NP002458.2. In some embodiments, a Myc polypeptide comprises a polypeptide sequence of 40 amino acids or more in length that is at least 50% to 100% identical, for example, at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2. In some embodiments, a Myc polypeptide comprises a polypeptide sequence of 40 amino acids or more in length that is at least 50% to 100% identical, for example, at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2 and wherein the Myc polypeptide induces cell viability, cell immortality, cell growth and/or cell proliferation.

BCL-2 Domain

In some embodiments, the Bcl-2 domain polypeptide can be any member of the Bcl-2 family and/or any protein that it has adequate homology thereto so as to allow the protein to function in an anti-apoptotic manner. In some embodiments, the Bcl-2 domain polypeptide can comprise the BH1 domain of Bcl-2. In some embodiments, the Bcl-2 domain polypeptide can comprise the BH2 domain of Bcl-2. In some embodiments, the Bcl-2 domain polypeptide can comprise the BH3 domain of Bcl-2. In some embodiments, the Bcl-2 domain polypeptide can comprise the BH4 domain of Bcl-2. In some embodiments, the Bcl-2 domain polypeptide can comprise the BH1 and BH2 domains of Bcl-2, the BH1 and BH3 domains, the BH1 and BH4 domains, the BH2 and BH3 domains, the BH2 and BH4 domains, the BH3 and BH4 domains, the BH1, BH2, and BH3 domains, the BH2, BH3, and BH4 domains, or all of the BH1, BH2, BH3, and BH4 domains. In some embodiments, a polypeptide can be a Bcl-2 domain polypeptide, as long as it is at least 90% identical to at least one or more of BH1, BH2, BH3, or BH4, for example, 91, 92, 93, 94, 95, 96, 97, 98, 99, or greater percent identity to at least one of BH1, BH2, BH3, and/or BH4. In some embodiments, the Bcl-2 domain polypeptide comprises the BH1, H2 and BH4 domains. In some embodiments, the Bcl-2 domain polypeptide includes one or more of Bcl-2, Bcl-w, Bcl-X, Bcl-XL, or Mcl-1. The term "Bcl-2 domain polypeptide" includes homologs thereof, to the extent they function as noted herein. Thus, variants of Bcl-2 proteins are also included within the scope of the term. In some embodiments, the Bcl-2 domain polypeptide encompasses full length Bcl-2. In some embodiments, Bcl-2 domain polypeptide comprises a truncated form of human Bcl-2, that has been deleted for the unstructured loop domain (Anderson, M., et al. (1999) Prot Expr. Purif 15, 162-70).

In some embodiments, a Bcl-2 domain polypeptide comprises an amino acid sequence that is at least 40% to 100% identical, for example, at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the sequence of NCBI Accession Numbers: NM_000633.2 and/or NM_000657.2

Transduction Domain

In some embodiments, the Myc polypeptide and/or the Bcl-2 domain polypeptide includes a protein transduction domain. In some embodiments, the protein transduction domain comprises Tat. In some embodiments, the protein transduction domain comprises EPTD. In some embodiments, the protein transduction domain comprises at least one of vpr, R9, R15, VP16, Antennapedia, aptamer technology, chariot technology, R11, etc. In some embodiments, the protein transduction domain is covalently linked to the Myc polypeptide or the Bcl-2 domain polypeptide. In some embodiments, the protein transduction domain is linked to the Myc polypeptide or the Bcl-2 domain polypeptide via a peptide bond. In some embodiments, the protein transduction domain is linked to the Myc polypeptide and/or the Bcl-2 domain polypeptide via a linker sequence, which can be composed of short stretches of neutral amino acids In some embodiments, the Tat-Myc polypeptide can be that shown in FIG. 15A. In some embodiments, the Tat-Bcl-2 domain polypeptide can be that shown in FIG. 15B.

Media

In some embodiments, the adult stem cell is cultured in media comprising at least one of IL3, IL6, and a stem cell factor. In some embodiments, the adult stem cell is cultured in media comprising IL3, IL6, and stem cell factor. In some embodiments, the adult stem cell is cultured in media comprising IL3, IL6, stem cell factor, thrombopoeitin, and Flt3-L. In some embodiments, the adult stem cell is cultured in media comprising IL3, IL6, stem cell factor, thrombopoeitin, and Flt3-L, and GM-CSF. In some embodiments, the amount of: IL3, IL6, stem cell factor, thrombopoeitin, Flt3-L, and/or GM-CSF can be present in a range of from 10-500 ng/ml.

Cell Types

In some embodiments, the adult stem cell is one or more hematopoietic adult stem cell. In some embodiments, the hematopoietic adult stem cell can be characterized by one or more of cell surface phenotype, in vitro differentiation capacity, ability to reconstitute the hematopoietic lineages in vivo following irradiation, or ability to be transplanted in a serial manner. In some embodiments, the hematopoietic adult stem cell can be characterized by an appropriate cell surface phenotype, in vitro differentiation capacity, ability to reconstitute the hematopoietic lineages in vivo following irradiation, and ability to be transplanted in a serial manner. In some embodiments, for a mouse cell to be considered a hematopietic adult stem cell it can exhibit one or more of the following: surface phenotype (Sca-1+, c-kit+, lineage−), able to reconstitute irradiated syngeneic mice with as few as 10 cells per transfer, and give rise to a self-renewing HSC population that can rescue irradiated recipients following serial passages. In some embodiments, for a human cell to be considered a hematopietic adult stem cell it can exhibit one or more of the following: a surface phenotype of CD34+, CD38+/lo, lineage negative, flk-2−; ability to give rise to several colony types and morphologies on defined methycellulose differentiation media, along with the ability to give rise to cells that can be serially plated in that in vitro differentiation system; cells should be able to give rise to human mature hematopoietic cells in xenotransplantation studies using NOD/SCID/gamma chain ko or other profoundly immunocompromised mouse strain, and give rise to serially transplantable HSCs in that xenotrasplant system.

In some embodiments, the one or more hematopoietic adult stem cells are isolated from one or more of cord blood, placenta, bone marrow, peripheral blood, mobilized peripheral blood, or adipose tissue. In some embodiments, the hematopoietic adult stem cell is derived from an embryonic stem cell or an induced pluripotent stem cell.

In some embodiments, the one or more adult stem cells are human cells. In some embodiments, the one or more adult stem cells are non-human animal cells, such as, for example, mouse, rat, dog, horse, cat, pig, etc.

Proteins

In some embodiments, a protein is provided. The protein can be a Myc fusion protein comprising a protein transduction domain, a Myc polypeptide that promotes one or more of cell survival or proliferation (which can be exogenously synthesized), a V5 domain, and a six histidine epitope tag. In some embodiments, the Myc fusion protein has a half-life that is longer than about 60 minutes in tissue culture conditions of 37° C. in an atmosphere with 5% $CO_2$, in aqueous solution.

In some embodiments, the Myc fusion protein half-life is about 48 hours. In some embodiments, the Myc fusion protein has an adequate half-life such that it is detectable up to about 48 hours, for example 72 hours.

In some embodiments, the Myc fusion protein is transported to the nucleus in cells. In some embodiments, the Myc fusion protein is located in the nucleus in cells.

In some embodiments, the protein transduction domain can be any protein transduction domain. In some embodiments, the protein transduction domain comprises Tat, Vpr, and/or EPTD. In some embodiments the protein transduction domain comprises at least one of VP16, R9, R15, or other protein transduction domains.

In some embodiments, the Myc fusion protein can be arranged in any desired order. In some embodiments, the Myc fusion protein can be arranged in order of a) the protein transduction domain connected in frame to the Myc polypeptide, b) the Myc polypeptide connected in frame to the V5 domain, and c) the V5 domain connected in frame to the six histidine epitope tag. In some embodiments, the Myc fusion protein has an order of components of a) the Myc polypeptide connected in frame to the protein transduction domain, b) the protein transduction domain connected in frame to the V5 domain, and c) the V5 domain connected in frame to the six histidine epitope tag. In some embodiments, additional intervening amino acid sequences can be included between each of the sequences. In some embodiments, additional amino acid sequences can be included at the start and/or end of the sequences.

In some embodiments, the Myc fusion protein comprises a protein transduction domain, a Myc polypeptide that promotes one or more of cell survival or proliferation, and a short peptide domain. The short peptide domain can be varied. In some embodiments, the short peptide domain is selected from at least one of a V5, a histidine-tag, HA (hemagglutinin) tags, FLAG tag, CBP (calmodulin binding peptide), CYD (covalent yet dissociable NorpD peptide), StrepII, or HPC (heavy chain of protein C). In some embodiments, the short peptide domain is about 10 or 20 amino acids long. In some embodiments, the short peptide domain is 2-20, for example 6-20 amino acids in length. In some embodiments, two of the above listed items (for example, V5 and the his-tag) can be used together as the short peptide domain.

Expansion Media

In some embodiments, a stem cell expansion media is provided. The expansion media can include a) a base media, and b) at least one or more of the following: IL3, IL6, stem cell factor, thrombopoeitin, Flt3-L, and GM-CSF. In some embodiments, it includes IL3, IL6, stem cell factor, thrombopoeitin, Flt3-L, and GM-CSF. In some embodiments, it includes IL3, IL6, stem cell factor, thrombopoeitin, and Flt3-L. In some embodiments, the expansion media can include IL3, IL6, stem cell factor, thrombopoeitin, Flt3-L, and GM-CSF.

In some embodiments, the cell expansion media comprises a Myc polypeptide that promotes one or more of cell survival or proliferation. In some embodiments, the cell expansion media comprises an exogenously synthesized Myc polypeptide that promotes one or more of cell survival or proliferation. In some embodiments, the cell expansion media comprises a Myc polypeptide as provided herein.

In some embodiments, the stem cell expansion media further comprises a Bcl-2 domain polypeptide that inhibits apoptosis. In some embodiments, the stem cell expansion media further comprises a Bcl-2 domain polypeptide as provided herein. In some embodiments, the stem cell expansion media further comprises an exogenously synthesized Bcl-2 domain polypeptide that inhibits apoptosis.

In some embodiments, any base media can be employed. In some embodiments, the base media can comprise one or more of StemSpan, Isco's media, RPMI, or DMEM.

Additional Aspects:

Methods for obtaining such stem cells and providing initial culture conditions, such as a liquid culture or semi-solid culture medium, are known in the art. In some embodiments, the cells are initially expanded in vivo or in vitro, by contacting the source of the stem cells with a suitable reagent that expands or enriches such cells in the tissue source or in culture. For example, in the case of hematopoietic stem cells, the donor individual can be treated with an agent that enriches for hematopoietic stem cells and encourages such cells to proliferate without differentiation, such as 5-fluorouracil. Other suitable agents for expansion of a desired stem cell type will be known to those of skill in the art. Alternatively, adult stem cells are isolated from a tissue source and then expanded or enriched in vitro by exposure to a suitable agent. For example, with regard to hematopoietic stem cells, a method for producing an expanded culture of adult hematopoietic progenitors is described in Van Parijs et al., (1999; Immunity, 11, 763-70). Cells are obtained from an individual by any suitable method for obtaining a cell sample from an animal, including, but not limited, to, collection of bone marrow collection of a bodily fluid (for example, blood), collection of umbilical cord blood, tissue punch, and tissue dissection, including particularly, but not limited to, any biopsies of skin, intestine, cornea, spinal cord, brain tissue, scalp, stomach, breast, lung (for example, including lavage and bronchioschopy), fine needle aspirates of the bone marrow, amniotic fluid, placenta and yolk sac.

In some embodiments, cells can also be obtained from fresh, or cryopreserved (stored) cord blood, hematopoietic progenitor populations that can be derived from the directed differentiation of embryonic stem (ES) cells in vitro, hematopoietic stem cells (HSCs) obtained from the peripheral blood of normal or granulocyte colony-stimulating factor (G-CSF)-treated patients who have been induced to mobilize their lt-HSCs to the peripheral circulation.

In some embodiments, the cells produced herein can be used to treat various disorders. In some embodiments, the methods provided herein can be used to culture cells for those in need. In some embodiments, the cells are from the subject to receive the cells (autologous).

In some embodiments, the cells generated herein or that contain one or more of the constructs provided herein (protein etc.) can be used in the treatment of subjects who have undergone radiation and/or chemotherapy (for example cancer patients, or have been exposed to high-level radiation), for the treatment of immune deficiency and hematological malignancies, for bone marrow transplantation to combat the negative effects of aging on the immune system. In some embodiments, this can be used in the treatment of heart disease, or to reduce graft versus host reactions.

In some embodiments, the cells generated herein can be used for gene correction approaches for therapy of monogenic diseases. In some embodiments, one can use autologous HSCs that can be gene corrected with a TALEN, or other approach and transfuse the cells back to the patient. In some embodiments, this allows amplification before and after the gene correction, especially since those correction approaches will involve cell division.

In some embodiments, the present methods can be applied to diseases where the patient cannot be mobilized or subjected to G-CSF treatment for mobilizing HSCs. In those instances, a small number of HSCs can be obtained from peripheral blood and amplified via the methods provided herein and can allow for a successful therapeutic application. These diseases include, but are not limited to lysosomal storage diseases, sickle cell anemia, congenital anemias, Epidermylysis Bullosa (4 types), etc.

EXAMPLES

Example 1

Generation of Biologically Active Tat-Myc and Tat-Bcl-2 Fusion Proteins

Fusion proteins having the HIV-1 Tat protein transduction domain (PTD) and either the ORF for human Myc, or a truncated form of human Bcl-2, that has been deleted for the unstructured loop domain (Anderson, M., et al. (1999). Prot Expr. Purif 15, 162-70), were generated. The recombinant proteins also encoded a V5 peptide tag and a 6-His tag, to facilitate detection and purification (FIG. 1A).

pTAT-Myc-V5-6×His ($Amp^R$) and pTAT-Bcl2Δ-V5-6×His ($Amp^R$): plasmid were generated by PCR amplification of a cDNA encoding human cMyc or human Bcl2 using a forward primer encoding an in frame TAT protein transduction domain of HIV (RKKRRQRRR) (SEQ ID NO: 5). The PCR products were cloned into pET101/D-Topo (Invitrogen) vector. The unstructured loop (A.A. #27-80) was removed from the BCL-2 coding sequence using a Quick Change site directed mutagenesis kit (Stratagene #200521-5).

Figure 1B:
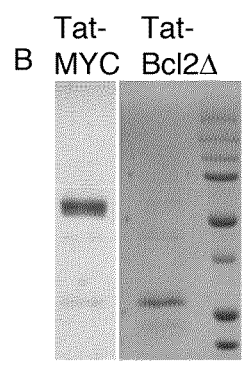

The proteins were synthesized in *E. coli* and purified to homogeneity. SDS-PAGE electrophoresis and Coomassie Staining revealed the level of purity of the final product used for our studies (FIG. 1B). pTAT-Myc-V5-6×His was transformed into BL21-STAR(DE3) cells (Invitrogen) and protein was induced with 0.5 mM IPTG at 37° C. for 3 hrs. The cells were lysed in lysis buffer (8M urea, 100 mM NaH2PO4, 10 mM Tris pH to 7.0, 10 mM imidazole, pH 7.2). The lysate was diluted to 6M urea and brought to 450 mM NaCl, 50 mM $NaH_2PO_4$, 5 mM Tris pH 7.0. The lysate was treated with Benzonase (500 units) at room temp for 1 hour, clarified by centrifugation at 12,000 RPM for 60 min and filtered through a 0.22 µM filter. Myc-V5-6×His was purified on a nickel affinity column (GE) using a GE AKTA purifier 10 FPLC. Myc-V5-6×His was refolded by dialyzing into dialysis buffer (450 mM NaCl, 50 mM $NaH_2PO_4$, 5 mM Tris pH 7.0, 5% glycerol, 1 mM DTT). Endotoxin was reduced by passing the purified protein over an Acticlean Etox column (Sterogen).

Bcl2Δ-V5-6×His protein was induced as described above. The cells were lysed in 50 mL of lysis buffer (200 mM NaCL, 200 mM KCL, 50 mM $NaH_2PO_4$, 5 mM Tris pH 7.0, 5% glycerol, 1 mM DTT) supplemented with 500 units Benzonase, 1 mM PMSF, 2 ug/ml Leupeptin, 0.015 units/ml Aprotinin, 5 uM Hen Egg Lysozyme (HEL) per 1 L of induced protein, and immediately placed on ice for 1 hour. The cells were sonicated on ice (Duty cycle=50%, Output=5) for 2 sets of 2 minutes. The lysate was cleared by centrifugation at 12,000 RPM for 60 min and was filtered through a 0.22 µM filter. Bcl2Δ-V5-6×His was purified on a nickel affinity column (GE) and endotoxin was removed as described above.

Example 2

Confirmation of Appropriate Localization of Tat-Fusion Proteins

Figure 1C:
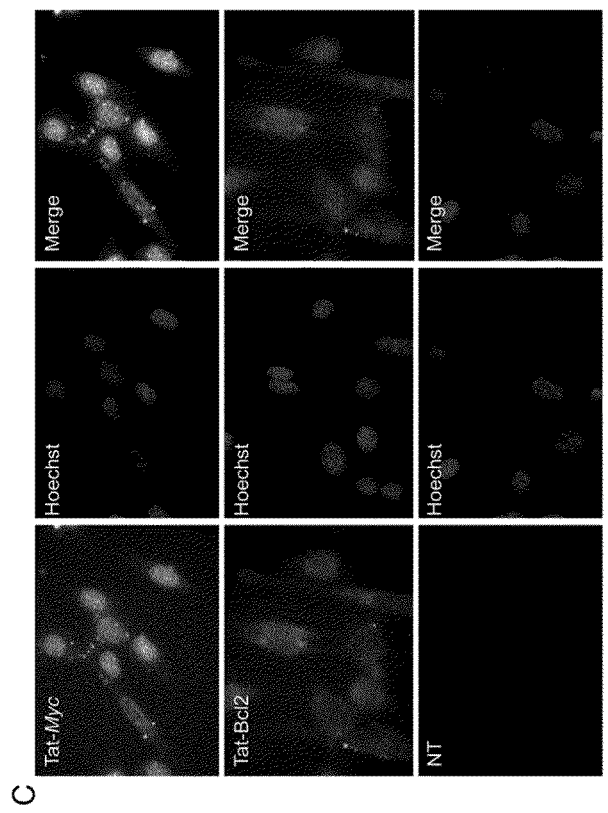

The fusion proteins localize to the appropriate intracellular compartment (FIG. 1C). NIH 3T3 cells were seeded onto glass cover slips in six-well plates and grown to 30 to 40% confluence. Each well was transduced with 10 µg/ml of Tat-Myc or Tat-Bcl-2 or no treatment as a negative control. The cells were fixed in 4% paraformaldehyde-PBS for 10 minutes at room temperature (RT) 2 hours following the protein transduction. Cells were permeabilized in PBS supplemented with 1% bovine serum albumin (BSA) and 0.1% Triton X-100 at RT for 3 minutes. Cells were incubated for 45 minutes with V5 mouse monoclonal antiserum (Invitrogen) diluted in PBS-1% BSA (1:1,000). Cells were washed and incubated for 30 minutes with Goat anti-mouse Alexa 488 secondary antibodies (Invitrogen A21121). Cover slips were mounted onto glass slides with a 10 µl drop of 50% glycerol with Hoechst at 1 µg/ml. Images were obtained on a Zeiss Imager Z1 Fluorescence microscope.

Figure 1D:
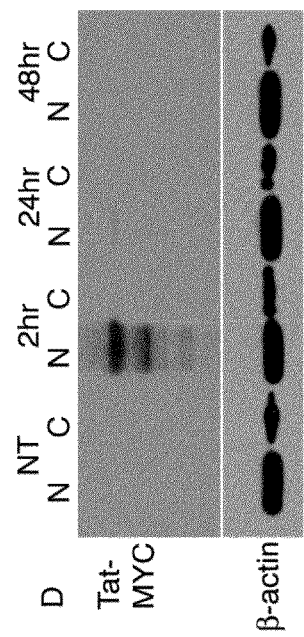
Figure 1E:
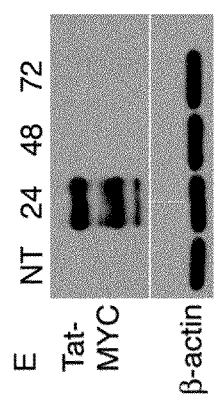

Tat-Myc rapidly localized to the nucleus in primary human HSCs (FIG. 1D). Tat-fusion proteins are fully degraded after 72 hours in HSCs (FIG. 1E). Fetal cord blood cells were transduced with Tat-Myc and Tat-Bcl2Δ for 1 hour followed by 3 PBS washes. Two hours post-transduction 5×10$^6$ cells were harvested and the nuclear and cytoplasmic fractions were isolated. Cells (5×10$^6$) were harvested every 24 hours for the next 5 days. Nuclear and cytoplasmic proteins were prepared by lysing cells in 10 mM HEPES (pH 7.6), 10 mM $NaCl_2$, 3 mM $CaCl_2$, and 0.5% NP40. Nuclei were pelleted, and the cytoplasmic-containing supernatant fraction was precipitated with trichloroacetic acid (TCA). Following SDS-PAGE, Western blots were probed with anti-V5 antibody (Invitrogen), anti-human β-actin (abcam), and goat anti-rabbit IgG-HRP or goat anti-mouse IgG-HRP (Santa Cruz Biotechnology).

Example 3

Cell Survival and Proliferation Using Tat-Fusion Proteins

Figure 2A:
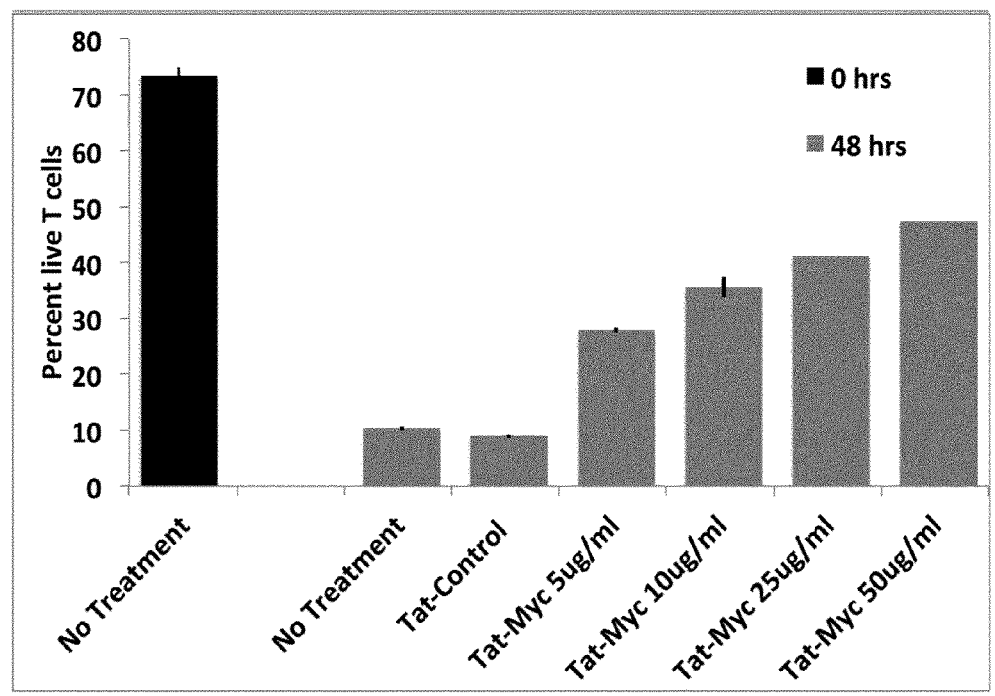
Figure 2B:
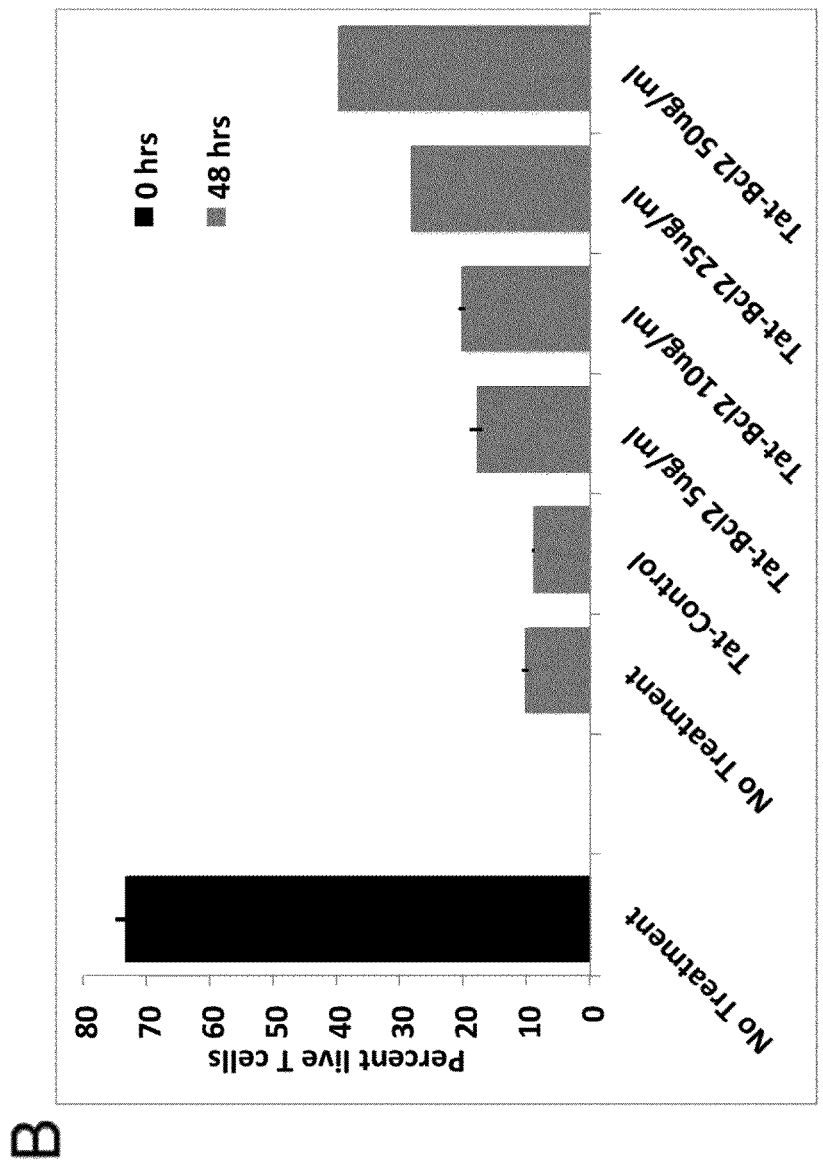
Figure 2C:
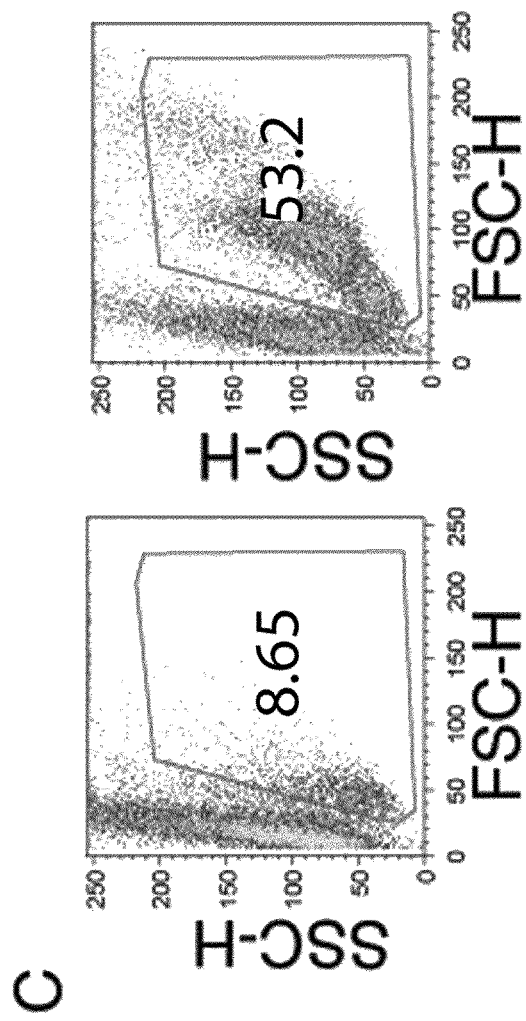
Figure 2D:
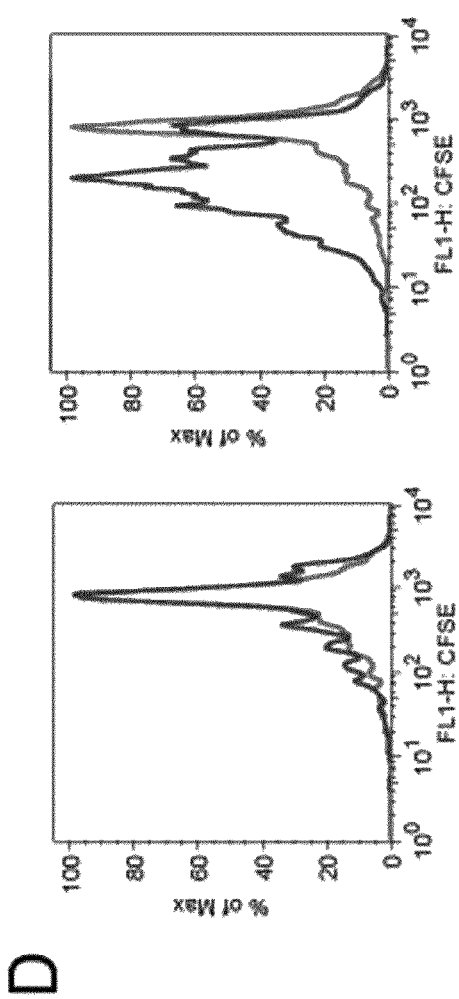

Without treatment, activated murine CD4+ T cells go through apoptosis following cytokine deprivation. Tat-Myc and Tat-Bcl-2 rescue activated primary CD4+ T-cells from cytokine-withdrawal-induced apoptosis in a dose-dependent manner (FIGS. 2A and 2B). Primary murine CD4+ T cells activated in the presence of Tat-Myc showed a robust proliferation when compared to cells activated in the presence of Tat-Cre (FIGS. 2C and 2D).

All mice were handled in accordance with an experimental protocol approved by the Institutional Animal Care and Users Committee at the University of Colorado School of Medicine (protocols #B-87709(03)1B-1 and 87709(09)2E. The spleen was collected from a euthanized C57BL/6J mouse (Jackson Laboratory), and a single cell suspension was generated by mechanical dissociation. The cells were treated with TAC buffer (135 mM $NH_4CL$, 17 mM Tris Ph 7.65) to lyse the red blood cells. T-cells were activated in C10 media (500 ml bottle RPMI 1640, 10% FBS, 100 units per/ml Pen/Strep, 2 mM L-glutamine, 10 mM Hepes, MEM Non-essential Amino Acids, 0.55 mM β-Mercaptoethanol, 1 mM Sodium Pyruvate 100 mM) supplemented with 1 mg/ml of anti-CD3 (monoclonal antibody 2C11) for two days. Live lymphoblast cells were collected on a Ficoll cushion, and seeded in wells of a 24 well dish at 1×10$^6$ cells per well in complete media with or without Tat fusion proteins. Cell division profiles were determined by flow cytometric analysis of CFSE.

Example 4

Expansion of Murine HSCs with Tat-Myc and Tat-Bcl-2

Cohorts of 4-6 week old female C57BL/6J mice were obtained from Jackson Laboratories (Bar Harbor, Me.). The mice were treated with 5 mg/mouse of 5-fluorouracil (5FU), intravenously. Bone marrow (BM) cells were collected from the tibia and femur bones 5 days after 5FU treatment. The red blood cells were lysed by incubation in 5 ml sterile TAC buffer (135 mM NH4CL, 17 mM Tris Ph 7.65). The bone marrow cells were expanded in BM Medium (DMEM containing 15% FCS, 100 units per ml Penn/Strep, MEM NEAA (Gibco), 10 mM HEPES, recombinant murine IL-3, IL-6, and SCF) supplemented with 5 µg/ml recombinant Tat-Myc, and 10 µg/ml recombinant Tat-Bcl-2.

Cytokines were prepared by plating 293FT cells in 150 mm plates at 12×106 cells per plate in D10 media (DMEM, 10% FBS, 100 units per ml Penn/Strep, MEM NEAA (Gibco), 2 mM L-glutamine (Gibco)). The cells were transfected with 30 µg total DNA per plate consisting of 10 µg pcDNA3.1-SCF, 10 µg pcDNA3.1-IL3, and 10 µg pcDNA3.1-IL6 or 10 µg pcDNA3.1-TPO, 10 µg pcDNA3.1-Flt3-L, and 10 µg pcDNA3.1-GM-CSF using calcium phosphate (Young, R. M., et al. (2008). B-cell receptor signaling in the genesis and maintenance of B-cell lymphoma. Future Oncology, 4, 591-4.). The following day, the media was removed and was replaced with 100 ml D10 media. Cells were incubated at 37° C./5% CO2 for 4-5 days. The media was collected, sterile filtered, and frozen at −20° C. in 30 ml aliquots.

Figure 3A:
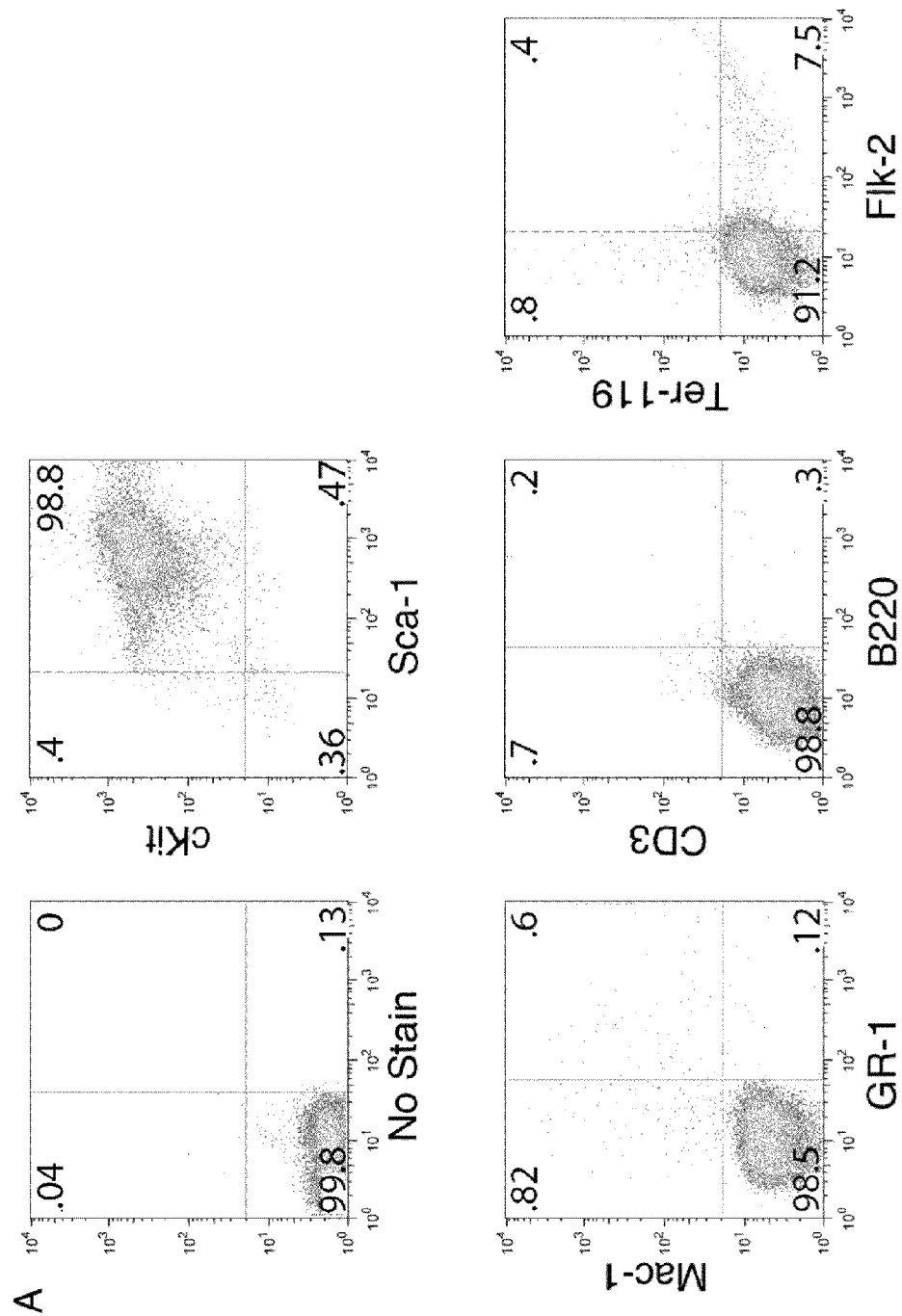

Cells were cultured for 28 days with a BM medium change every 48 hr to refresh the Tat-fusion proteins. As a control, bone marrow cells were cultured in media containing cytokines and Tat-Cre. FIG. 3A and Table 1 show the flow cytometric profile of the resulting HSC population after 28 days in culture. FACS analysis shows a continuing enrichment of the Sca-1/c-kit population (lin−), whereas all other cell types decrease over a 28-day period.

TABLE 1

| Day | Mac-1 | GR-1 | Mac-1 × Gr-1 | Sca-1 | c-Kit | Sca-1 × c-Kit | B220 | CD3 | Flk2 | Ter119 |
|---|---|---|---|---|---|---|---|---|---|---|
| 7 | 55.1 | 0.1 | 39.5 | 41.8 | 0.5 | 2.6 | 4.6 | 0.2 | 2.4 | 0.3 |
| 14 | 20.8 | 3.4 | 48 | 6.6 | 2.4 | 8.3 | 7.3 | 0.7 | 0.2 | 0.5 |
| 21 | 2.9 | 1.2 | 3.2 | 4.6 | 7.0 | 80.1 | 0.3 | 0.5 | 0 | 0.3 |
| 28 | 0.8 | 0.4 | 0.4 | 2.5 | 2.0 | 93.0 | 1.0 | 0 | 0 | 0.2 |

The Tat-Myc and Tat-Bcl-2 treated cells express high levels of c-Kit and Sca-1, and are negative for lineage markers (Table 2).

TABLE 2

| Experiment # | c-Kit × Sca-1 | Mac-1 × Gr-1 | Flk2 | Ter119 |
|---|---|---|---|---|
| 1 | 99.3 | 1.5 | 0 | 0.2 |
| 2 | 99.2 | 1.1 | 0 | 0.9 |
| 3 | 93.0 | 0.4 | 0 | 0.2 |

Figure 3B:
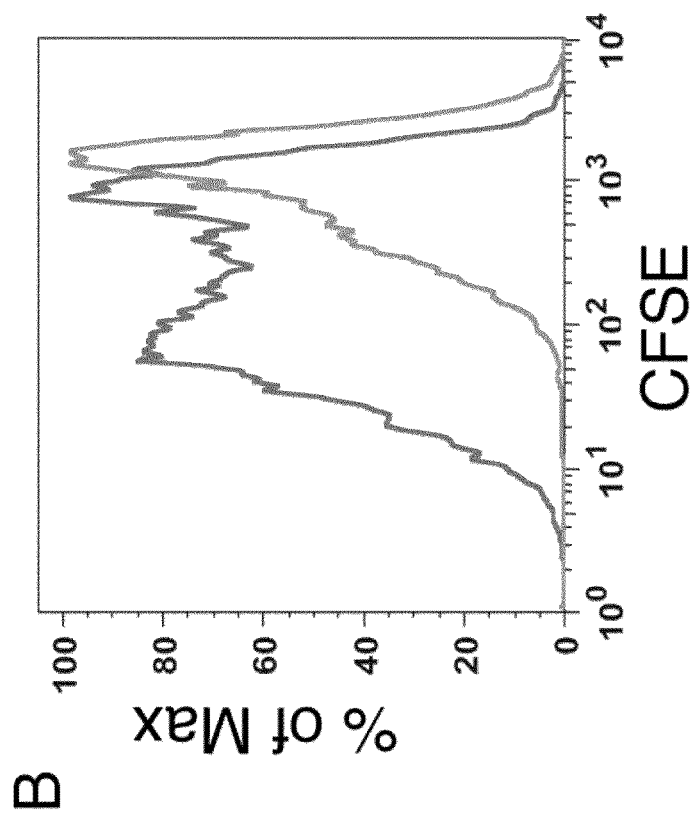
Figure 3C:
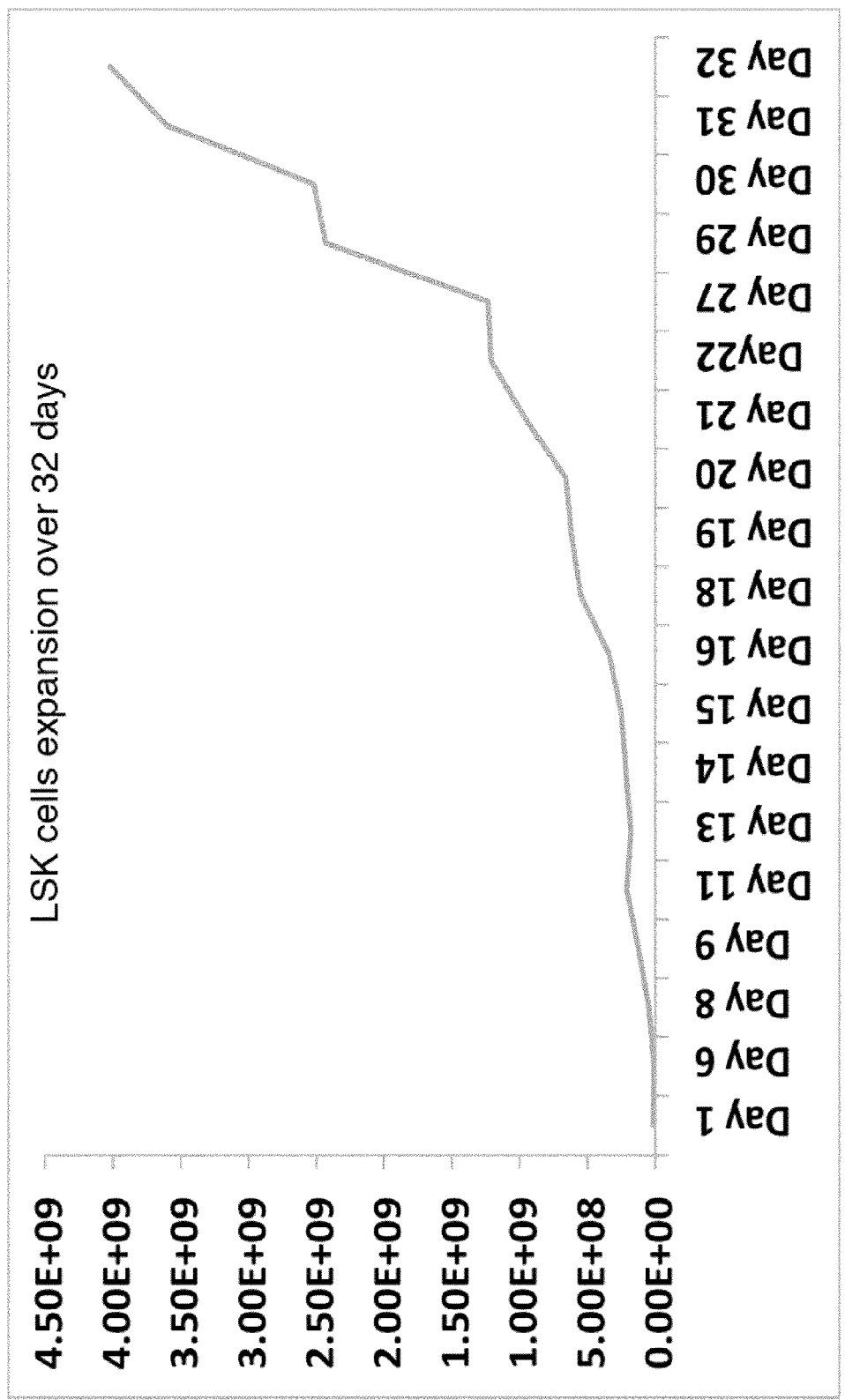

In addition, the labeling of a fraction of the cells with CFSE demonstrated that the HSCs actively proliferate when maintained under these culture conditions (FIG. 3B). The overall expansion profile of the HSCs is represented in FIG. 3C and Table 1, ultimately yielding a 269 fold expansion of murine HSCs over a 28 day period in culture.

Example 5

Transplantation of Tat-Myc and Tat-Bcl-2 Expanded Murine HSCs

Decreasing numbers of in vitro expanded HSCs were transplanted into sublethally irradiated Rag-1$^{-/-}$ mice. Transplantation into Rag1$^{-/-}$ mice (Jackson Laboratory) was carried out as described for NSG mice except Rag1$^{-/-}$ mice received 350 rads of radiation just prior to injection the BM cells via the tail vein.

Figure 4A:
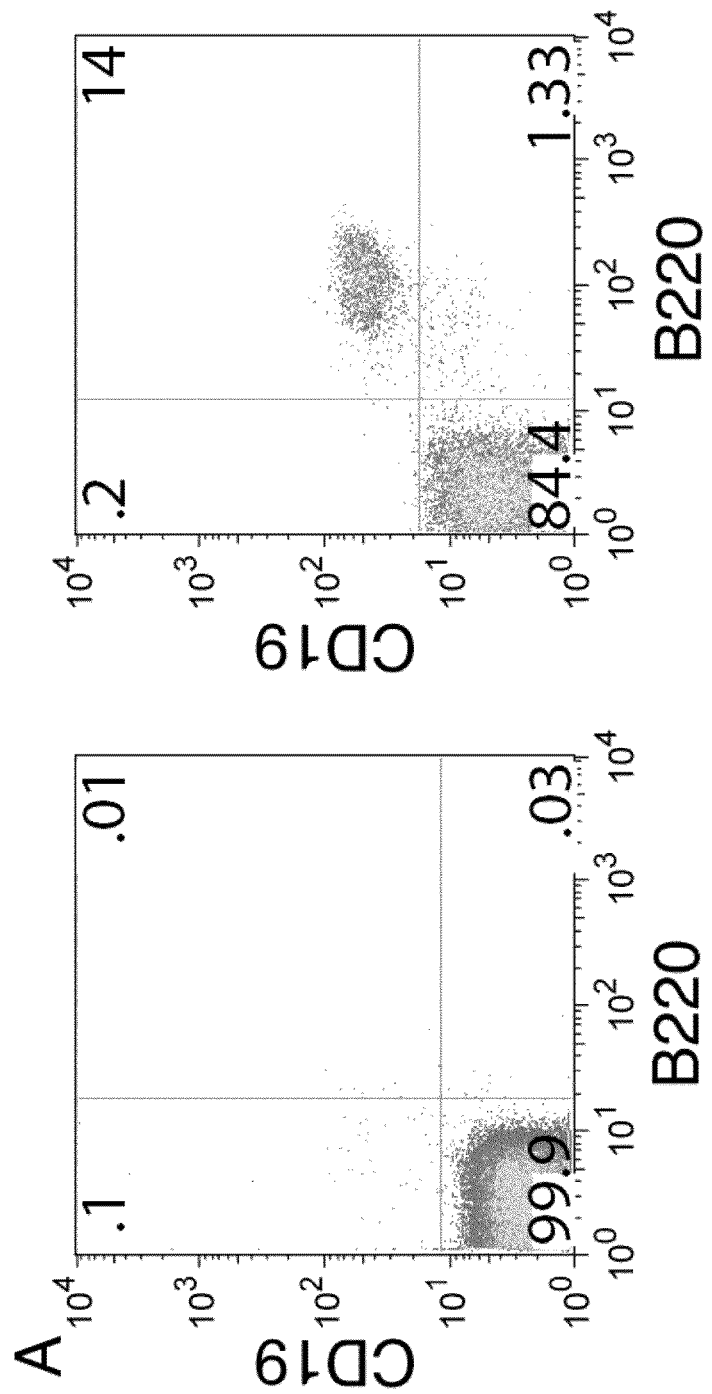
Figure 4B:
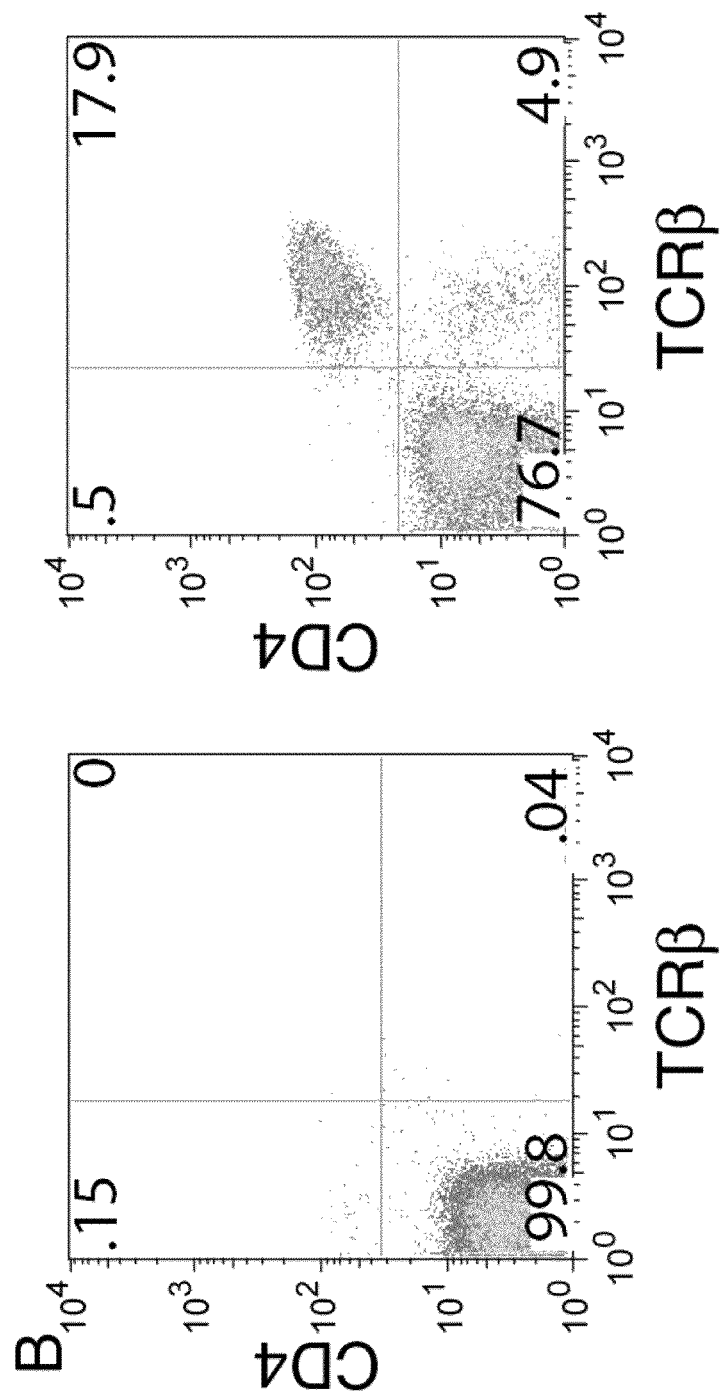

Four weeks post-transplant, the mice were examined for the presence of mature T- and B-cells. Mature B220/CD19 expressing B-cells and TCBB/CD4 expressing T-cells were present in the peripheral blood of HSC chimaeric mice following the transplantation of 10, 100 or 1000 in vitro expanded HSCs (FIGS. 4A, 4B and Table 3).

TABLE 3

| Number of BM cells transplanted | % T-cells | STDEV | % B-cells | STDEV |
|---|---|---|---|---|
| $10^3$ (n = 4) | 13.1 | 6.7 | 11.5 | 6.3 |
| $10^2$ (n = 5) | 15.3 | 5.0 | 11.0 | 4.1 |
| $10^1$ (n = 5) | 16.1 | 4.9 | 17.5 | 7.9 |
| Wild type (n = 4) | 16.5 | 5.7 | 20.3 | 5.9 |

Figure 4C:
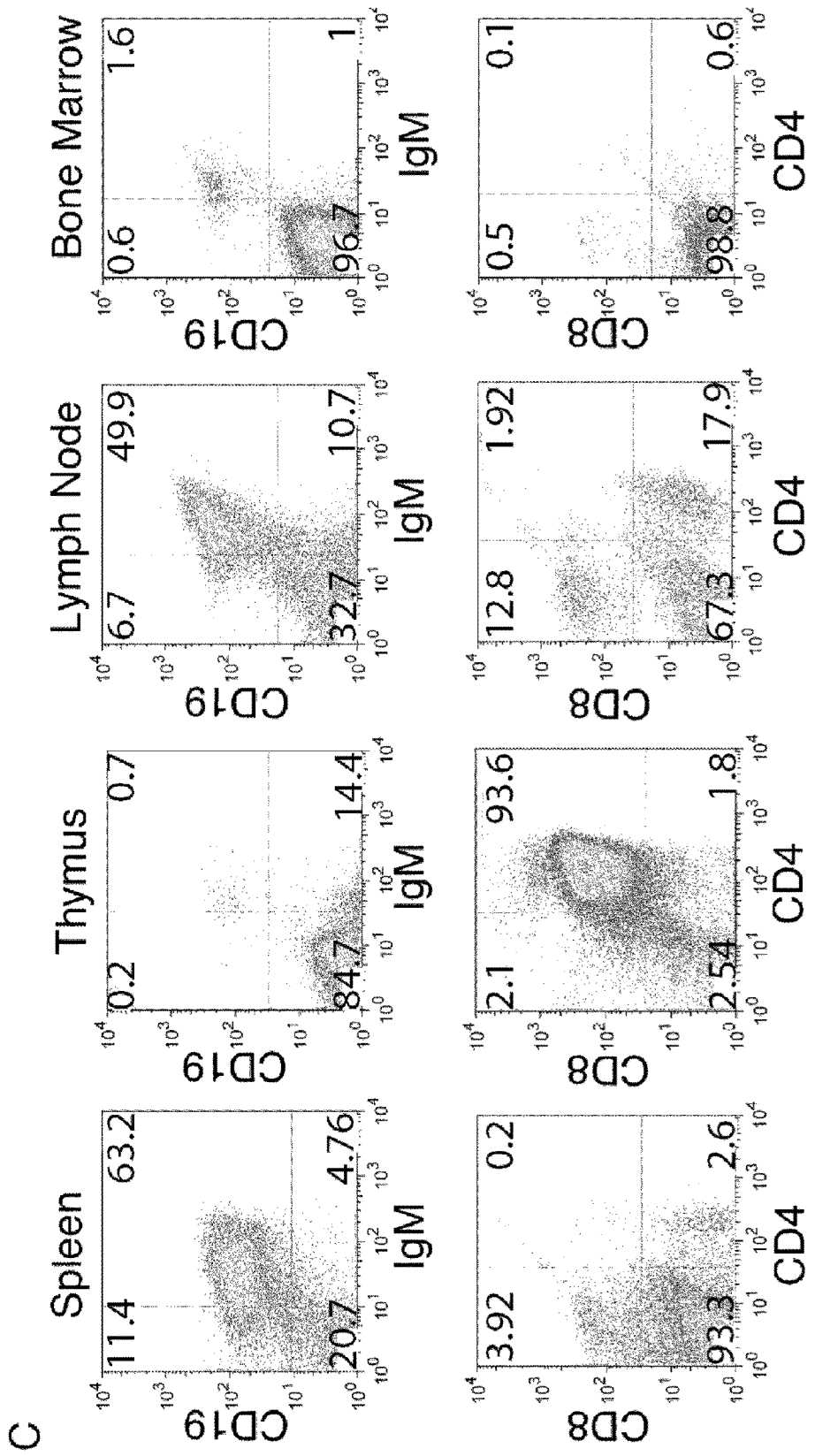

Mature T- and B-cells were also detected in the lymph nodes, spleen, thymus and bone marrow of HSC chimaeric mice (FIG. 4C).

Figure 4D:
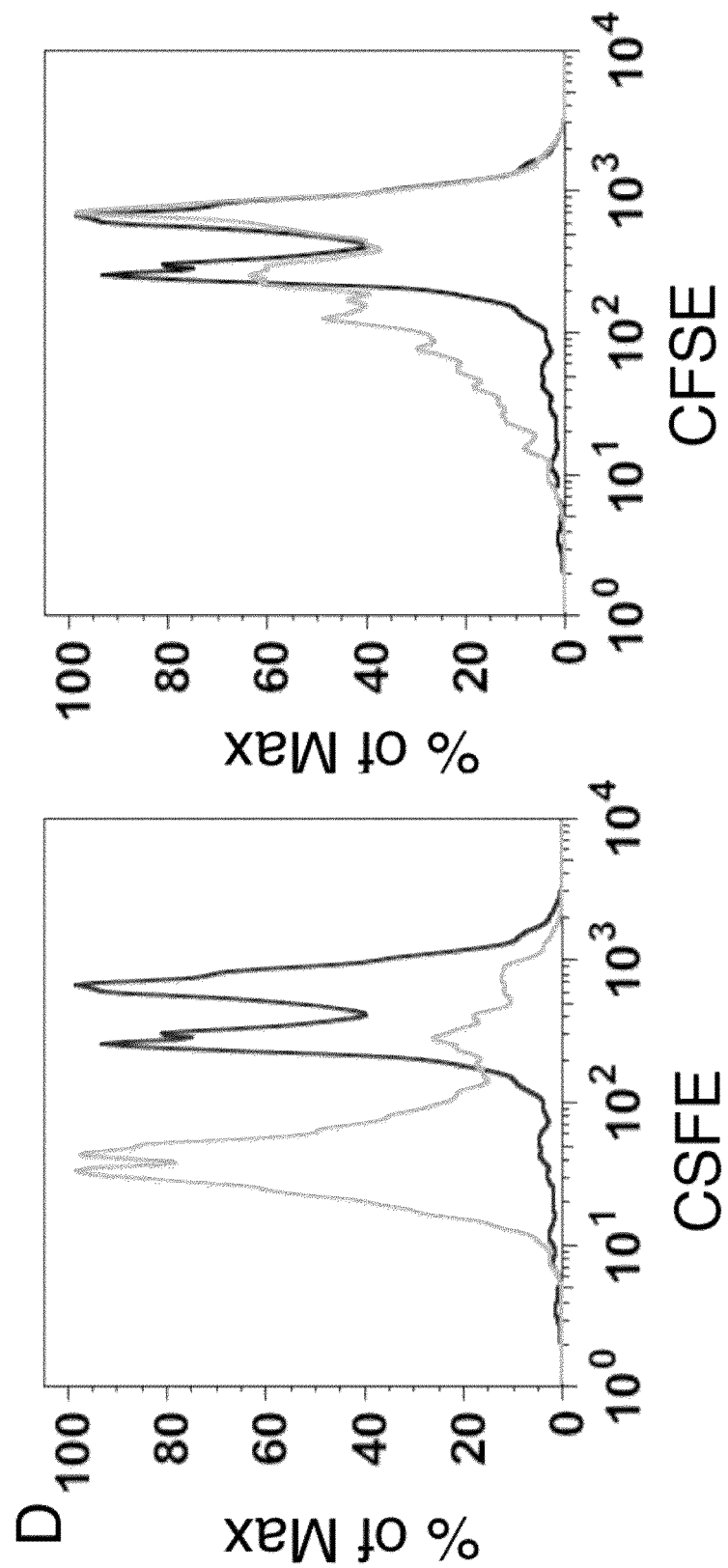

The mature murine T- and B-cells obtained from the spleen of chimaeric mice were labeled with CFSE and were activated with monoclonal antibodies to CD3 (T-cells) or CD40 and IgM (B-cells). The mature lymphoid cells were able to blast and undergo cell division following activation through their antigen receptors (FIG. 4D). In addition, bone marrow cells obtained from the initial set of HSC chimaeric mice were used for serial transplant studies. Table 4 shows the frequency of mature T- and B-cells detected in the peripheral blood of Rag-1$^{-/-}$ mice that were transplanted in a serial manner.

TABLE 4

| Serial Transplant | % T-cells | STDEV | % B-cells | STDEV |
|---|---|---|---|---|
| $1^{st}$ Transplant (n = 5) | 8.0 | 4.2 | 14.3 | 10.4 |
| $2^{nd}$ Transplant (n = 5) | 6.0 | 4.0 | 6.6 | 5.5 |
| $3^{rd}$ Transplant (n = 5) | 2.7 | 1.3 | 10.4 | 4.7 |

Example 6

Expansion of Human Cord Blood-Derived HSCs with Tat-Myc and Tat-Bcl-2

Fresh cord blood cells were obtained from samples that were discarded from a local cord blood bank. All human cells were de-identified and exempt from IRB oversight. Cord blood included O+, O−, A+, A−, B+, B−, and AB+ all of which showed approximately the same expansion profiles.

The total cord volume was split into 20 ml aliquots and diluted 1:1 in PBS. Diluted cord blood (20 mls) was gently overlaid on 20 mls of Ficoll-Paque Plus (Amersham Biosciences Cat #17-1440-03). The cells were spun at 900× gravity for 60 min. The buffy coat was removed with a glass pipette and was washed twice with PBS. The cells were resuspended in FCB media (Iscove's (Gibco) supplemented with 10% human plasma, 100 units per ml Penn/Strep, 30 ml of media containing SCF, IL3 and IL6 and 30 mls of media containing TPO, FLT3-L, and GM-CSF described above. FCB media was further supplemented with 5 µg/ml recombinant Tat-Myc, and 10 µg/ml recombinant Tat-Bcl-2 just prior to addition to the fetal cord blood (FCB) cells. The medium was replaced every 3 days over the course of the expansion.

Figure 5A:
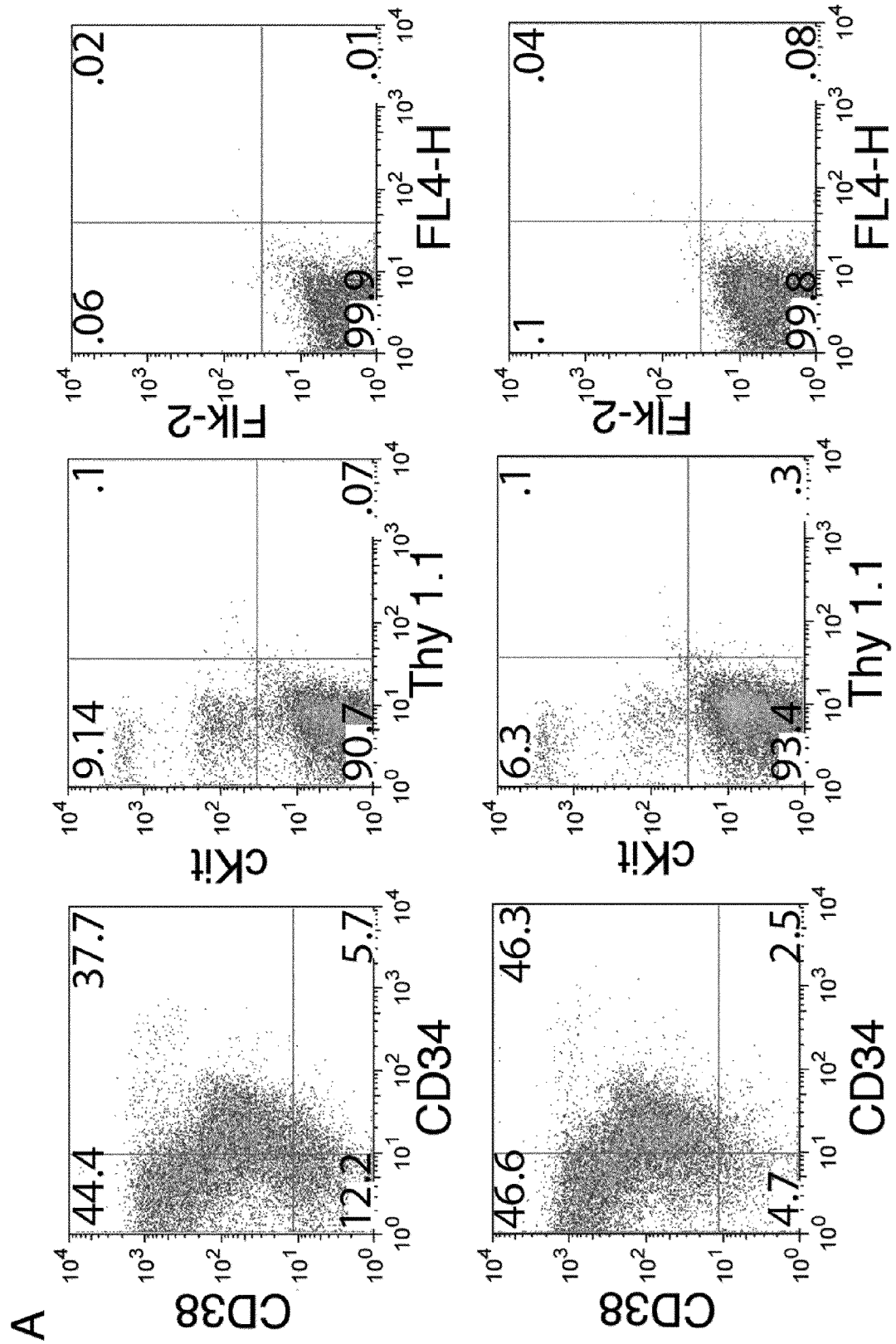
Figure 5A:
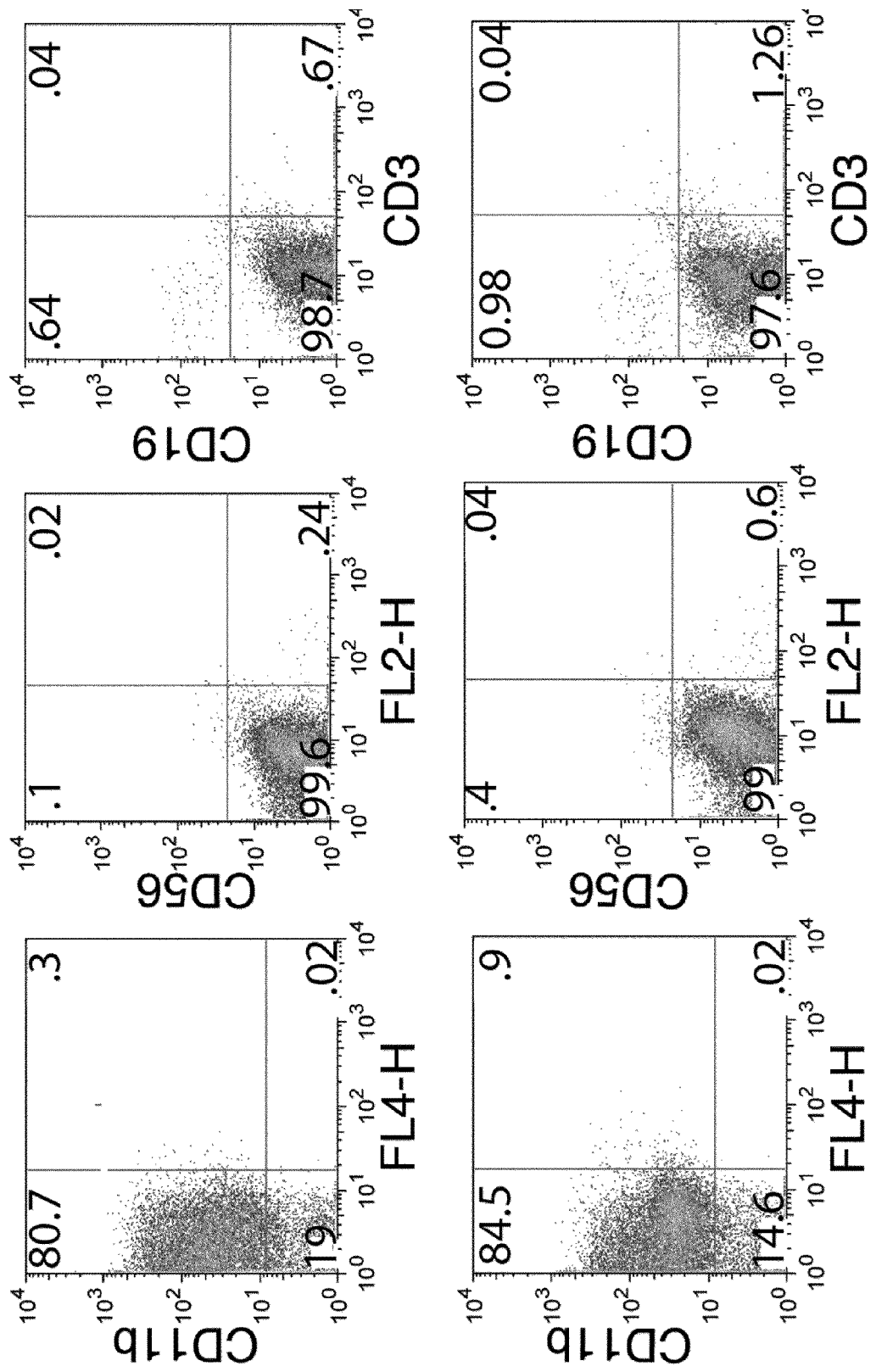
Figure 5B:
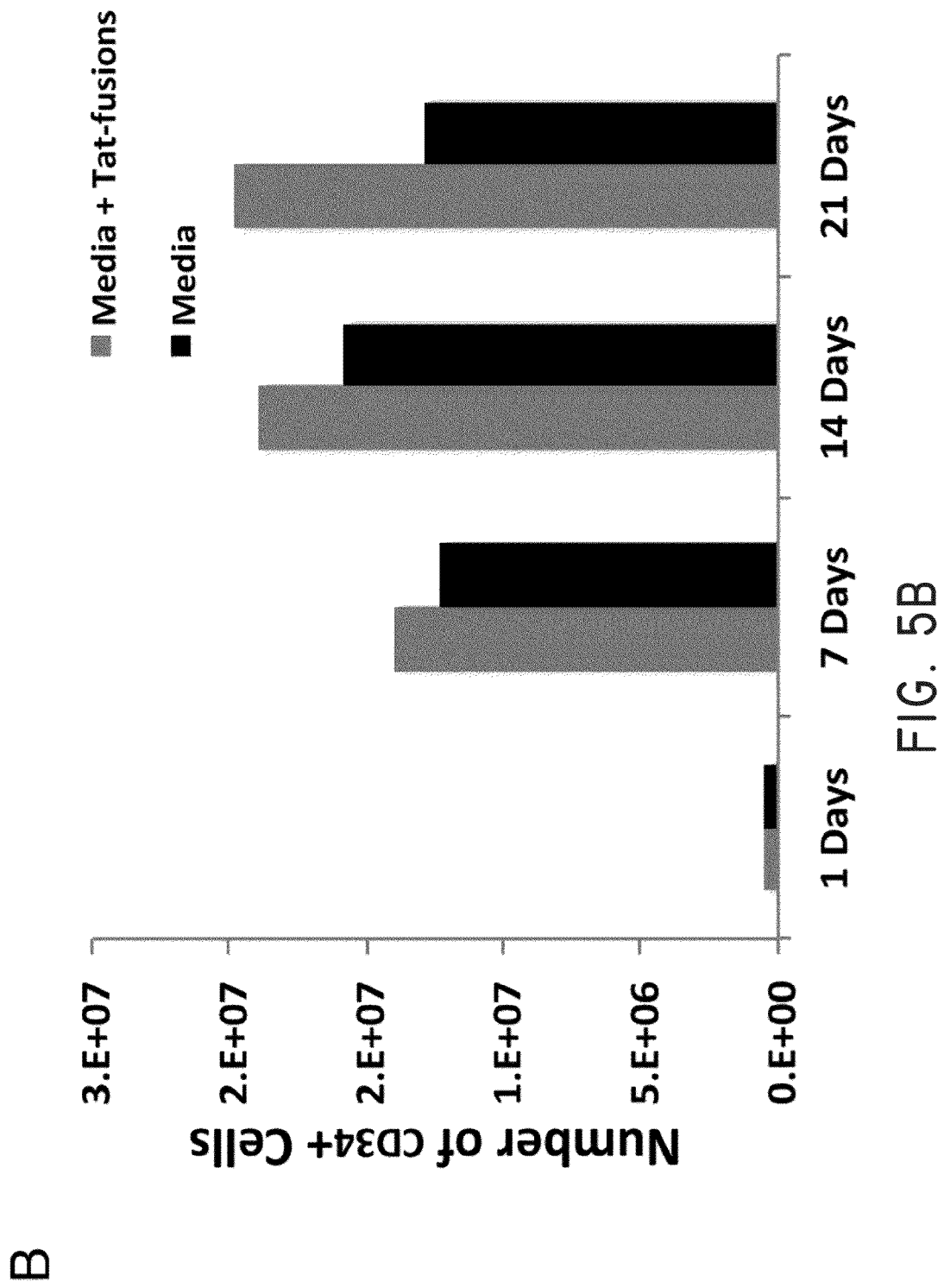

The cytokine cocktail contained IL3, IL6, TPO, Flt3-L, SCF, and GM-CSF which differs from previously reported media in the combination of these six cytokines (Suzuki, T., et al. (2006). Stem Cells 24, 2456-65.), as well as by the addition of recombinant Tat-Myc and Tat-Bcl-2. Evaluation of the surface phenotype of the in vitro expanded human HSCs showed that the human HSCs retain their surface characteristics after extended culture in the presence of Tat-Myc and Tat-Bcl-2 (FIG. 5A). This set of conditions resulted in 86.4 fold increase in the number of CD34+ cells in 14 days of culture, and 103.8 fold increase in the number of human CD34+ cells derived from unfractionated cord blood in 21 days of culture (FIG. 5B).

Example 7

Figure 5C:
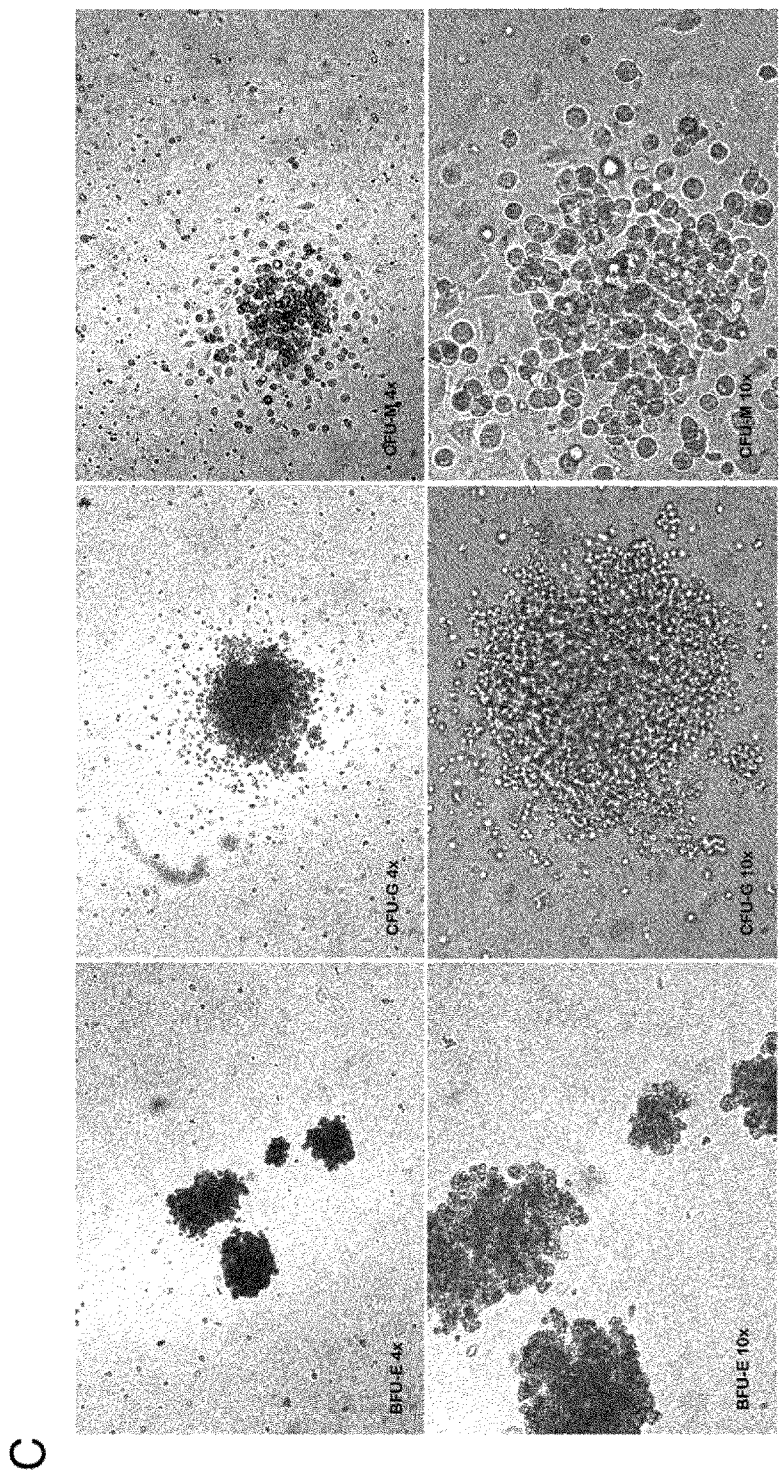
Figure 5D:
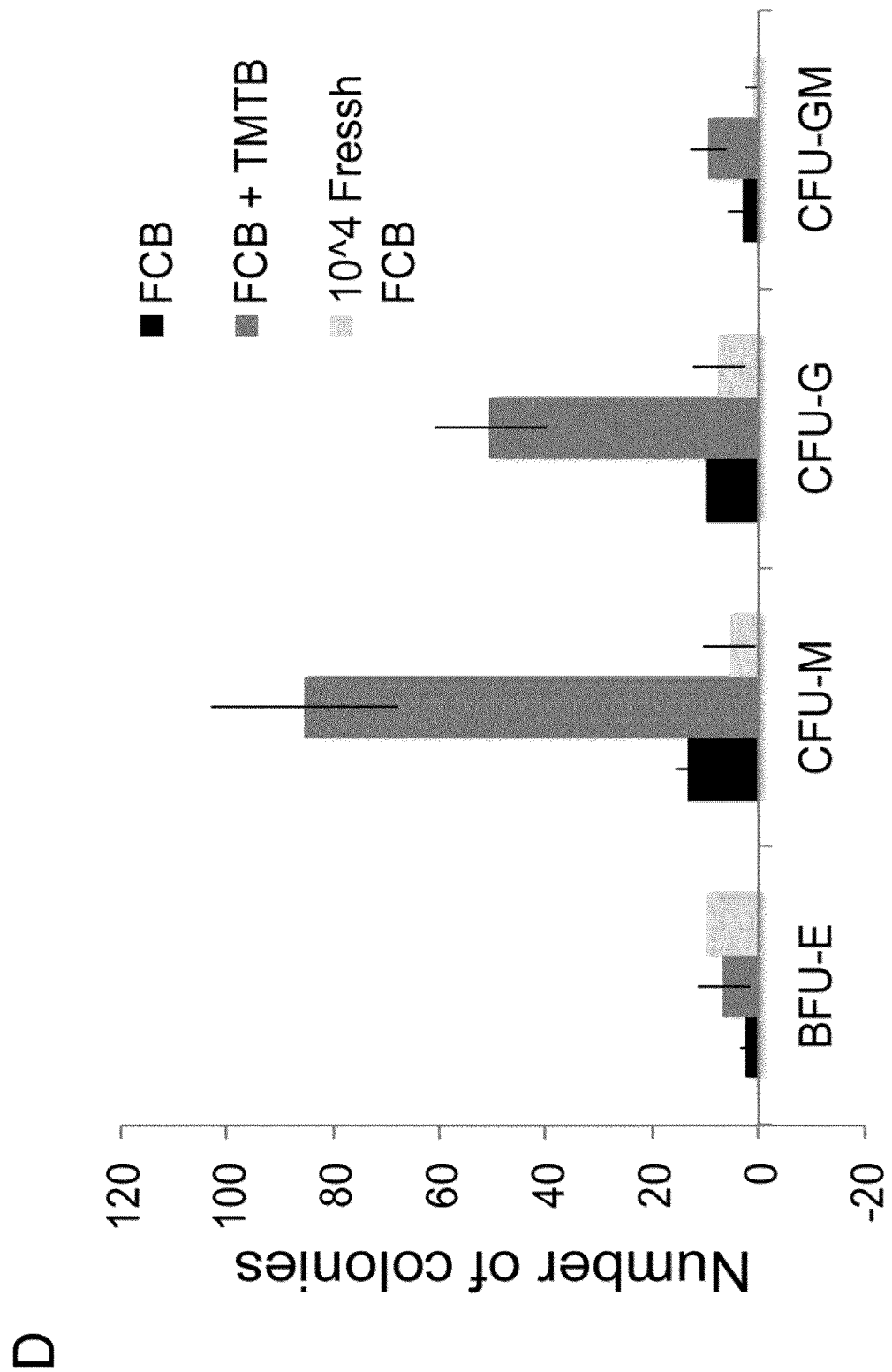
Figure 5E:
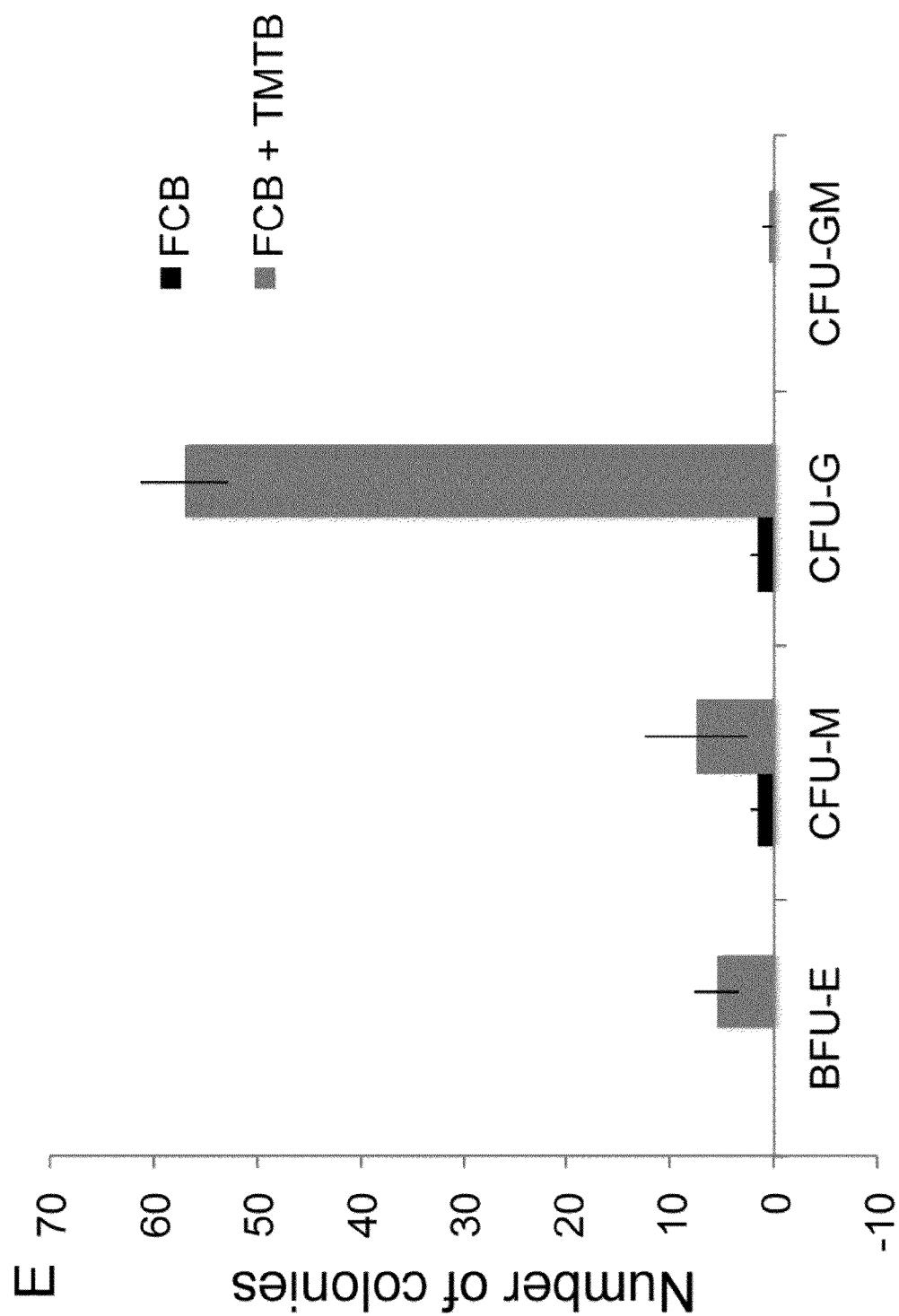

Tat-Myc and Tat-Bcl-2 Expanded Human CB HSCs are Biologically Active in Vitro and In Vivo The in vitro expanded human HSCs were plated on MethoCult Optimum (StemCell Technologies), and were examined for their ability to give rise to specific colony types. The in vitro expanded human HSCs are able to give rise to CFU-G, CFU-M, CFU-GM and BFU-E colonies (FIGS. 5C and 5D). In addition, while the surface phenotype of the HSCs expanded in the presence of Tat-Myc and Tat-Bcl-2 was preserved in culture, their colony-forming unit content was significantly enriched under these conditions (FIG. 5D). The CD34+ cells expanded in the presence of Tat-Myc and Tat-Bcl-2 were also able to give rise to new BFU-E, CFU-M, CFU-G and CFU-GM colonies, whereas the CD34+ cells cultured in media alone did not generate new colonies (FIG. 5E).

NOD/SCID/gc-/- mice (NSG) mice were used as recipients for experiments to test the ability of the human CD34+ cells expanded in vitro to give rise to mature human hematopoietic lineages in vivo. This is a documented mouse model useful for this purpose (Tanaka, S., et al. (2012). Development of mature and functional human myeloid subsets in hematopoietic stem cell-engrafted NOD/SCID/IL2rgKO mice. J Immunol 188, 6145-55.).

Fetal cord blood cells (FCBs) were injected into NOD/SCID/gc-/- mice (NSG) mice (Jackson Laboratory) that received 180 rads of radiation just prior to injection. Expanded FCBs were washed 3 times in PBS and injected via the tail vein in 200 µl PBS. Eight weeks post-transplant, the mice were bled via the tail vein to assess reconstitution by flow cytometry using the following antibodies: anti-human CD3 (hCD3) (Biolegend Cat #300312), anti-human CD19 (hCD19) (Biolegend Cat #302208) and anti-human CD45 (hCD45) (Biolegend Cat #304028).

Figure 6A:
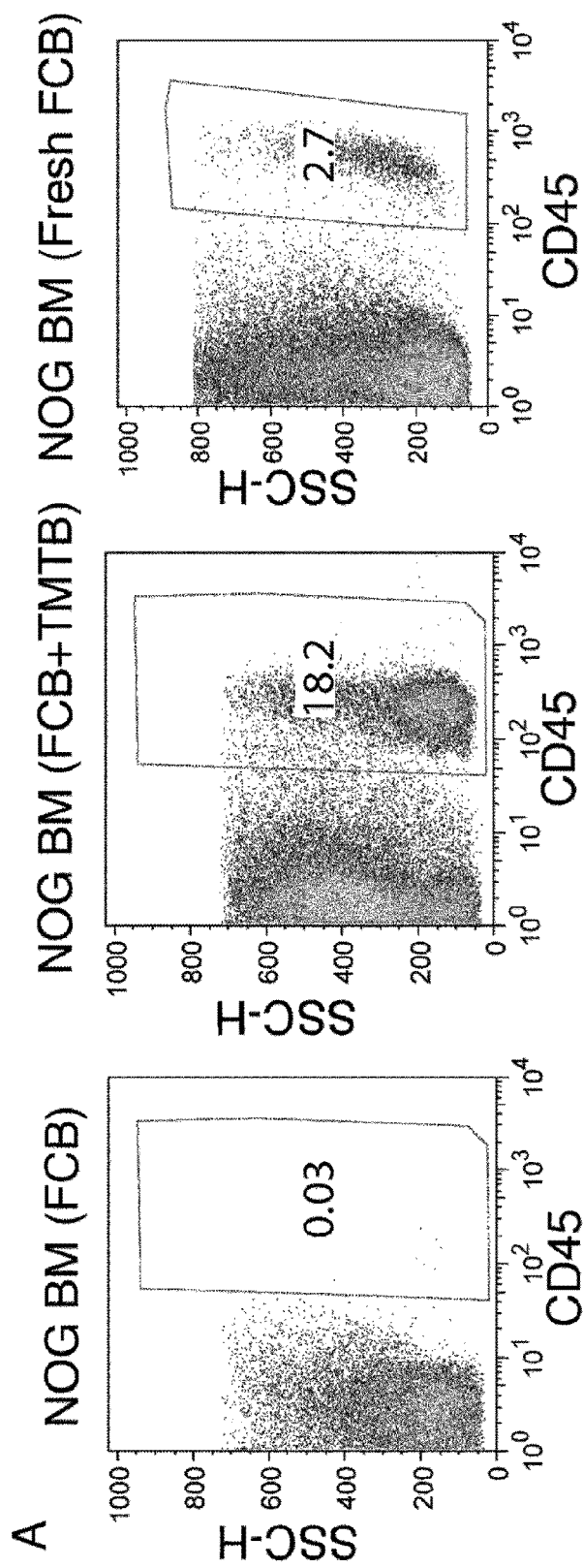
Figure 6B:
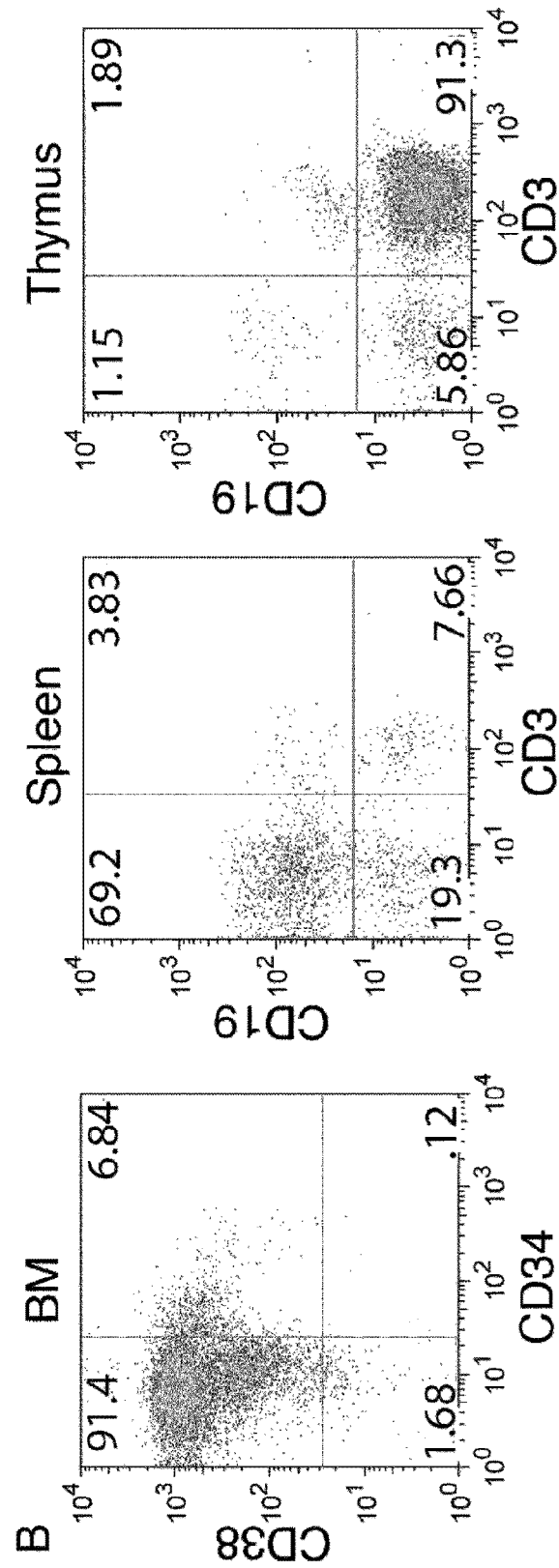

Short term development of human CD45+ expressing T and B cells in NSG chimaeric mice generated with $1\times10^7$ unfractionated cord blood cells was observed. However, the introduction of $1\times10^6$ protein-transduced long-term (ptlt)-HSC generated in vitro by culture with Tat-Myc and Tat-Bcl-2 for 14 days resulted in a higher frequency of human CD45+ cells in xenochimaeric NSG mice. In addition, human CD45+ cells could be observed in the peripheral blood of the mice for up to 20 weeks post transplant (FIG. 6A). Human CD45+, CD34+ CD38lo HSCs were found in the bone marrow (FIG. 6B), human CD45+/CD3+ and human CD45+/CD19+ lymphoid cells were found in the spleen, and human CD45+, CD3+ lymphoid cells were found in the thymus of xenochimaeric mice.

Figure 6C:
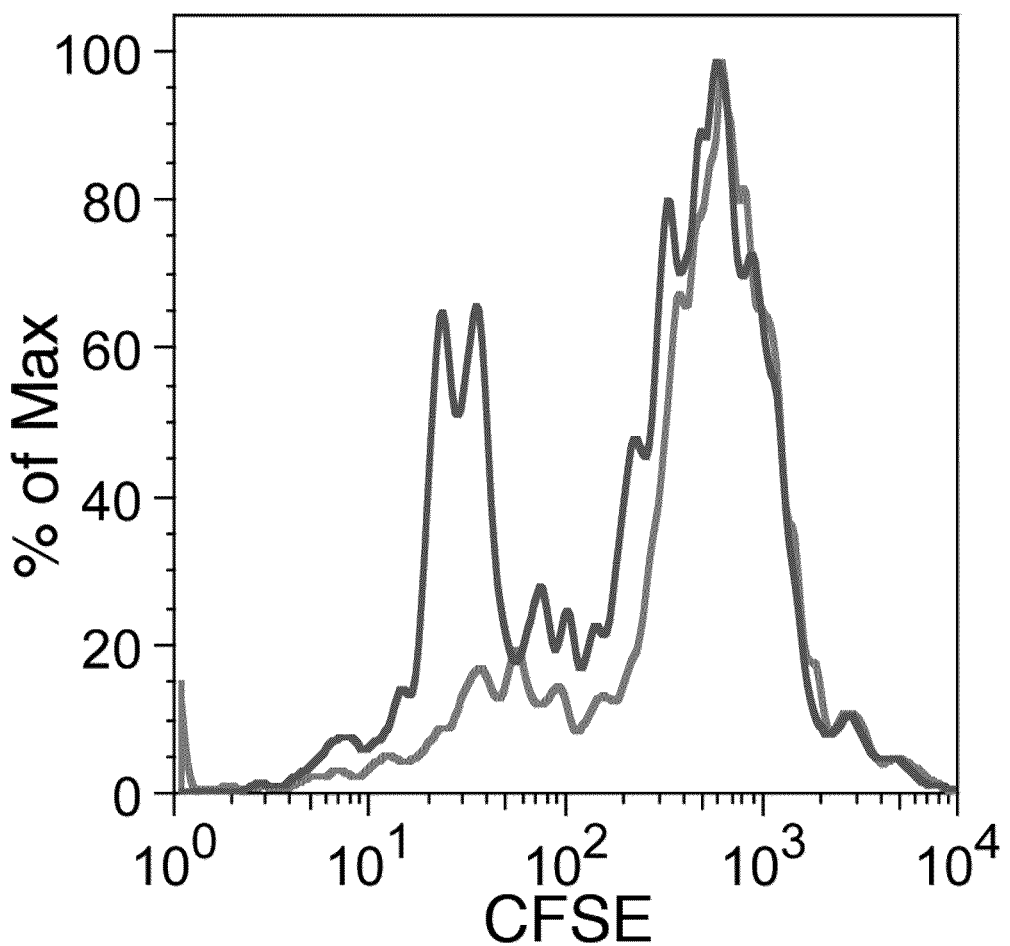

Human CD45+ CD19+ cells from the spleens of xenochimaeric NSG mice were labeled with CFSE, and were activated with monoclonal antibodies to human CD40 and IgM. The cells were analyzed at 72 hours by flow cytometry for dilution of CFSE. FIG. 6C shows the proliferation profile of the human B-cells that developed in vivo in xenochimaeric NSG mice.

Figure 6D:
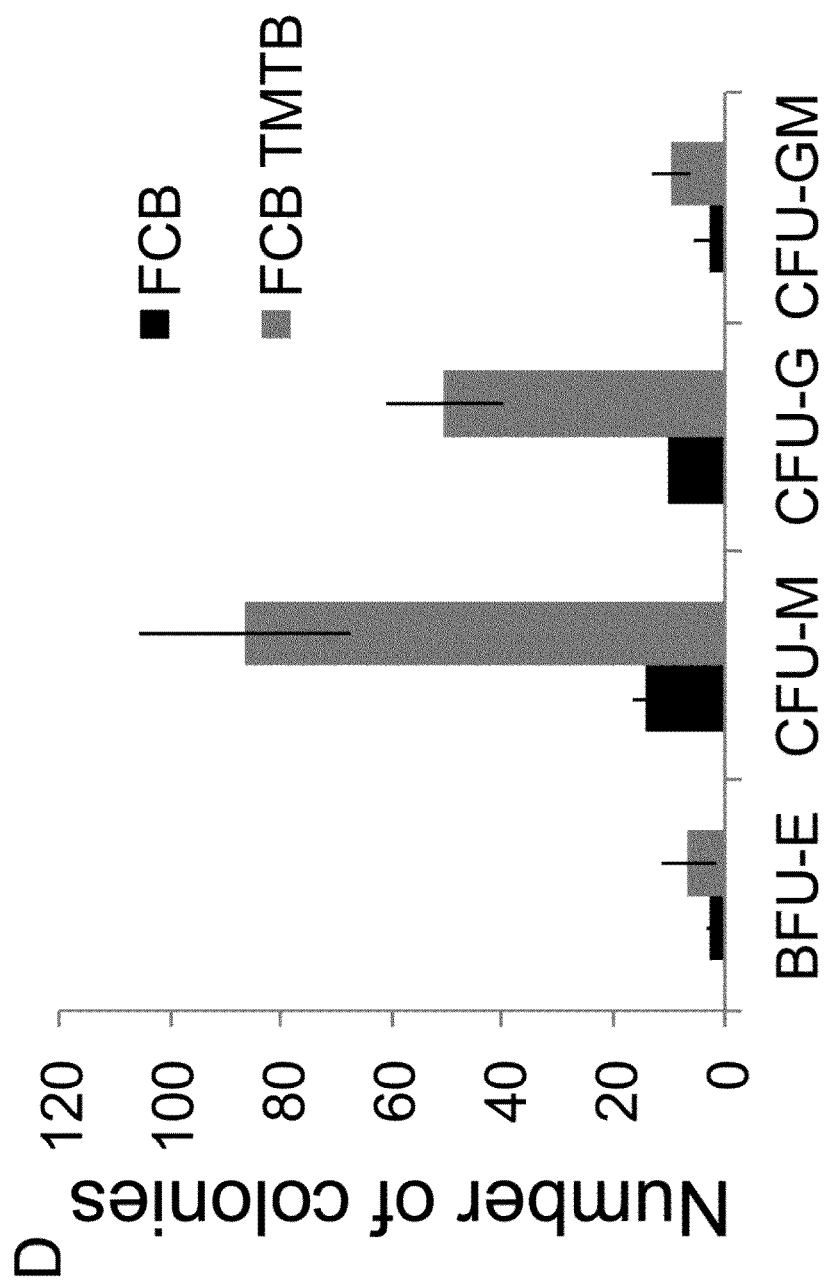
Figure 6E:
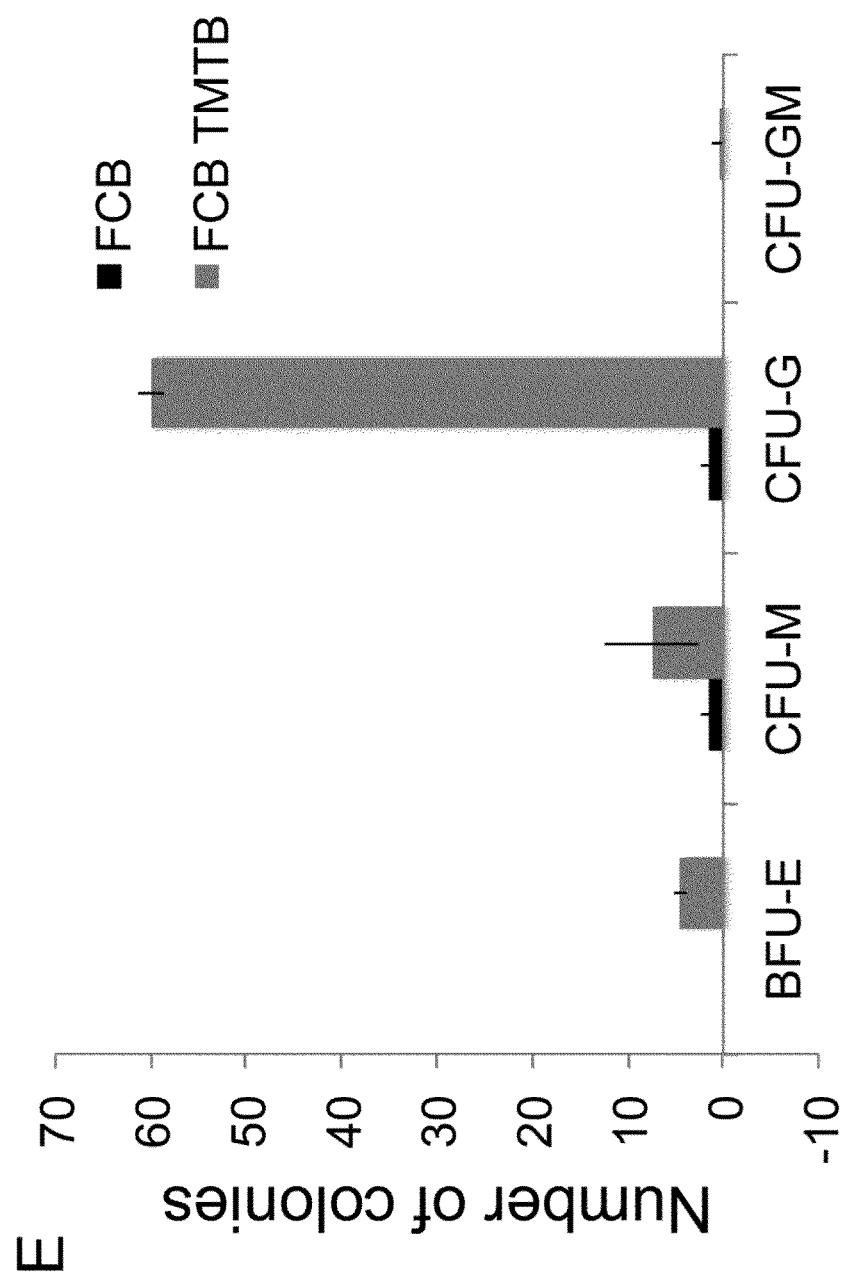

Human CD45+, CD34+ CD38lo HSCs from the bone marrow of xenochimaeric NSG mice were used to seed in MethoCult Optimum. These cells gave rise to colonies in MethoCult plates (FIG. 6D), and some of the colonies could still be observed following serial replating (FIG. 6E). The number of colonies in both instances was significantly higher for NSG mice reconstituted with human cord blood cells cultured for 14 days with Tat-Myc and Tat-Bcl-2 than for cells obtained from NSG mice reconstituted with fresh, un-manipulated human cord blood cells.

Figure 6F:
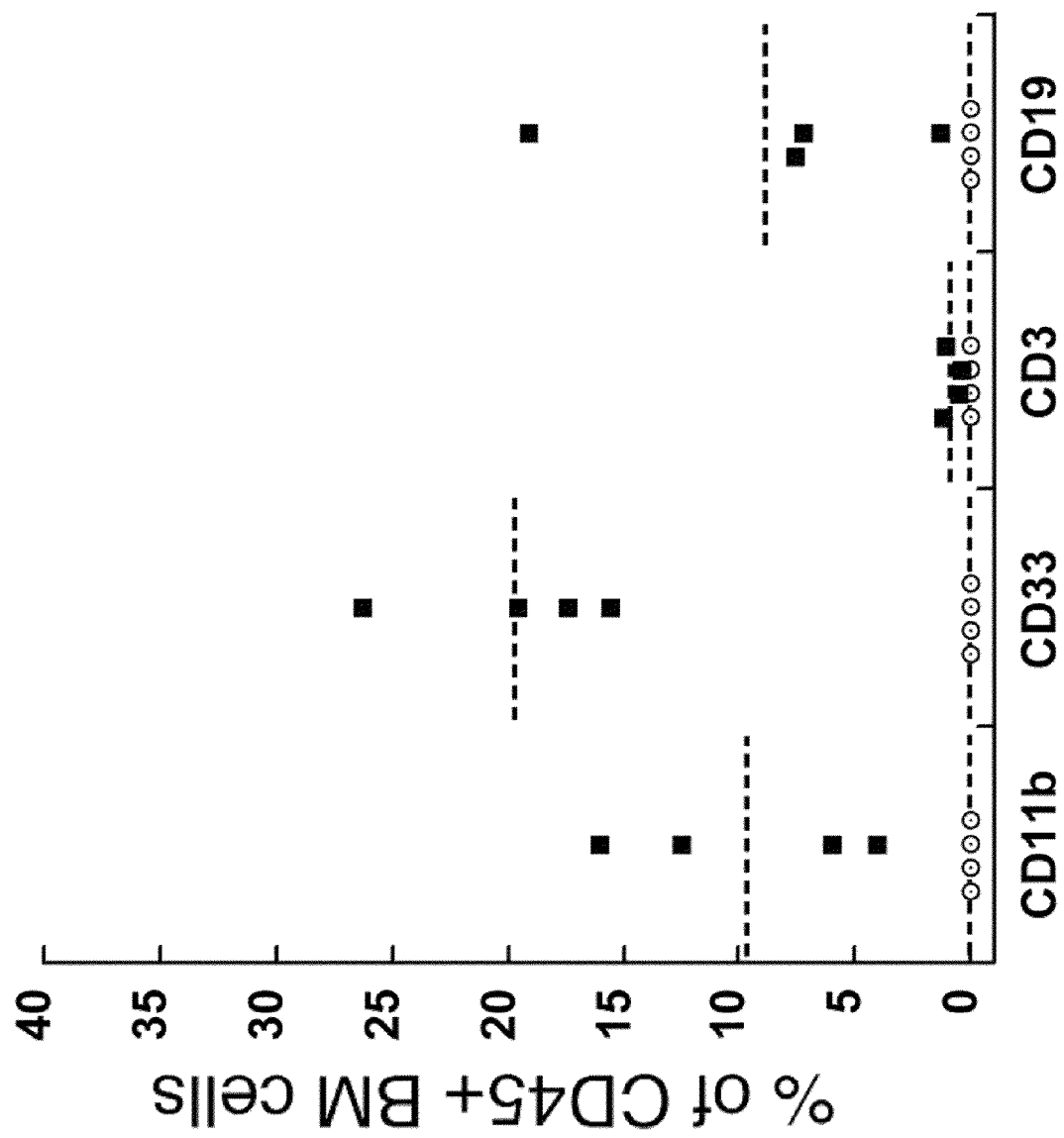
Figure 6G:
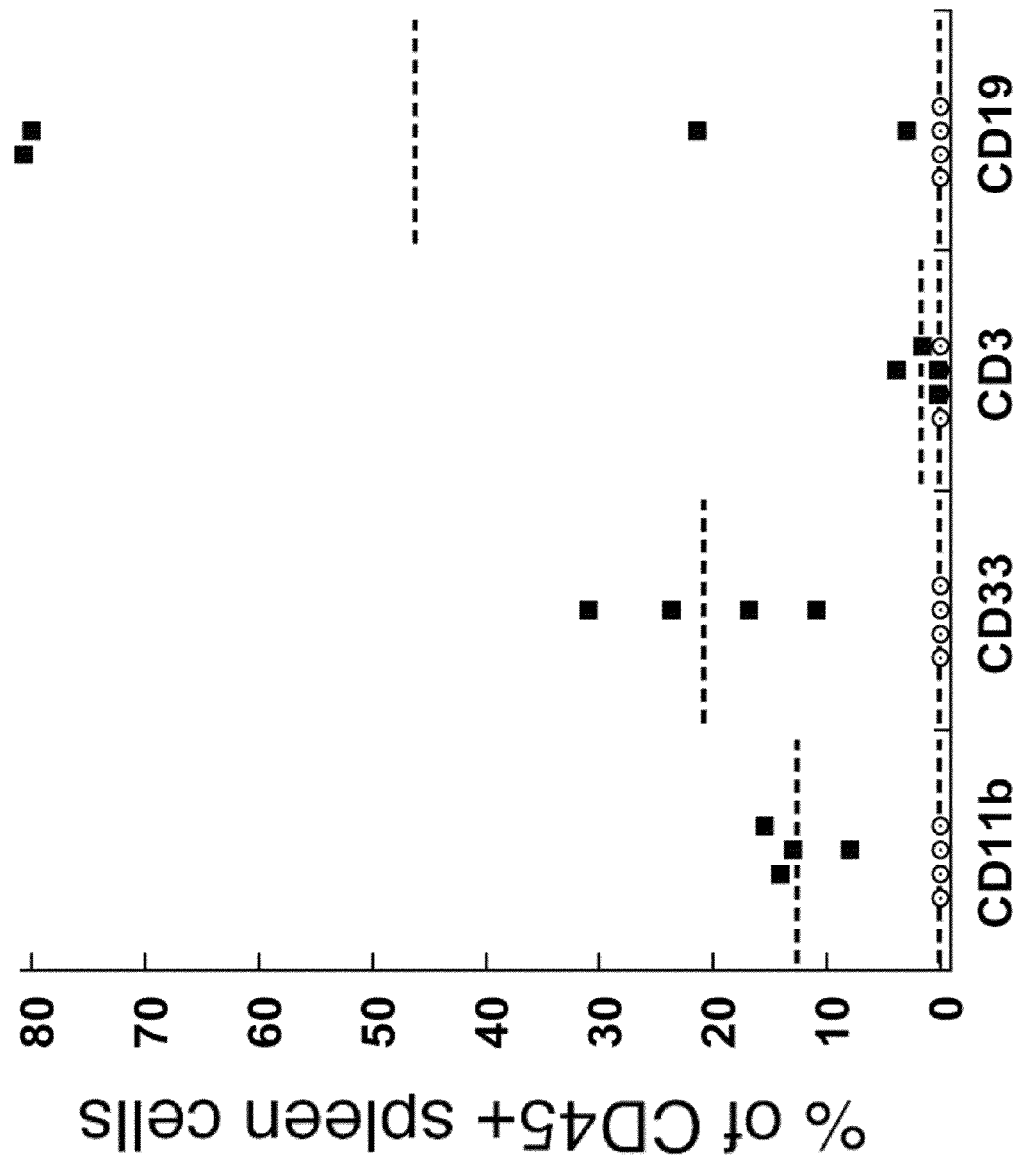

In addition, a cohort of xenochimaeric mice, engrafted with 106 cord blood cells previously expanded in vitro in a cocktail of cytokines supplemented with Tat-Myc and Tat-Bcl-2 (black squares), were assessed for myeloid and lymphoid cell differentiation. The CD45 positive population of bone marrow cells (FIG. 6F) and spleen cells (FIG. 6G) were analyzed for CD11b, CD33, CD3, and CD19 expression. Both myeloid and lymphoid cell differentiation was observed in the bone marrow and spleen of these xenochimaeric mice.

Example 8

Expansion of Human G-CSF Mobilized Peripheral Blood HSCs with Tat-Myc and Tat-Bcl-2

G-CSF mobilized cells were received in a 1 ml volume of elutriated blood from 5 patients who underwent G-CSF mobilization for autologous HSC transplantation. All G-CSF samples were de-identified and no further identifying information was associated with the cells used for these studies. The cells were added drop wise to 10 ml of FCB media. The cells were washed twice in FCB media and treated with 5 µg/ml recombinant Tat-Myc and 10 µg/ml recombinant Tat-Bcl-2 in a 10 ml volume. Cells ($5\times10^6$) were seeded in the G-Rex 100 cell expansion device (Wilson Wolf Manufacturing) according to the manufacturer's recommendation.

Figure 7A:
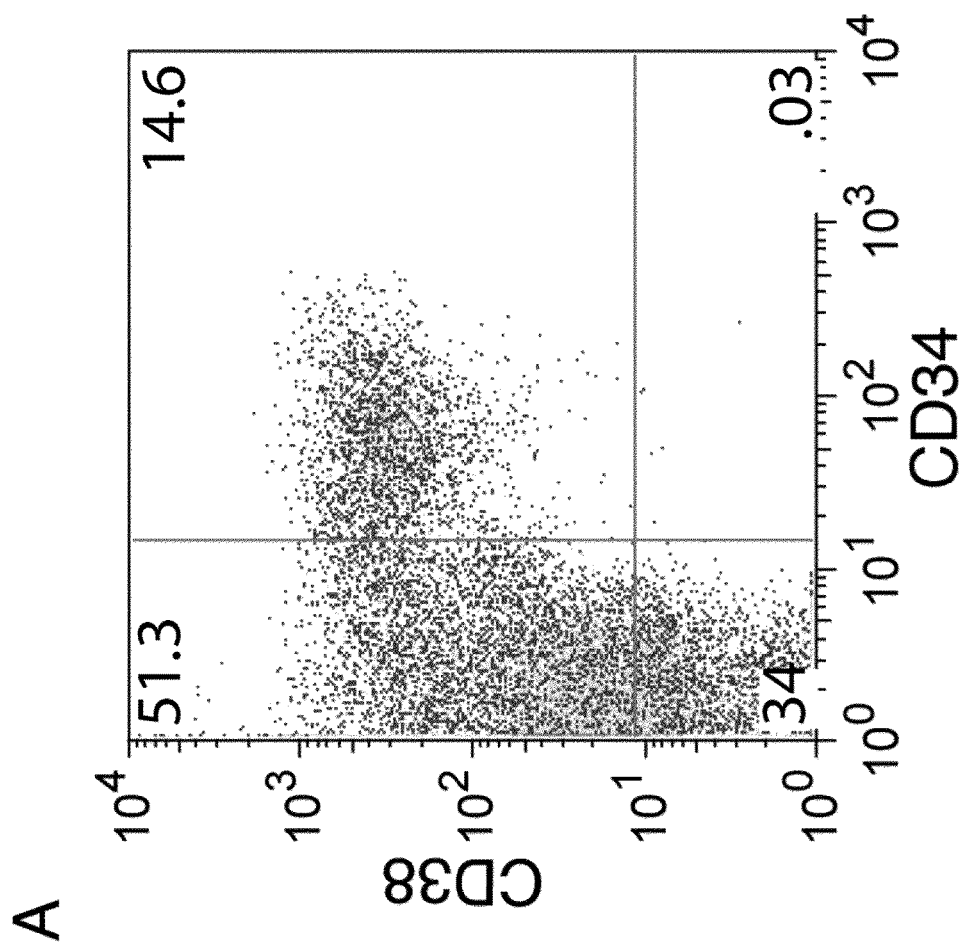
Figure 7B:
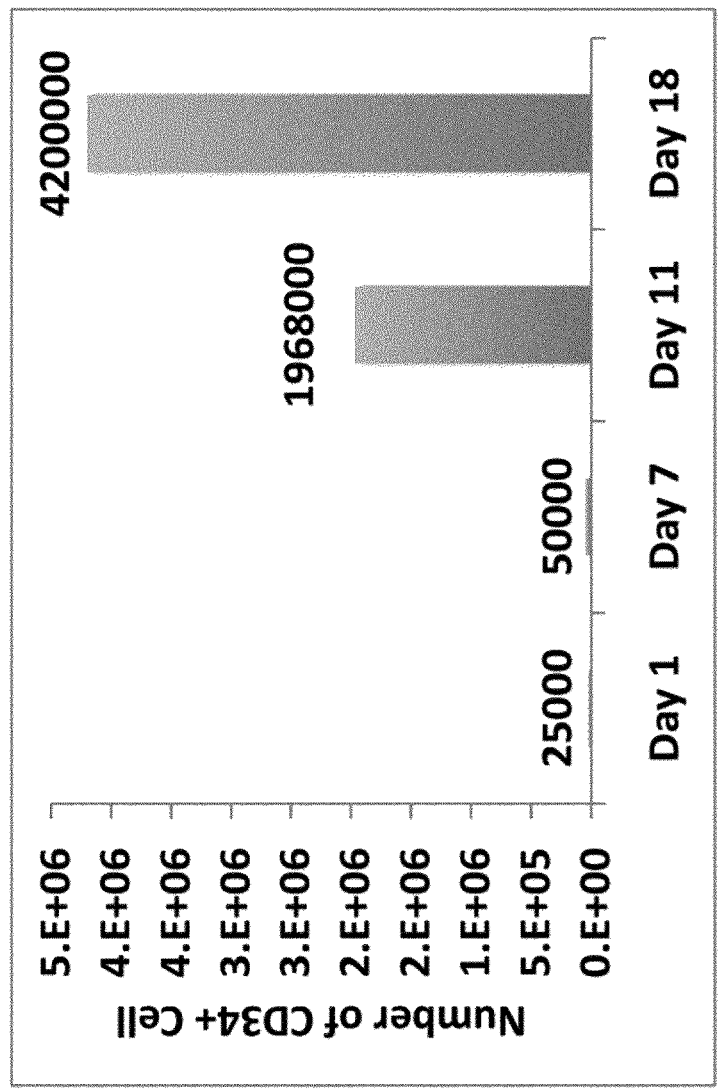

The cells were expanded in media supplemented with cytokines plus Tat-Myc and Tat-Bcl2 14 days. The FACS profile of the expanded HSCs shows a distinct population of hCD45+, CD34+, CD38hi, CD133+ cells (FIG. 7A). The kinetics of cell expansion are illustrated in FIG. 7B.

Figure 7C:
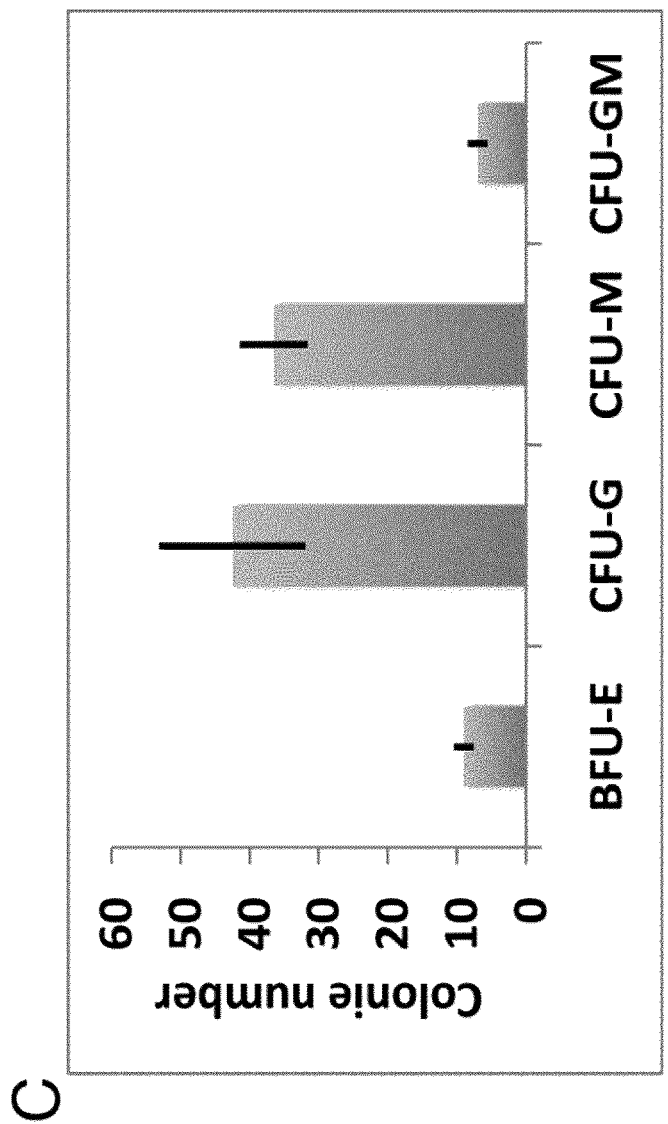

The expanded adult GCS-F mobilized HSCs were then plated on MethoCult Optimum in order to characterize their differentiation potential in vitro. The four colony types normally observed in the media that supports myeloerythroid differentiation were obtained (FIG. 7C), and some of these colony types were also observed upon serial replating.

Figure 7D:
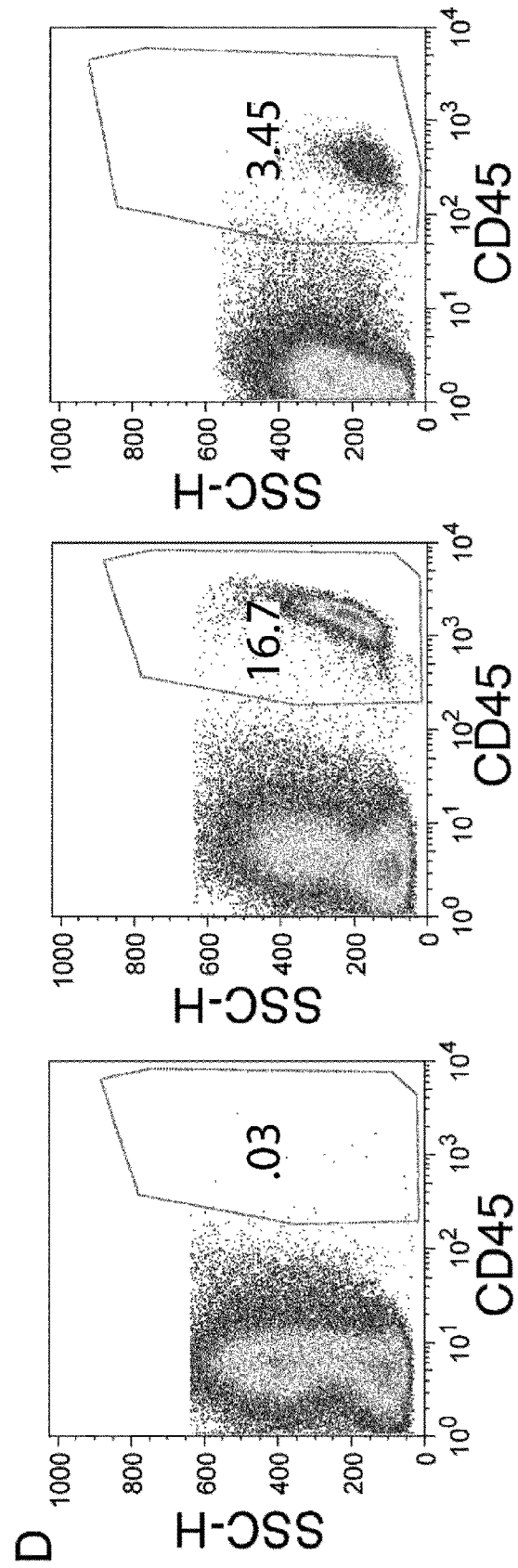

The expanded adult HSCs were able to reconstitute sublethally irradiated NSG mice. FIG. 7D shows a FACS analysis of the CD45+ staining of bone marrow from NSG mice transplanted 12 weeks earlier with either 106 expanded G-CSF and Tat-Myc/Tat-Bcl-2 mobilized HSCs (first panel) or $5\times10^6$ fresh un-manipulated cord blood cells (second panel).

Figure 7E:
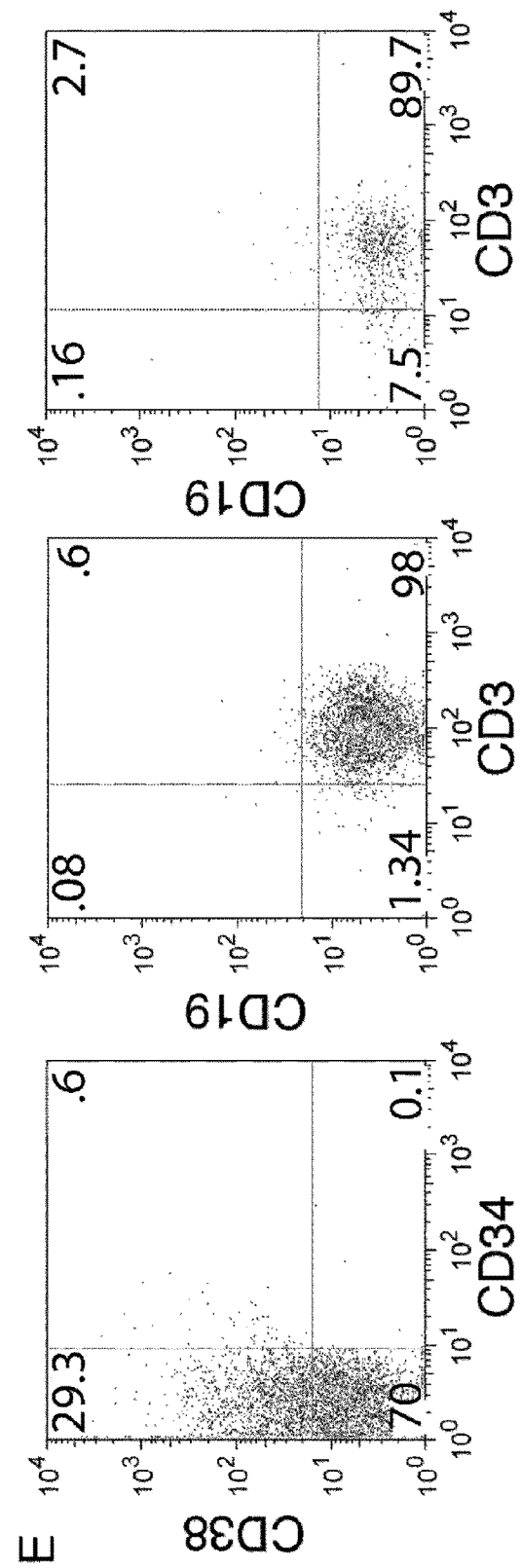

The NSG xenochimaeric mice generated with G-CSF mobilized cells cultured with Tat-Myc and Tat-Bcl-2 were euthanized, and bone marrow, spleen and thymus were collected for further analysis. The analysis of lymphoid organs from xenochimaeric NSG mice reconstituted with expanded adult HSCs showed that there were human CD45+, CD34+ CD38lo cells in the bone marrow (FIG. 7E, first panel), human CD45+, CD3+ lymphoid cells in the spleen (FIG. 7E, second panel) and thymus (FIG. 7E, third panel) of those mice. Together, these data demonstrate that one can successfully expand the HSC population obtained from human G-CSF mobilized adult blood.

Figure 7F:
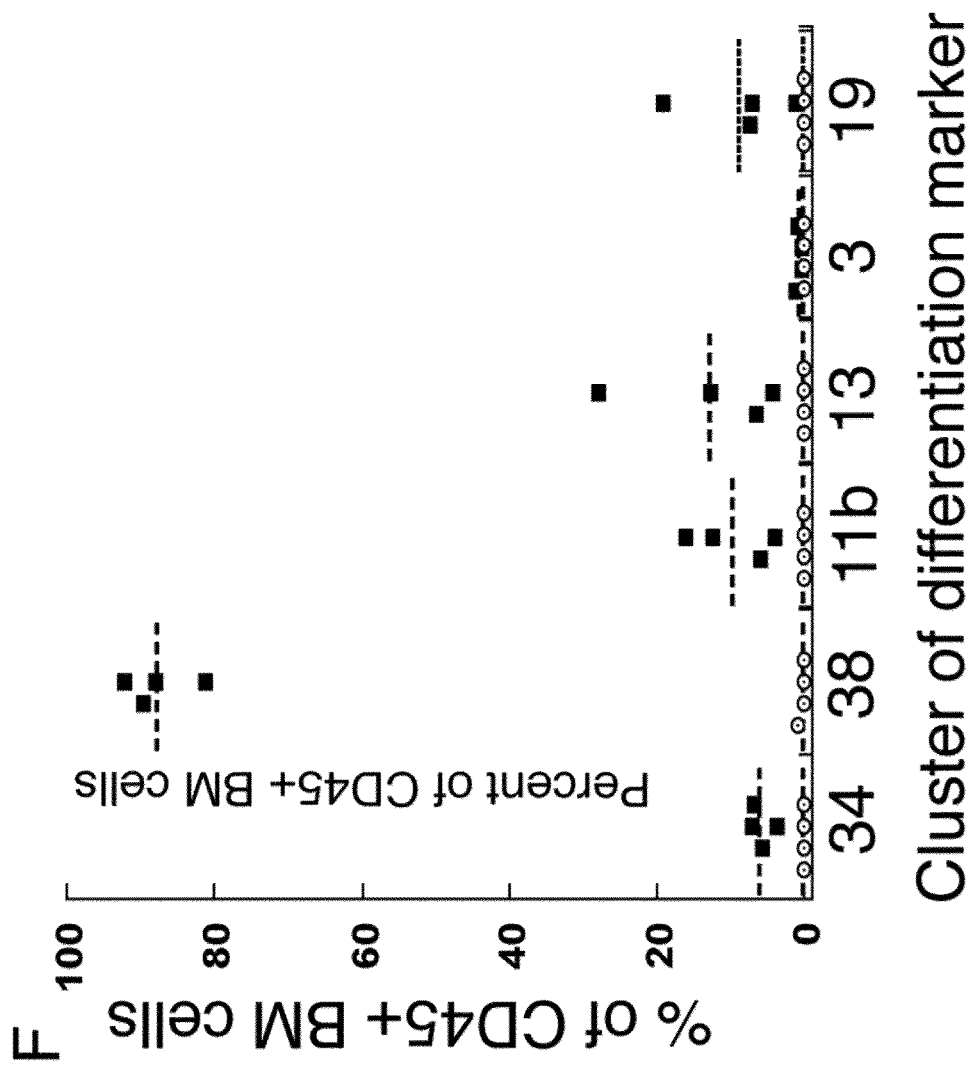
Figure 7G:
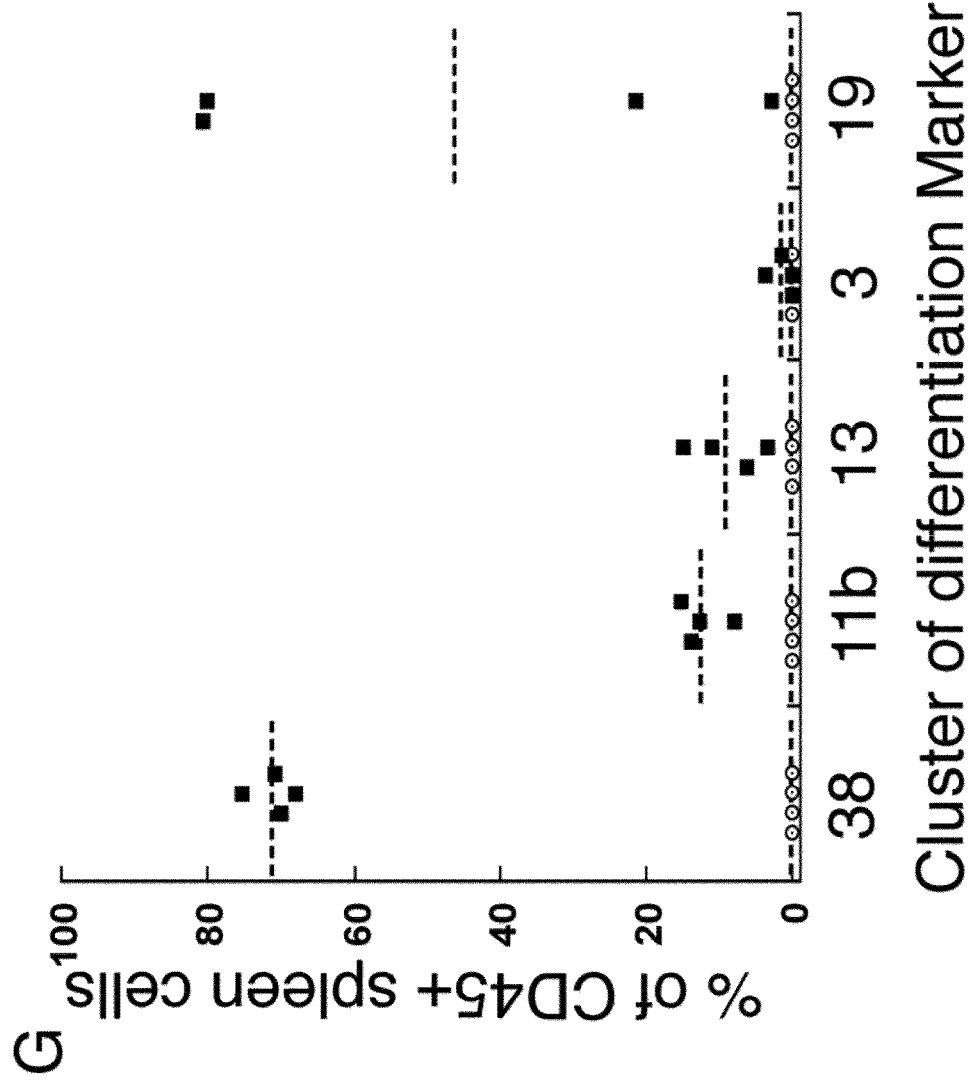
Figure 8:
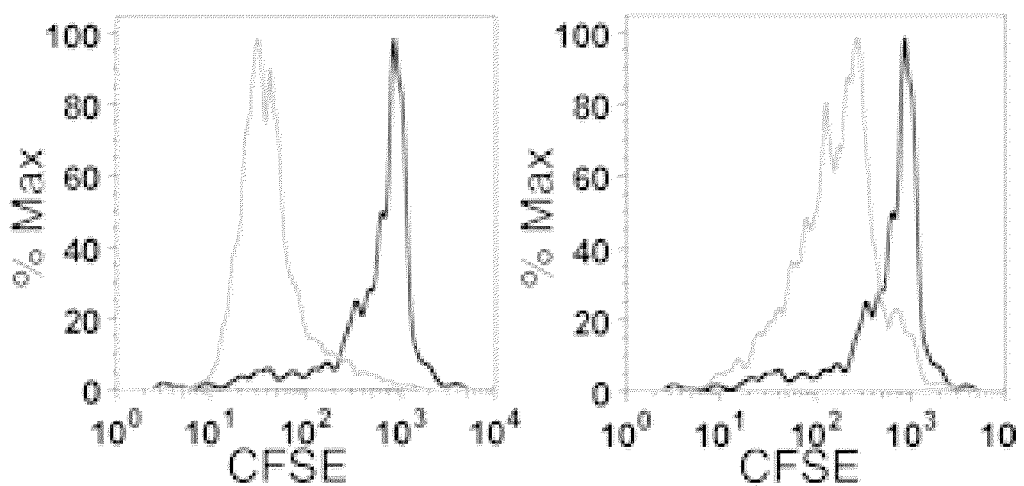

A cohort of xenochimaeric mice engrafted with $10^6$ expanded G-CSF mobilized cells expanded in vitro in a cocktail of cytokines supplemented with Tat-Myc and Tat-Bcl-2 (black squares) were assessed for myeloid and lymphoid cell differentiation. The CD45 positive population of bone marrow cells (FIG. 7F) and spleen cells (FIG. 7G) were analyzed for CD11b, CD33, CD3, and CD19 expression. Both myeloid and lymphoid cell differentiation was observed in the bone marrow and spleen of these xenochimaeric mice. In addition, the mature human B-cells derived from the primary xenotranplant responded to stimulation of the antigen receptors in vitro, as determined by CFSE dilution by flow cytometry (FIG. 6C). Similar observations were derived when mature human B cells that developed from the first serial transplant were activated in vitro with antibodies to IgM and CD40 (FIG. 8).

This method is able to generate a sufficient number of HSCs needed for transplantation of an average size adult according to current approaches (Sideri, A., et al. (2011). An overview of the progress on double umbilical cord blood transplantation. Hematologica 96, 1213-20.).

Example 9

Generation of Biologically Active Myc Fusion Proteins

Figure 9A:
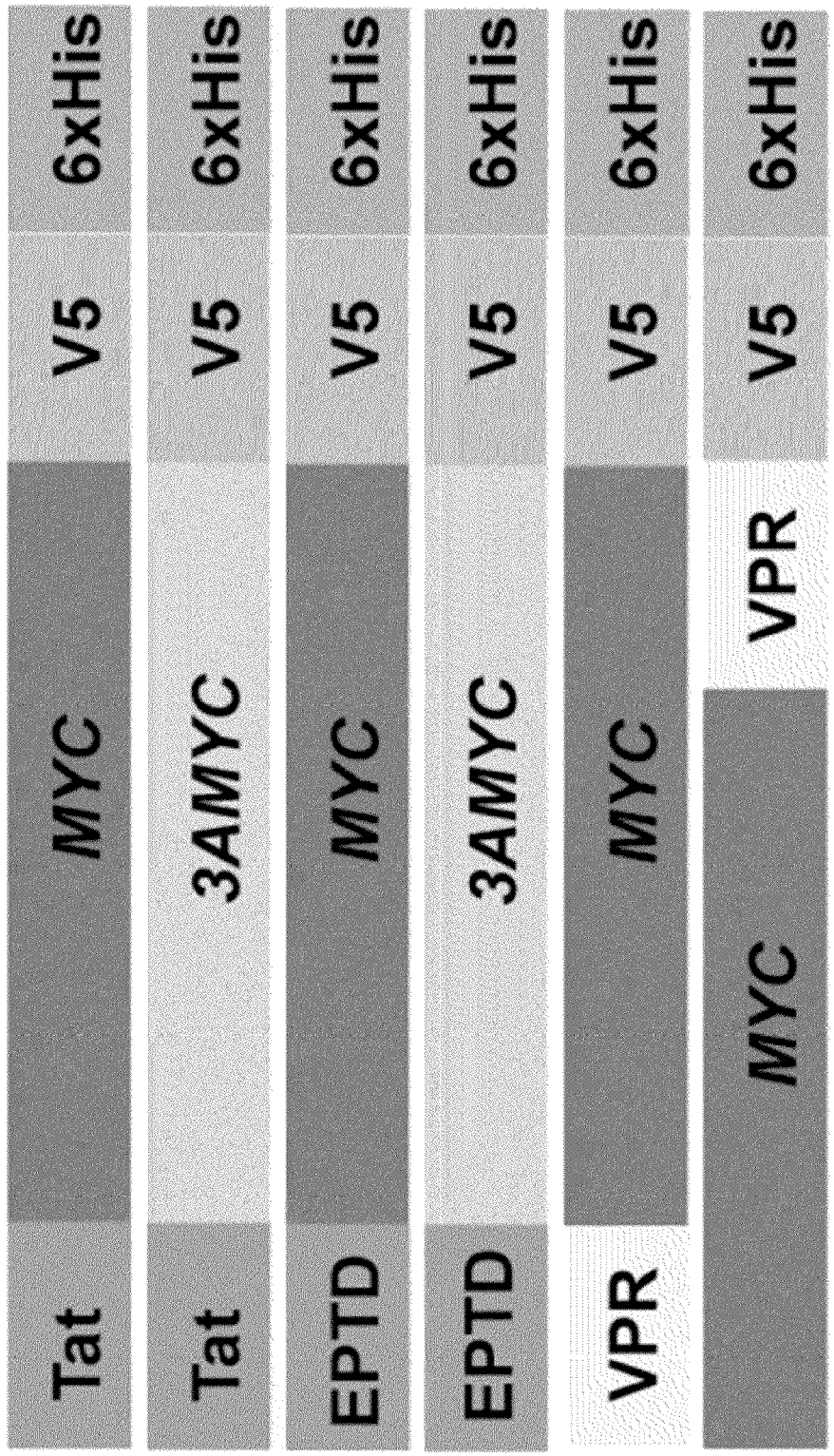

Five Myc fusion proteins in addition to the Tat-Myc fusion protein described in Example 1 were generated and purified using the same approach described there. The plasmids were made by PCR amplification of the coding region using a forward primer that contains an in frame N-terminal PTD-amino-acid sequence and a reverse primer that removed the stop codon. The PCR product was then cloned into pET101/D-Topo (Invitrogen) vector, which includes a C-terminal V5 epitope and 6x-histidine purification tag. FIG. 9A shows a diagrammatic representation of the Myc fusion proteins as compared with Tat-Myc from Example 1. In each, a protein transduction (PTD) is fused in frame before or after the Myc polypeptide.

Protein transduction domains included Tat, EPTD, and Vpr. EPTD is an optimized protein transduction domain (YARAAARQARA SEQ ID NO: 6) taken from Ho, A. et al. (Synthetic protein transduction domains: enhanced transduction potential in vitro and in vivo. Cancer Res. (2001) 61:474-477). Vpr transduction domain was as identified by Taguchi, T. et al. (Nuclear trafficking of macromolecules by an oligopeptide derived from Vpr of human immunodeficiency virus type-1. Biochem. Biophys. Res. Commun. (2004) 320 (1):18-26).

Myc was either the ORF of the polypeptide as described in Example 1, or of the 3AMyc sequence previously described by Huang, Z. et al. (Negative control of the Myc protein by the stress-responsive kinase Pak-2. Mol Cell Biol (2004) 24(4): 1582-94). The recombinant proteins also encoded a V5 peptide tag and a 6-His tag, to facilitate detection and purification. (FIG. 9A).

Example 10

Activated T Cell Survival Assays

Figure 9B:
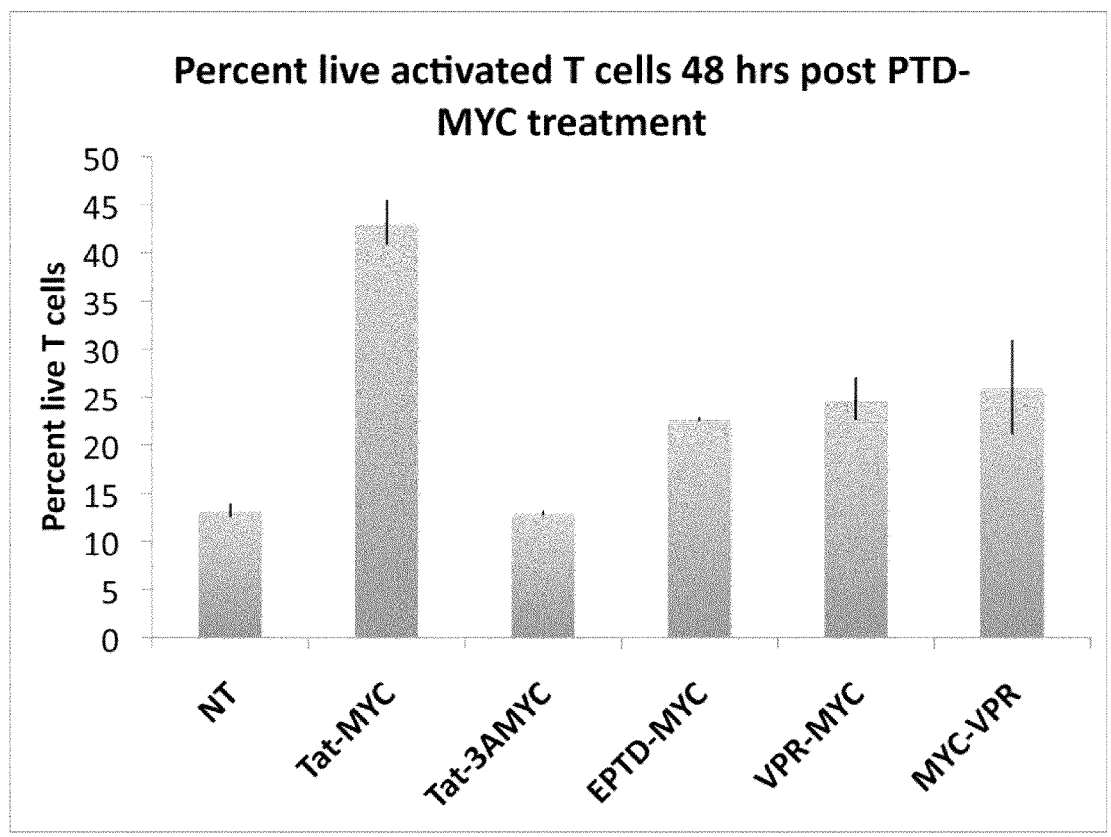

The Myc fusion proteins described in Example 9 Tat-Myc, Tat-3AMyc, EPTD-Myc, Vpr-Myc, and Myc-Vpr) were tested for Myc biological activity in an activated T cell viability assay (FIG. 9B). A spleen was harvested from a C57BL.6j (Jackson) mouse, and mechanically dissociated through wire mess. The red blood cells were removed, and the T cells were activated with 1 ug/ml anti-CD3 (2c11). The cells were plated into a 24 well cluster dish at $3\times10^{\wedge}6$ cells per well in 1 ml of media. 48 hrs later, the live cells were captured on a Ficol cushion, washed, and plated in a 24 well cluster dishes at $1\text{-}1.5\times10^{\wedge}6$ cells per well. The PTD-Myc proteins were titrated onto the T cells at 0.5, 1, 5, 10, 25, or 50 ug/ml. 48 hrs after the PTD-Myc protein treatment, the cells were assessed for viability by flow cytometry (forward×side-scatter). In FIG. 9B, the data presented are for the 25 ug/ml protein treatment.

As shown in FIG. 9B, all the constructs tested, except Tat-3AMyc, resulted in greater T cell viability after 48 hours than the untreated control. However, no construct resulted in greater T cell viability than Tat-Myc described in Example 1.

In a similar experiment, the activity of Tat-Myc and Tat-Bcl-2 at various concentrations is shown in Table 5, below. T cells from spleens of C57BL.6j (Jackson) mice are activated with 1 ug/ml anti-CD3 (2c11). Following activation (48 hours later), the cells were washed, were plated at about $1\text{-}1.5\times10^6$ cells/well, and fusion proteins (Tat-Myc or Tat-Bcl-2) at various concentrations (0.5, 1, 5, 10, 25, or 50 ug/ml) were added. After 48 hours, the percent of live cells was determined by flow cytometry (forward×side scatter) as shown in Table 5, below.

TABLE 5

| Concentration [ug/ml] | Tat-Myc (% viable) | Tat-Bcl2 (% viable) |
|---|---|---|
| 0 | 8.5 | 3.1 |
| 0.5 | 9.5 | 5 |
| 1 | 11.4 | 7.68 |
| 5 | 21.1 | 14.3 |
| 10 | 22.4 | 24.4 |
| 25 | 31.9 | 25 |
| 50 | 32.8 | 19.8 |

For both Tat-Myc and Tat-Bcl-2, and at all concentrations tested, cell viability and/or proliferation is increased as compared with cells incubated in the absence of either fusion protein.

In a separate experiment using the same methods, FIG. 10 provides the FACS data for the live gate for activated T cells treated with 50 ug/ml of fusion proteins; Tat-Bcl-2 and Tat-Myc are compared with control (Tat-Cre or no treatment). As shown, both Tat-Myc and Tat-Bcl-2 treatments result in significantly improved T cell survival and/or proliferation.

Example 11

Evaluation of Cytokine Cocktails for CD34+ Expansion

A variety of cytokine cocktails in base media were tested for their ability to support stem cell survival and/or proliferation.

On Day 0, cord blood was overlayered on a Ficoll gradient to enrich for mononuclear cells and remove red cells. The cells were then washed and incubated in StemSpan media alone, or with various cytokine combinations as shown in Table 6, below.

To generate cytokines, 293FT cells were plated in 150 mm plates at $12\times10^6$ cells per plate in D10 media (DMEM, 10% FBS, 100 units per ml Penn/Strep, MEM NEAA (Gibco), 2 mM L-glutamine (Gibco)). The cells were transfected with 30 μg total DNA per plate consisting of 10 μg pcDNA3.1-SCF, 10 μg pcDNA3.1-IL3, and 10 μg pcDNA3.1-IL6 or 10 μg pcDNA3.1-TPO, 10 μg pcDNA3.1-Flt3-L, and 10 μg pcDNA3.1-GM-CSF using calcium phosphate. The following day the media was removed and replaced with 100 ml D10 media. Cells were incubated at 37° C./5% $CO_2$ for 4-5 days. The media was collected, sterile filtered, and frozen at −20° C. in 30 ml aliquots. Cytokines were added to the expansion media by adding 30 mls of conditioned media containing the three cytokines IL3, IL6, SCF, and 30 mls of conditioned media containing TPO, Flt3-L, GM-CSF per 500 ml bottle of media.

On days 4, 7, 10, 13, 16, and 19, samples were taken to determine the percent of CD34+ cells by flow cytometry using standard techniques. Cytokines were not replenished after Day 0. As shown in Table 6, the combination of StemSpan media plus Il-3, Il-6, TPO (thrombopoeitin), Flt3-L, and GM-CSF showed the best survival and proliferation to cells (see, for example, Day 13).

TABLE 6

| Day | StemSpan (SS) alone | SS plus Il-3 and Il-6 | SS plus Il-3, Il-6, Tepo, Flt3-L, GM-CSF | SS plus Il-3, Il-6, Tepo, Flt3-L | SS plus Tepo, Flt3-L |
|---|---|---|---|---|---|
| 0 | 4.2 | 4.2 | 4.2 | 4.2 | 4.2 |
| 4 | 0.8 | 2.51 | 2.52 | 1.4 | 1.5 |
| 7 | 0.9 | 7.08 | 9 | 16 | 9.05 |
| 10 | 2.14 | 10.5 | 14.9 | 12 | 11.6 |
| 13 | 2.14 | 13.2 | 21.6 | 10.8 | 13.9 |
| 16 | 2.25 | 17 | 16.4 | 2.5 | 8 |
| 19 | 1.33 | 5.2 | 5.2 | 1 | 2.6 |

A variety of cytokine cocktails in base media with or without Tat fusion proteins (TMTB) were tested for their ability to support stem cell survival and/or proliferation.

Cord blood was prepared on Ficol density gradient to remove the red blood cells. 20,000 nucleated cells were plated into wells of a 24 well dish. The cells were seeded in StemSpan containing: Stem Cell Factor, IL3, and IL6 (S36); S36 plus 5 ug/ml Tat-Myc and 5 ug/ml Tat-Bcl2; TPO, Stem Cell Fact, Flt3-L, IL3, and IL6 (TSF36); TSF36 plus 5 ug/ml Tat-Myc and 5 ug/ml Tat-Bcl2; TPO, Stem Cell Fact, Flt3-L, IL3, IL6, GM-CSF (TSF36G); and TSF36G plus 5 ug/ml Tat-Myc and 5 ug/ml Tat-Bcl2. Media and Tat-Fusion proteins were replaced every three days. The cells were assessed by flow cytometry for CD34 positive linage negative HSC on day 13.

Figure 11:
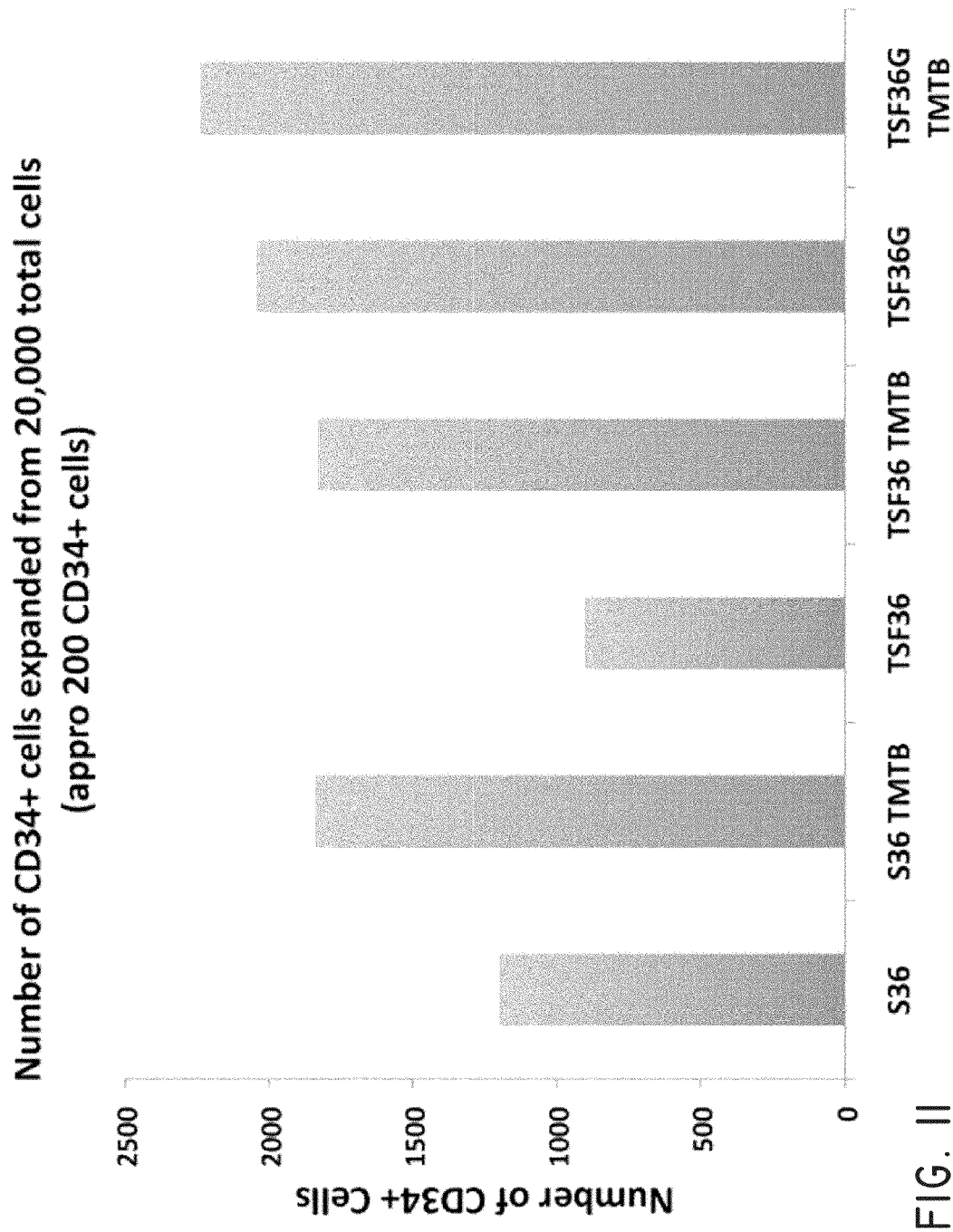
Figure 12:
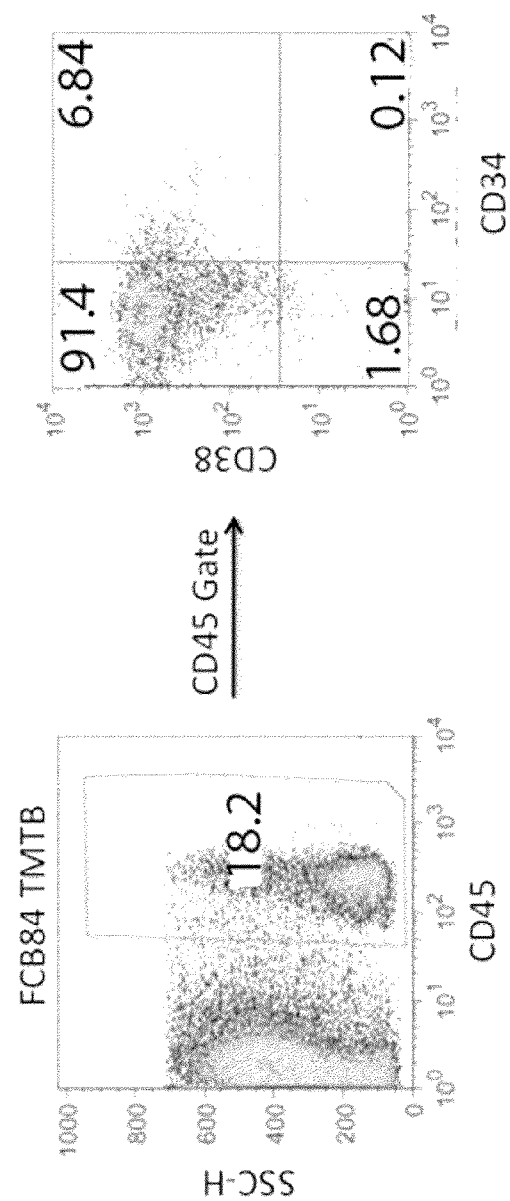
Figure 14:
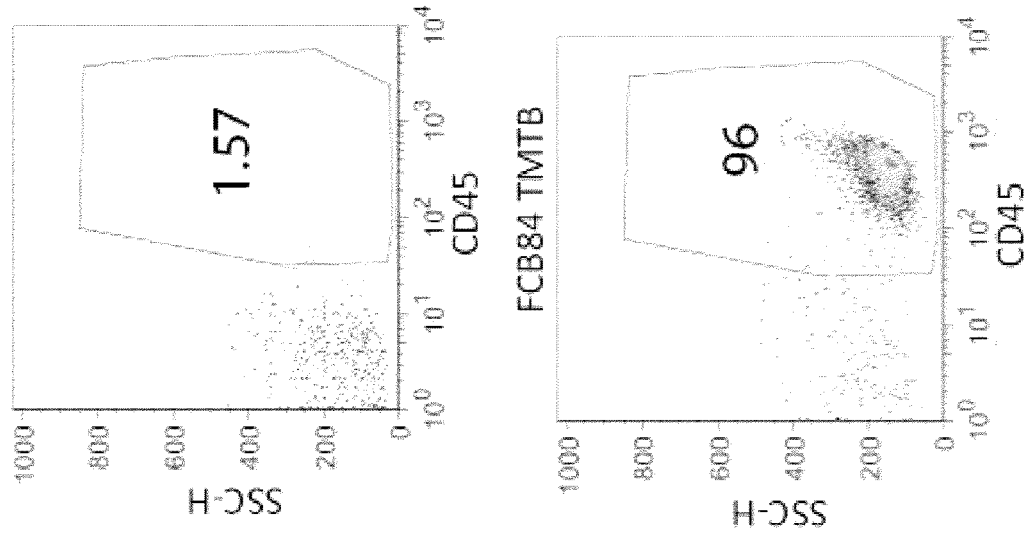

As shown in FIG. 11, TSF36G plus the fusion proteins provided the highest viability and proliferation. In other experiments, this combination of cytokines plus fusion proteins was shown to produce cells that significantly outperformed cells produced from the cytokine cocktail without fusion proteins in colony forming assays, and in vivo reconstitution of xenochimaeric mice (FIGS. 12-14).

For the in vivo reconstitution of xenochimaeric mice experiments, cord blood cells were prepared on a Ficol gradient. The Buffy coat was removed, and the cells were washed 3 times in PBS. Half of the cord blood cells were seeded in FCB (fetal cord blood) media consisting of Iscove's media (Gibco) supplemented with 10% human plasma, 100 units per ml Penn/Strep, 30 ml of media containing SCF, IL3 and IL6 and 30 mls of media containing TPO, FLT3-L, and GM-CSF. The other half of the cells were seeded in FCB media including the additions noted above, that was further supplemented with 5 μg/ml recombinant Tat-Myc, and 5 μg/ml recombinant Tat-Bcl-2.

The cells were expanded for 11 days. On day 13, the cells were spun down and resuspended in 10 ml of fresh FCB media. The cells that were originally treated with Tat-Myc and Tat-Bcl2 were again treated with 5 μg/ml recombinant Tat-Myc, and 5 μg/ml recombinant Tat-Bcl-2 for 1 hour at 37 degrees. Both populations of FCB cells were washed 3× in PBS for injection into mice.

The expanded cells were injected into NOD/SCID/gc$^{-/-}$ mice (NSG) mice (Jackson Laboratory) that received 180 rads of radiation just prior to injection. The expanded cells were injected into NSG mice via the tail vein in 200 μl PBS. Eight weeks post-transplant, the bone marrow (BM), spleen, and thymus were assessed for human HSC reconstitution by flow cytometry (FIGS. 12-14). Cells from each tissue that had been pre-treated with Tat-Myc and Tat-Bcl2 prior to transfusion showed a significant increase in human CD45+ cells as compared with cells not pre-treated with the fusion proteins.

Example 12

Evaluation of Bcl-2

3T3 cells were transduced with Tat-Bcl2 for 1 hour followed by 3 PBS washes. Two hours post-transduction, the cells were Trypsanized, counted, and $5\times10^6$ were harvested. The nuclear and cytoplasmic fractions were isolated. $5\times10^6$ cells were harvested every 24 hours for the next 5 days. Nuclear and cytoplasmic proteins were prepared by lysing cells in 10 mM HEPES (pH 7.6), 10 mM $NaCl_2$, 3 mM $CaCl_2$, and 0.5% NP40. Nuclei were pelleted, and the cytoplasmic-containing supernatant fraction was precipitated with trichloroacetic acid (TCA). Western blots were probed with anti-V5 antibody (Invitrogen), and goat anti-mouse IgG-HRP (Santa Cruz Biotechnology).

Tat-Bcl2 was observed in the cytoplasmic fraction at 24 and 48 hours. The signal began to diminish by 72 hrs post transduction and was no longer observed at the 96 hour time point.

Plasmids expressing Tat-Bcl2, Tat-Bcl2Δ, EPTD-Bcl2, VPR-Bcl2, VPR-Bcl2Δ, and VPR-BclXL were created. pPTD-Bcl2-V5-6×His(Amp$^R$): plasmids were generated by PCR amplification of a cDNA encoding human Bcl2 using a forward primer encoding an in frame PTD (Tat, EPTD or VPR) protein transduction domain. The PCR products were cloned into pET101/D-Topo (Invitrogen) vector. To generate the Bcl2Δ the unstructured loop (A.A. #27-80) was removed from the BCL-2 coding sequence using a Quick Change site directed mutagenesis kit (Stratagene #200521-5). VPR-BclXL was made in a similar fashion as the PTD-Bcl2 described above, but using the cDNA of human BclXL rather then Bcl2.

In this application, the use of the singular can include the plural unless specifically stated otherwise or unless, as will be understood by one of skill in the art in light of the present disclosure, the singular is the only functional embodiment.

Thus, for example, "a" can mean more than one, and "one embodiment" can mean that the description applies to multiple embodiments.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. A method for producing a population of conditionally immortalized adult stem cells comprising: providing one or more adult stem cells with
   a) an exogenously synthesized Myc-fusion polypeptide that promotes one or more of cell survival or proliferation; and
   b) an exogenously synthesized Bcl-2 domain polypeptide that inhibits apoptosis; and
   wherein the Myc-fusion polypeptide is provided to the one or more adult stem cells at intervals of at least 24 hours, and wherein the Myc-fusion polypeptide is continuously provided to the cells for at least 24 hours;
   wherein the Bcl-2 domain polypeptide is provided to the one or more adult stem cells at intervals of at least 24 hours, so as to produce a population of conditionally immortalized adult stem cells; and wherein the Myc-fusion polypeptide comprises a Myc polypeptide fused to a protein transduction domain.

2. The method of claim 1, wherein the Myc-fusion polypeptide is provided at intervals at least 72 hours; and the Bcl-2 domain polypeptide is at intervals of at least 72 hours.

3. The method of claim 1, wherein the Myc polypeptide of the Myc-fusion polypeptide is one or more of n-Myc, c-Myc, l-Myc, v-Myc, or s-Myc.

4. The method of claim 1, wherein the Myc-fusion polypeptide is provided at a concentration of about 1 ug/ml to about 50 ug/ml.

5. The method of claim 1, wherein the Bcl-2 domain polypeptide is provided at a concentration of about 1 ug/ml to about 50 ug/ml.

6. The method of claim 1, wherein the Bcl-2 domain polypeptide includes BH1, BH2, BH3, and BH4.

7. The method of claim 1, wherein the one or more Bcl-2 domain polypeptide is one or more of Bcl-2, Bcl-w, Bcl-X, Bel-XL, Mcl-1.

8. The method of claim 1, wherein the one or more Bcl-2 domain polypeptide is Bcl-2.

9. The method of claim 1, wherein the Bcl-2 polypeptide includes a protein transduction domain selected from the group consisting of Tat, EPTD and vpr.

10. The method of claim 1, wherein the protein transduction domain is Tat.

11. The method of claim 1, wherein the protein transduction domain is EPTD.

12. The method of claim 1, wherein the protein transduction domain is vpr.

13. The method of claim 1, wherein the one or more adult stem cells are cultured in media comprising IL3, IL6, and stem cell factor.

14. The method of claim 1, wherein the one or more adult stem cells are cultured in media comprising IL3, IL6, stem cell factor, thrombopoeitin, and Flt3-L, and GM-CSF.

15. The method of claim 1, wherein the one or more adult stem cells are expanded one or more of about 270 fold over about 28 days, about 150 fold over about 14 days, 100 fold over about 21 days, or about 85 fold over about 9 to 14 days.

16. The method of claim 1, wherein the one or more adult stem cells are one or more hematopoietic adult stem cells.

17. The method of claim 1, wherein, over a 8 hour period, no more than 1 µg/ml of Myc-fusion polypeptide is provided.

18. The method of claim 1, wherein producing the population occurs within a gas permeable container.

19. The method of claim 1, wherein the Myc-fusion polypeptide is provided at intervals at least 96 hours; and the Bcl-2 domain polypeptide is at intervals of at least 96 hours.

20. The method of claim 1, wherein the Myc-fusion polypeptide is detectable in the cells 48 hours after being provided to the one or more adult stem cells.

21. The method of claim 1, wherein the Myc-fusion polypeptide is provided at intervals at least 48 hours; and the Bcl-2 domain polypeptide is at intervals of at least 48 hours.

22. A method for producing a population of conditionally immortalized adult stem cells comprising:
providing one or more adult stem cells with
a) an exogenously synthesized Myc-fusion polypeptide that promotes one or more of cell survival or proliferation, wherein the Myc-fusion polypeptide is provided at a concentration of about 1 ug/ml to about 50 ug/ml; and
b) an exogenously synthesized Bcl-2 domain polypeptide that inhibits apoptosis, wherein the Bcl-2 domain polypeptide is provided at a concentration of about 1 ug/ml to about 50 ug/ml; and
wherein the Myc-fusion polypeptide is provided to the one or more adult stem cells at intervals of at least 24 hours;
wherein the Bcl-2 domain polypeptide is provided to the one or more adult stem cells at intervals of at least 24 hours, so as to produce a population of conditionally immortalized adult stem cells; and wherein the Myc-fusion polypeptide comprises a Myc polypeptide fused to a protein transduction domain.

23. The method of claim 22, wherein the Myc-fusion polypeptide is provided at intervals at least 48 hours; and the Bcl-2 domain polypeptide is at intervals of at least 48 hours.

24. The method of claim 22, wherein the Myc-fusion polypeptide is provided at intervals at least 72 hours; and the Bcl-2 domain polypeptide is at intervals of at least 72 hours.

25. The method of claim 22, wherein the one or more Bcl-2 domain polypeptide is Bcl-2.

26. The method of claim 22, wherein the Bcl-2 polypeptide includes a protein transduction domain.

27. The method of claim 26, wherein the protein transduction domain is Tat.

28. The method of claim 22, wherein the Myc polypeptide is c-Myc and the protein transduction domain is Tat.

29. The method of claim 22, wherein the one or more adult stem cells are one or more hematopoietic adult stem cells.

* * * * *